United States Patent [19]

Walsh et al.

[11] Patent Number: 5,635,384
[45] Date of Patent: Jun. 3, 1997

[54] RIBOSOME-INACTIVATING PROTEINS, INACTIVE PRECURSOR FORMS THEREOF, A PROCESS FOR MAKING AND A METHOD OF USING

[75] Inventors: Terence A. Walsh; Timothy D. Hey, both of Zionsville, Ind.; Alice E. R. Morgan, Midland, Mich.

[73] Assignee: DowElanco, Indianapolis, Ind.

[21] Appl. No.: 378,761

[22] Filed: Jan. 26, 1995

Related U.S. Application Data

[63] Continuation of Ser. No. 987,927, Dec. 9, 1992, abandoned, which is a continuation-in-part of Ser. No. 535,636, Jun. 11, 1990, Pat. No. 5,248,606.

[51] Int. Cl.$^6$ .................................................. C12N 7/04
[52] U.S. Cl. .................. 435/199; 435/68.1; 435/69.1; 435/69.7; 435/252.3; 435/320.1; 536/23.2; 530/370; 530/379; 530/395; 530/396; 530/376
[58] Field of Search .................. 435/68.1, 69.1, 435/69.7, 252.3, 320.1, 199; 536/23.2; 530/370, 379, 395, 396, 376

[56] References Cited

U.S. PATENT DOCUMENTS

| | | | |
|---|---|---|---|
| 4,869,903 | 9/1989 | Lifson et al. | 424/195.1 |
| 4,894,443 | 1/1990 | Greenfield et al. | 530/388 |
| 5,079,163 | 1/1992 | Piatak, Jr. et al. | 435/252.3 |
| 5,101,025 | 3/1992 | Piateak, Jr. et al. | 536/23.2 |
| 5,128,460 | 7/1992 | Piatak, Jr. et al. | 536/23.2 |
| 5,166,056 | 11/1992 | Piatak, Jr. et al. | 435/69.1 |

FOREIGN PATENT DOCUMENTS

| | | | |
|---|---|---|---|
| 7556487 | 1/1988 | Australia | 530/370 |
| 2057313 | 6/1992 | Canada . | |
| 390040 | 3/1990 | European Pat. Off. | 530/370 |
| 402544 | 12/1990 | European Pat. Off. | 536/23.6 |
| 0466222 | 1/1992 | European Pat. Off. . | |
| 0504919 | 9/1992 | European Pat. Off. . | |
| 2194241 | 7/1987 | United Kingdom | 530/370 |
| 2216891 | 1/1989 | United Kingdom | 536/23.6 |

| | | | |
|---|---|---|---|
| 8703286 | 6/1987 | WIPO | 330/370 |
| 9010457 | 9/1990 | WIPO . | |
| 9012034 | 10/1990 | WIPO . | |
| 9012597 | 11/1990 | WIPO . | |
| 9204918 | 4/1992 | WIPO . | |
| 9211872 | 7/1992 | WIPO . | |
| 9218148 | 10/1992 | WIPO . | |

OTHER PUBLICATIONS

Hartings et al., (1990), Plant Molecular Biology, 14 1031–1040.
Lohmer et al., (1991), the EMBO Journal, 10(3) 617–24.
DiFonzo et al., (1986), Planta, 167:587–594.
DiFonzo et al., (1988), mol. Gen. Genet., 212:481–487.
Schwall, M. et al., 1988, Biological Abstracts, vol 86, No. 7, p. AB489–490, Abstract 69622.
Bass, H. et al. 1992, The Plant Cell, vol. 4, 225–234.
Walsh, T.A., Morgan, A.E., and Hey, T.D., 1991, The Journal of Biological Chemistry, 266(34): 23422–23427.
Chon, P.Y., and Fusman, G.D., 1978, Annual review of Biochemistry, 47:251–276.
Chothia, L., and Tesk, A.M., 1986, The EMBO Journal, 5(4):823–826.
Boswell, P.R., and Lesk, A.M., 1988, in Computational Moleculur Biology, Lesk, A.M., Ed., pp. 161–178. Oxford University Press.
Montanaro, L., et al., 1985, The Italian Journal of Biochemistry, 34(1):1–10.
Ovain, M., et al., 1988, Archives of Biochemistry and Biophysics, 264(1):168–175.
Benalti, L., et al., 1989, Eurpean Journal of Biochemistry, 183(2):465–470.

(List continued on next page.)

Primary Examiner—Robert A. Wax
Assistant Examiner—Nashaat T. Nashed
Attorney, Agent, or Firm—Andrea T. Borucki

[57] ABSTRACT

The present invention is directed to a ribosome inactivating proteins. The proteins are characterized by being in a single chain proRIP inactive form that can be converted into an active form by cleavage with proteases.

7 Claims, 53 Drawing Sheets

OTHER PUBLICATIONS

Collins, E.J., et al., 1990, The Journal of Biological Chemistry, 265(15):8665–8669.

Chow, T.P., et al., 1990, The Journal of Biological Chemistry, 265(15): 8670–8674.

Bolognesi, A., et al., 1990, Biochimica et Biophysica Acta. 1087(3):293–302.

Lord, J.M., et al., 1991, Seminansin Cell Biology, 2(1): 15–22.

Ho, W.K.K., et al., 1991, Biochimica et Biophysica Acta 1088(2):311–314.

Kataoka, J., et al., 1991, The Journal of Biological Chemistry, 266(13):8426–8430.

Wood, K.A., et al., 1991, European Journal of Biochemistry, 198(3):723–732.

Katzin, B.J., et al., 1991, Proteins: Structure, Function, and Genetics, 10(3):251–259.

Singh, V., et al., 1991, Biochemistry International, 25(3):531–536.

Benatti, L., et al., 1991, FEBS Letters, 291(2):285–288.

Logemann, J., et al., 1992, Bio/Technology, 10(3):305–308.

Miyaro, M., et al., 1992, Journal of Moleculur Biology, 226(1):281–283.

Girbés, T., et al., 1992, Cellular and Moleculor Biology, 38(7):803–812.

Wong, R.N.S., et al., 1992, Biochemistry International, 28(4):585–593.

Stirpe, F., et al., 1992, Bio/Technology, 10(4):405–412.

FIG. 1A

```
1    GAA TTC GGC ACG AGC AAA GAG AAG GGA ATG GCC GAG ATA ACC CTA GAG CCG
1                                    Met Ala Glu Ile Thr Leu Glu Pro

52   AGT GAT CTT ATG GCG CAA ACA AAC AAA AGA ATA GTG CCA AAG TTC ACT GAA
9    Ser Asp Leu Met Ala Gln Thr Asn Lys Arg Ile Val Pro Lys Phe Thr Glu

103  ATC TTC CCC GTG GAG GAC AAC TAC CCT TAC AGC GCC TTC ATC GCG TCG
26   Ile Phe Pro Val Glu Asp Asn Tyr Pro Tyr Ser Ala Phe Ile Ala Ser

154  GTC CGG AAA GAC GTG ATC AAA CAC TGC ACC CAT AAA GGG ATC TTC CAG
43   Val Arg Lys Asp Val Ile Lys His Cys Thr Asp His Lys Gly Ile Phe Gln

205  CCC GTG CTG CTG CCA CCG AAG GTC AAG GTC CCG GAG CTA TGG TTC TAC ACA GAG
60   Pro Val Leu Leu Pro Pro Glu Lys Val Lys Val Pro Glu Leu Trp Phe Tyr Thr Glu

256  CTC AAA ACT AGG ACC AGC ATC ACG CTC GCC ATA CGC ATG GAC AAC CTG
77   Leu Lys Thr Arg Thr Ser Ile Thr Leu Ala Ile Arg Met Asp Asn Leu

307  TAC CTC GTG GGC TTC AGG ACC CCG GGC GGG GTG TGG GAG TTC GGC AAG
94   Tyr Leu Val Gly Phe Arg Thr Pro Gly Gly Val Trp Trp Glu Phe Gly Lys
```

FIG. 1B

```
358  GAC GGC GAC ACC CAC CTC CTC GGC GAC AAC CCC AGG TGG CTC GGC TTC GGC
111  Asp Gly Asp Thr His Leu Leu Gly Asp Asn Pro Arg Trp Leu Gly Phe Gly

409  GGC AGG TAC CAG GAC CTC ATC GGC AAC AAG GGT CTG GAG GTC ACC ATG
128  Gly Arg Tyr Gln Asp Leu Ile Gly Asn Lys Gly Leu Glu Thr Val Met

460  GGC CGC GCC GAA ATG GCC AGG ACC GTC AAC GAC CTG GCG AAG AAG AAG
145  Gly Arg Ala Glu Met Ala Arg Thr Val Asn Asp Leu Ala Lys Lys Lys

511  ATG GCG ACA CTG GAG GAG GTG AAG ATG CAG ATG CCG GAG
162  Met Ala Thr Leu Glu Glu Val Lys Met Gln Met Pro Glu

562  GCC GCT GAT CTG GCG GCA GCG GCT GAC CAG CAG CCA GCC GAC ACG AAG
179  Ala Ala Asp Leu Ala Ala Ala Ala Asp Gln Gln Pro Ala Asp Thr Lys

613  AGC AAG CTG GTG AAG CTG GTC ATG GTG TGC GAG GGG CTG CGG TTC AAC
196  Ser Lys Leu Val Lys Leu Val Met Val Cys Glu Gly Leu Arg Phe Asn

664  ACC GTG TCC CGC ACG GTG GAC GCG GGG TTC AAC AGC CAG CAC GGG GTG ACC
213  Thr Val Ser Arg Thr Val Asp Ala Gly Phe Asn Ser Gln His Gly Val Thr
```

FIG. 1C

```
715  TTG ACC GTG ACG CAG GGG AAG CAG GTG CAG AAG TGG GAC AGG ATC TCC AAG
230  Leu Thr Val Thr Gln Gly Lys Gln Val Gln Lys Trp Asp Arg Ile Ser Lys

766  GCG GCC TTC GAG TGG GCT GAC CAC CCC ACC GCT GTG ATC CCC GAC ATG CAG
247  Ala Ala Phe Glu Trp Ala Asp His Pro Thr Ala Val Ile Pro Asp Met Gln

817  AAG CTT GGC ATC AAG GAT AAG AAC GAA GCA GCG AGG ATC GTT GCG CTC GTT
264  Lys Leu Gly Ile Lys Asp Lys Asn Glu Ala Ala Arg Ile Val Ala Leu Val

868  AAG AAT CAA ACT ACT GCC GCT ACT GCT GCC AGT GCT GAC AAC GAC
281  Lys Asn Gln Thr Thr Ala Ala Thr Ala Ala Ser Ala Asp Asn Asp

919  GAC GAC GAG GCC TGA TCA ATG CAA CGA CAC ATC ATG ATC TGC TGC ACT
298  Asp Asp Glu Ala End

970  TAA TTA CTA TGT TCG TAT ACA AAT AAA TAC ACC CGG CGT ACG CGG TGT TCC

1021 TTA TAT GGT CTA AAA TGT AGC CAG TAA ATT TTA AAC TAC TTT CTC GTG CCG

1072 AAT TC
```

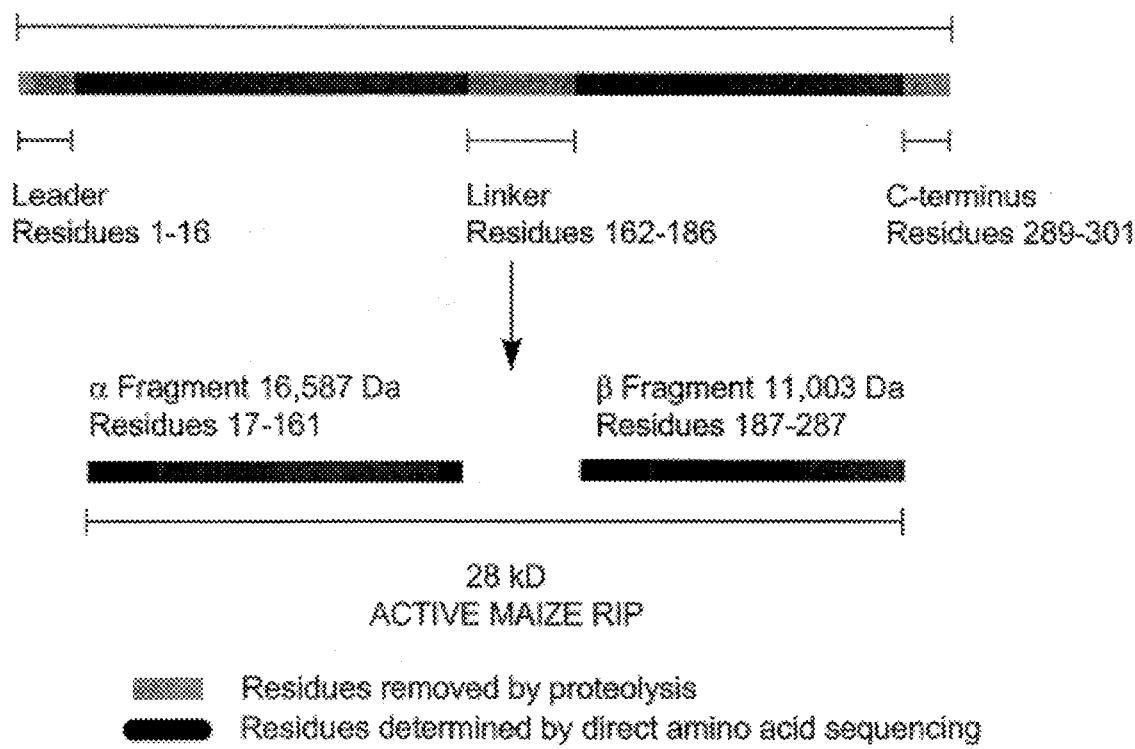

FIG. 3

```
Maize RIP   1   MAEITLEPSDLMAQTNKRIVPKFTEIFPVEDANYPYSAFIASVRKDVIKHCTDHKGIFQPV
                        ||||   |  |||| :     :||| |  : |||
Barley RIP  1   --------AAKMAKNVDKPLFTATFNVQASSADYATFIAGIRNKLRNPA--HFSHNEPV 61   LPP-EKKVPEL-WFYTELKTR-TSS-ITLAIRMDNLYLVGFRTPGGVWWEFGKDGDTHLLG
                ||| |  ||| ::    |   |   :||||| ||| ||| :  ||   :  | 
           50   LPPVEPNVPPSRWFHVVLKASPTSAGLTLAIRADNIYLEGFKSSDGTWWELTPGLIPGAT- 119   DNPRWLGFGGGRYQDLIGNKGLET--VTMGRAEMTRAVNDLAKKKKMATLEEEVKMQMPE
                      : ||||||  |||   :  |||| | :|| || :|  |
          110   -----YVGFGGTYRDLLGDTDKLTNVALGRQQLEDAVTALHGRTK---------------

187   AADLAAAAADPQADTKSKLVKLVVMCEGLRFNTVSRTVDAGFNSQHGVTLT----VTQG
                               :  ||  |||  ::  ||:| |||| |
          150   ---ADKASGPKQQQAREAVTTLLLMVNEATRFQTVSGFVAGLLHPKAVEKKSGKIGNEMK

236   KQVQKWDRISKAAFEWADHPTAVIPDMQKLGIKDKNEAARIVALVKNQTTAAAATAASADN
                ||: :||                    |     |||
          207   AQVNGWQDLS-AALLK----TDVKPPPGKSPAKFTPIEKMGVRTAEQ----AAATLGILLF

297   DDDEA
                 :
          259   VEVPGGLTVAKALELFHASGGK
```

FIG. 4

```
Maize RIP         1  ---------MAEITLEPSDLMAQTNKRIVPKFTEIFPVEDANYPYSAFIASVRKDVIKHCT
                               :  :     |  :                     |  ||  ||
Ricin A chain   -24  MYAVATWLCFGSTSGWSFTLEDNNIFPKQYPIINFTTAGATVQSYTNFIRAVRGRLTTGAD 62  DHKGIFQPVLPP-EKKVPELWF-YTELKTR-TSSITLAIRMDNLYLVGFRTPGGVWWEFGK
                            ||||          |   ||      |:|||:   | |:||:|     ::
                 38  VR--HEIPVLPNRVGLPINQRFILVELSNHAELSVTLALDVTNAYVVGYRAGNSAYFFHPD 110  DGDTHLLGDNPR-------WLGFGGRYQDLIGNKGL--ETVTMGRAEMTRAVNDLAKKKKM
                       :                  :||| |  |    |   | :  |      |:  |
                 97  NQEDAEAITHLFTDVQNRYTFAFGGNYDRLEQLAGNLRENIELGNGPLEEAISALYYYST- 164  ATLEEEEVKMQMQMPEAADLAAAAAADPQADTKSKLVKLVVMVCEGLRFNTVSRTVDAGFN
                                              :          :  : |: |: ||: :
                157  -------------------------GGTQLPTLARSFIICIQMISEAARFQYIEGEMRTRIR 224  SQHGVTLTVTQGKQVQKWDRISKAAFEWADHPTAVIPDMQKLGI-KDKNEAARIVALVKNQ
                              :     : | |:| |  |      |     |:    |       |:  :
                194  YNRRSAPDPSVITLENSWGRLSTAIQESNQGAFASPIQLQRRNGSKFSVYDVSILIPIIAL 284  TTAAAATAASADNDDDEA
                          |   |
                255  MVYRCAPPPSQF

FIG. 5A

```
Maize RIP       AQTNKRIVPKFTEIF-PVEDANYPYSAFIASVRKDVIK
Barley RIP      AAKMAKNVDKPLFTATF-NVQASSADYATFIAGIRNKLRN
Ricin A         IFPKQYPIINFTTAGATVQSYTNFIRAVRGRLTT
Trichosanthin   DVSFRLSGATSSSYGVFISNLRKALPN
Momordin        DVSFRLSGADPRSYGMFIKDLRNALPF
Bryodin         DVSFRLSGATTTSYGVFIKNLREALPY
Gelonin         GLDTVSFSTKGATYITYVNFLNELRVKLKP
Dodecandrin     VNTIIYNVGSTTISNYATFMDNLRNEAKD
Pokeweed AP2    N-IVFDYENATPETYSNFLTSLREAVKD
Saporin 5       VTSITLDLVNPTAGQYSSFVDKIRNNVKD
Saporin 4       VIIYELNLQGTTKA

FIG. 5B

| | | | | | | |
|---|---|---|---|---|---|---|
| Maize RIP | 84 | ITLAIRMDNLYLVGF | 201 | LVVMVCEGLRFNTVS | 237 | QVQK-WDRISKA |
| Barley RIP | 76 | LTLAIRADNIYLEGF | 168 | LLLMVNEATRFQTVS | 208 | QVNG-WQDLSAA |
| Ricin A-chain | 70 | VTLALDVTNAYVVGY | 171 | CIQMISEAARFQYIE | 207 | LENS-WGRLSTA |
| Saporin-6 | 62 | VSLGLKRDNLYVVAY | 170 | AIQMTAEAARFRYIQ | 205 | EVN--WKKISTA |
| Abrin A-chain | 64 | IEVGIDVTNAYVVAY | 159 | IIQVASEAARFRYIS | 194 | LENN-WDNLRGV |
| SLT-1A | 62 | MIDSGSGDNLFAVDV | 183 | FVTVTAEALRFQIQR | 222 | TLN--WGRLSSV |
| Trichosanthin | 58 | DEVALDVTNV. . . | 161 | LIQSTSEAARYKFIE | 196 | LENSLWLALSKQ |
| | 77 | YLMGY | | | | |

FIG. 7A

```
     GCTTAATTAA TTAAGCTTAA AAGGAGGAAA AAAATTATGG CCGAGATAAC CCTAGAGCCG
1
 61  AGTGATCTTA TGGCGCAAAC AAACAAAAGA ATAGTGCCAA AGTTCACTGA AATCTTCCCC
121  GTGGAGGACG CGAACTACCC TTACAGCGCC TTCATCGCGT CGGTCCGGAA AGACGTGATC
181  AAACACTGCA CCGACCATAA AGGGATCTTC CAGCCCCGTGC TGCCACCCGA GAAGAAGGTC
241  CCGGAGCTAT GGTTCTACAC AGAGCTCAAA ACTAGGACCA GCTCCATCAC GCTCGCCATA
301  CGCATGGACA ACCTGTACCT CGTGGGCTTC AGGACCCCGG GCGGGGTGTG GTGGGAGTTC
361  GGCAAGGACG GCGACACCCA CCTCCTCGGC GACAACCCCA GGTGGCTCGG CTTCGGCGGC
421  AGGTACCAGG ACCTCATCGG CAACAAGGGT CTGGAGACCG TCACCATGGG CCGCGCCGAA
481  ATGACCAGGG CCGTCAACGA CCTGGCGAAG AAGAAGAAGA TGGCCGACACT GGAGGAGGAG
541  GAGGTGAAGA TGCAGATGCA GATGCCGGAG GCCGCTGATC TGGCGGCGGC GGCAGCGGCT
601  GACCCACAGG CCGACACGAA GAGCAAGCTG GTGAAGCTGG TGGTCATGGT GTGCGAGGGG
661  CTGCGGTTCA ACACCGTGTC CCGCACGGTG GACGCGGGGT TCAACAGCCA GCACGGGGTG
```

FIG. 7B

```
721   ACCTTGACCG TGACGCAGGG GAAGCAGGTG CAGAAGTGGG ACAGGATCTC CAAGGCGGCC
781   TTCGAGTGGG CTGACCACCC CACCGCTGTG ATCCCCGACA TGCAGAAGCT TGGCATCAAG
841   GATAAGAACG AAGCAGCGAG GATCGTTGCG CTCGTTAAGA ATCAAACTAC TGCCGCTGCC
901   GCTACTGCTG CCAGTGCTGA CAACGACGAC GACGAGGCCT GATCAATGCA ACGACACATC
961   ATGATCTGCT GCTGCACTTA ATTACTATGT TCGTATACAA ATAAATACAC CCGGCGTACG
1021  CGGTGTTCCT TATATGGTCT AAAATGTAGC CAGTAAATTT TAAACTACTT TCTCGTGCCG
1081  AATTCACTGG CCGGCATGCT ATATA
```

FIG. 8A

```
1    TCCCTCTAGATGCGGGCCTAATTAATTAAGCTTAAAAGGAGGAAAAAATT ATG AAA AGA
1                                                      Met Lys Arg>

60   ATA GTG CCA AAG TTC ACT GAA ATC TTC CCC GTG GAG GAC GCG AAC TAC
4    Ile Val Pro Lys Phe Thr Glu Ile Phe Pro Val Glu Asp Ala Asn Tyr>

108  CCT TAC AGC GCC TTC ATC GCG TCG GTC CGG AAA GAC GTG ATC AAA CAC
20   Pro Tyr Ser Ala Phe Ile Ala Ser Val Arg Lys Asp Val Ile Lys His>

156  TGC ACC GAC CAT AAA GGG ATC TTC CAG CCC GTG CTG CCA CCG GAG AAG
36   Cys Thr Asp His Lys Gly Ile Phe Gln Pro Val Leu Pro Pro Glu Lys>

204  AAG GTC CCG GAG CTA TGG TTC TAC ACA GAG CTC AAA ACT AGG ACC AGC
52   Lys Val Pro Glu Leu Trp Phe Tyr Thr Glu Leu Lys Thr Arg Thr Ser>

252  TCC ATC ACG CTC GCC ATA CGC ATG GAC AAC CTG TAC CTC GTG GGC TTC
68   Ser Ile Thr Leu Ala Ile Arg Met Asp Asn Leu Tyr Leu Val Gly Phe>

300  AGG ACC CCG GGC GGG GTG TGG GAG TTC GGG AAG GAC GGC GAC ACC
84   Arg Thr Pro Gly Gly Val Trp Glu Phe Gly Lys Asp Gly Asp Thr>

348  CAC CTC CTC GGC GAC AAC CCC AGG TGG CTC GGC TTC GGC GGC AGG TAC
100  His Leu Leu Gly Asp Asn Pro Arg Trp Leu Gly Phe Gly Gly Arg Tyr>
```

FIG. 8B

```
396  CAG GAC CTC ATC GGC AAC AAG GGT CTG GAG ACC GTC ACC ATG GGC CGC
116  Gln Asp Leu Ile Gly Asn Lys Gly Leu Glu Thr Val Thr Met Gly Arg>

444  GCC GAA ATG ACC AGG GCC GTC AAC GAC CTG GCG AAG AAG AAG ATG
132  Ala Glu Met Thr Arg Ala Val Asn Asp Leu Ala Lys Lys Lys Met>

492  GCG ACA CTG GAG GAG GAG GTG AAG ATG CAG ATG CAG ATG CCG GAG
148  Ala Thr Leu Glu Glu Glu Val Lys Met Gln Met Gln Met Pro Glu>

540  GCC GCT GAT CTG GCG GCG GCA GCT GAC CCA CAG CAG GCC GAC ACG
164  Ala Ala Asp Leu Ala Ala Ala Ala Asp Pro Gln Gln Ala Asp Thr>

588  AAG AGC AAG CTG GTG AAG CTG GTC ATG GTG TGC GAG GGG CTG CGG
180  Lys Ser Lys Leu Val Lys Leu Val Val Met Val Cys Glu Gly Leu Arg>

636  TTC AAC ACC GTG TCC CGC ACG GTG GAC GCC GGG TTC AAC AGC CAG CAC
196  Phe Asn Thr Val Ser Arg Thr Val Asp Ala Gly Phe Asn Ser Gln His>

684  GGG GTG ACC TTG ACC GTG ACG CAG GGG AAG CAG GTG CAG AAG TGG GAC
212  Gly Val Thr Leu Thr Val Thr Gln Gly Lys Gln Val Gln Lys Trp Asp>

732  AGG ATC TCC AAG GCG GCC TTC GAG TGG GCT GAC CAC CCC ACC GCT GTG
228  Arg Ile Ser Lys Ala Ala Phe Glu Trp Ala Asp His Pro Thr Ala Val>
```

FIG. 8C

```
780  ATC CCC GAC ATG CAG AAG CTT GGC ATC AAG GAT AAG AAC GAA GCA GCG
244  Ile Pro Asp Met Gln Lys Leu Gly Ile Lys Asp Lys Asn Glu Ala Ala>

828  AGG ATC GTT GCG CTC GTT AAG AAT CAA ACT ACT GCC GCT GCC GCT ACT
260  Arg Ile Val Ala Leu Val Lys Asn Gln Thr Thr Ala Ala Ala Ala Thr>

876  GCT GCC AGT GCT GAC AAC GAC GAC GAG GCC TGA TCAATGCAACGACAC
276  Ala Ala Ser Ala Asp Asn Asp Asp Glu Ala END

927  ATCATGATCTGCTGCACTTAATTACTATGTTCGTATACAAATAAATACACCCGGGCGTACG

990  CGGTGTTCCTTATATGGTCTAAAATGTAGCCAGTAAATTTAAACTACTTTCTCGTGCCGAAT

1053 TCACTGGCCGGGCATGCTATATA
```

FIG. 10A

```
                    GCTAATTAATTAAGCTTAAAAGGAGGAAAAAAATT ATG GCC GAG ATA ACC CTA GAG
1                                                       Met Ala Glu Ile Thr Leu Glu>
1

57    CCG AGT GAT CTT ATG GCG CAA ACA AAC AAA AGA ATA GTG CCA AAG TTC
      Pro Ser Asp Leu Met Ala Gln Thr Asn Lys Arg Ile Val Pro Lys Phe>
8

105   ACT GAA ATC TTC CCC GTG GAG GAC GCG AAC TAC CCT TAC AGC GCC TTC
      Thr Glu Ile Phe Pro Val Glu Asp Ala Asn Tyr Pro Tyr Ser Ala Phe>
24

153   ATC GCG TCG GTC CGG AAA GAC GTG ATC AAA CAC TGC ACC GAC CAT AAA
      Ile Ala Ser Val Arg Lys Asp Val Ile Lys His Cys Thr Asp His Lys>
40

201   GGG ATC TTC CAG CCC GTG CTG CCA CCG GAG AAG AAG GTC CCG GAG CTA
      Gly Ile Phe Gln Pro Val Leu Pro Pro Glu Lys Lys Val Pro Glu Leu>
56

249   TGG TTC TAC ACA GAG CTC AAA ACT AGG ACC AGC TCC ATC ACG CTC GCC
      Trp Phe Tyr Thr Glu Leu Lys Thr Arg Thr Ser Ser Ile Thr Leu Ala>
72

297   ATA CGC ATG GAC AAC CTG TAC CTC GTG GGC TTC AGG ACC CCG GGC GGG
      Ile Arg Met Asp Asn Leu Tyr Leu Val Gly Phe Arg Thr Pro Gly Gly>
88

345   GTG TGG TGG GAG TTC GGC AAG GAC GGC GAC ACC CAC CTC CTC GGC GAC
      Val Trp Trp Glu Phe Gly Lys Asp Gly Asp Thr His Leu Leu Gly Asp>
104
```

FIG. 10B

```
393   AAC CCC AGG TGG CTC GGC TTC GGC AGG TAC CAG GAC CTC ATC GGC
120   Asn Pro Arg Trp Leu Gly Phe Gly Arg Tyr Gln Asp Leu Ile Gly>

441   AAC AAG GGT CTG GAG ACC ATG GTC ACC ATG GCC GAA ATG ACC AGG
136   Asn Lys Gly Leu Glu Thr Met Val Thr Met Ala Glu Met Thr Arg>

489   GCC GTC AAC GAC CTG GCG AAG AAG AAG CGC GCC GCT GAC CCA CAG GCC
152   Ala Val Asn Asp Leu Ala Lys Lys Lys Arg Ala Ala Asp Pro Gln Ala>

537   GAC ACG AAG AGC AAG CTG GTG AAG CTG GTC ATG GTG TGC GAG GGG
168   Asp Thr Lys Ser Lys Leu Val Lys Leu Val Met Val Cys Glu Gly>

585   CTG CGG TTC AAC ACC GTG TCC CGC ACG GTG GAC GCG GGG TTC AAC AGC
184   Leu Arg Phe Asn Thr Val Ser Arg Thr Val Asp Ala Gly Phe Asn Ser>

633   CAG CAC GGG GTG ACC TTG ACC GTG ACG CAG GGG AAG CAG GTG CAG AAG
200   Gln His Gly Val Thr Leu Thr Val Thr Gln Gly Lys Gln Val Gln Lys>

681   TGG GAC AGG ATC TCC AAG GCG GCC TTC GAG TGG GCT GAC CAC CCC ACC
216   Trp Asp Arg Ile Ser Lys Ala Ala Phe Glu Trp Ala Asp His Pro Thr>

729   GCT GTG ATC CCC GAC ATG CAG AAG CTT GGC ATC AAG GAT AAG AAC GAA
232   Ala Val Ile Pro Asp Met Gln Lys Leu Gly Ile Lys Asp Lys Asn Glu>
```

FIG. 10C

```
777  GCA GCG AGG ATC GTT GCG CTC GTT AAG AAT CAA ACT ACT GCC GCT GCC
248  Ala Ala Arg Ile Val Ala Leu Val Lys Asn Gln Thr Thr Ala Ala Ala>

825  GCT ACT GCT GCC AGT GCT GAC AAC GAC GAC GAG GCC TGA TCAATGC
264  Ala Thr Ala Ala Ser Ala Asp Asn Asp Asp Glu Ala END

874  AACGACACATCATGATCTGCTGCTGCACTTAATTACTATGTTCGTATACAAATAAATACACCC

937  GGCGTACGCGGGTGTTCCTTATATGGTCTAAAATGTAGCCAGTAAATTTAAACTACTTCTCG

1000 TGCCGAATTCACTGGCCGGGCATGCTATATA
```

FIG. 11A

```
1    GCTTAATTAATTAAGCTTAAAAGGAGGAAAAAATT ATG AAA AGA ATA GTG CCA
1                                        Met Lys Arg Ile Val Pro>

55   AAG TTC ACT GAA ATC TTC CCC GTG GAG GAC GCG AAC TAC CCT TAC AGC
7    Lys Phe Thr Glu Ile Phe Pro Val Glu Asp Ala Asn Tyr Pro Tyr Ser>

103  GCC TTC ATC GCG TCG GTC CGG AAA GAC GTG ATC AAA CAC TGC ACC GAC
23   Ala Phe Ile Ala Ser Val Arg Lys Asp Val Ile Lys His Cys Thr Asp>

151  CAT AAA GGG ATC TTC CAG CCC CTG CCA CCG GAG AAG AAG GTC CCG
39   His Lys Gly Ile Phe Gln Pro Val Leu Pro Pro Glu Lys Lys Val Pro>

199  GAG CTA TGG TTC TAC ACA GAG CTC AAA ACT AGG ACC AGC TCC ATC ACG
55   Glu Leu Trp Phe Tyr Thr Glu Leu Lys Thr Arg Thr Ser Ile Thr>

247  CTC GCC ATA CGC ATG GAC AAC CTG TAC CTC GTG GGC TTC AGG ACC CCG
71   Leu Ala Ile Arg Met Asp Asn Leu Tyr Leu Val Gly Phe Arg Thr Pro>

295  GGC GGG GTG TGG GAG TTC GGG AAG GAC ACC CAC CTC CTC
87   Gly Gly Val Trp Trp Glu Phe Gly Lys Asp Thr His Leu Leu>

343  GGC GAC AAC CCC AGG TGG CTC GGC AGG TAC CAG GAC CTC
103  Gly Asp Asn Pro Arg Trp Leu Gly Gly Arg Tyr Gln Asp Leu>
```

FIG. 11B

```
391  ATC GGC AAC AAG GGT CTG GAG ACC GTC ACC ATG GGC CGC GCC GAA ATG
119  Ile Gly Asn Lys Gly Leu Glu Thr Val Thr Met Gly Arg Ala Glu Met>

439  ACC AGG GCC GTC AAC GAC CTG GCG AAG AAG AAG GCG GCT GAC CCA
135  Thr Arg Ala Val Asn Asp Leu Ala Lys Lys Lys Ala Ala Asp Pro>

487  CAG GCC GAC ACG AAG AGC AAG CTG GTG AAG CTG GTC ATG GTG TGC
151  Gln Ala Asp Thr Lys Ser Lys Leu Val Lys Leu Val Met Val Cys>

535  GAG GGG CTG CGG TTC AAC ACC GTG TCC CGC ACG GTG GAC GGG TTC
167  Glu Gly Leu Arg Phe Asn Thr Val Ser Arg Thr Val Asp Gly Phe>

583  AAC AGC CAG CAC GGG GTG ACC GTG ACG CAG AAG CAG GTG
183  Asn Ser Gln His Gly Val Thr Val Thr Gln Gly Lys Gln Val>

631  CAG AAG TGG GAC AGG ATC TCC AAG GCG GCC TTC GAG TGG GCT GAC CAC
199  Gln Lys Trp Asp Arg Ile Ser Lys Ala Ala Phe Glu Trp Ala Asp His>

679  CCC ACC GCT GTG ATC CCC GAC ATG CAG AAG CTT GGC ATC AAG GAT AAG
215  Pro Thr Ala Val Ile Pro Asp Met Gln Lys Leu Gly Ile Lys Asp Lys>

727  AAC GAA GCA GCG AGG ATC GTT GCG CTC GTT AAG AAT CAA ACT ACT GCC
231  Asn Glu Ala Ala Arg Ile Val Ala Leu Val Lys Asn Gln Thr Thr Ala>
```

FIG. 11C

```
775  GCT GCC GCT ACT GCT GCC AGT GCT GAC AAC GAC GAC GAG GCC TGA
247  Ala Ala Ala Thr Ala Ala Ser Ala Asp Asn Asp Asp Glu Ala END
823  TCAATGCAACGACACATCATGATCTGCTGCACTTAATTACTATGTTCGTATACAAATAAA
886  TACACCCGGCGTACGCGGGTGTTCCTTATATGGTCTAAAATGTAGCCAGTAAATTTAAACTAC
949  TTTCTCGTGCCGAATTCACTGGCCCGGGCATGCTATATA
```

FIG. 12A

```
1    TCCCTCTAGATGCGGCCTAATTAATTAAGCTTAAAAGGAGGAAAAAATT ATG
1                                                      Met

54   AAA AGA ATA GTG CCA AAG TTC ACT GAA ATC TTC CCC GTG GAG GAC GCG AAC
1    Lys Arg Ile Val Pro Lys Phe Thr Glu Ile Phe Pro Val Glu Asp Ala Asn

105  TAC CCT TAC AGC GCC TTC ATC GCG TCG GTC CGG AAA GAC GTG ATC AAA CAC
19   Tyr Pro Tyr Ser Ala Phe Ile Ala Ser Val Arg Lys Asp Val Ile Lys His

156  TGC ACC GAC CAT AAA GGG ATC TTC CAG CCC GTG CTG CCA CCG GAG AAG AAG
36   Cys Thr Asp His Lys Gly Ile Phe Gln Pro Val Leu Pro Pro Glu Lys Lys

207  GTC CCG GAG CTA TGG TTC TAC ACA GAG CTC AAA ACT AGG ACC AGC TCC ATC
53   Val Pro Glu Leu Trp Phe Tyr Thr Glu Leu Lys Thr Arg Thr Ser Ser Ile

258  ACG CTC GCC ATA CGC ATG GAC AAC CTG TAC CTC GTG GGC TTC AGG ACC CCG
70   Thr Leu Ala Ile Arg Met Asp Asn Leu Tyr Leu Val Gly Phe Arg Thr Pro

309  GGC GGG GTG TGG GAG TTC TGG TGG AAG GAC ACC CAC CTC CTC GGC
87   Gly Gly Val Trp Glu Phe Trp Trp Lys Asp Thr His Leu Leu Gly

360  GAC AAC CCC AGG TGG CTC GGC TTC GGC AGG TAC CAG GAC CTC ATC GGC
104  Asp Asn Pro Arg Trp Leu Gly Phe Gly Gly Arg Tyr Gln Asp Leu Ile Gly
```

FIG. 12B

| | | | | | | | | | | | | | | | | |
|---|---|---|---|---|---|---|---|---|---|---|---|---|---|---|---|---|
| 411 | AAC | AAG | GGT | CTG | GAG | ACC | GTC | ACC | ATG | GGC | CGC | GCC | GAA | ATG | ACC | AGG | GCC |
| 121 | Asn | Lys | Gly | Leu | Glu | Thr | Val | Thr | Met | Gly | Arg | Ala | Glu | Met | Thr | Arg | Ala |
| 462 | GTC | AAC | GAC | CTG | GCG | AAG | AAG | AAG | CTG | GCT | GAC | CCA | CAG | GCC | GAC | ACG | |
| 138 | Val | Asn | Asp | Leu | Ala | Lys | Lys | Lys | Leu | Ala | Asp | Pro | Gln | Ala | Asp | Thr | |
| 513 | AAG | AGC | AAG | CTG | GTG | AAG | CTG | GTG | ATG | TGC | GAG | GGG | CTG | CGG | TTC | | |
| 155 | Lys | Ser | Lys | Leu | Val | Lys | Leu | Val | Met | Cys | Glu | Gly | Leu | Arg | Phe | | |
| 564 | AAC | ACC | GTG | TCC | CGC | ACG | GTG | GAC | GCG | GGG | TTC | AAC | AGC | CAG | CAC | GGG | GTG |
| 172 | Asn | Thr | Val | Ser | Arg | Thr | Val | Asp | Ala | Gly | Phe | Asn | Ser | Gln | His | Gly | Val |
| 615 | ACC | TTG | ACC | GTG | TCC | ACG | CAG | GGG | AAG | CAG | GTG | CAG | AAG | TGG | GAC | AGG | ATC | TCC |
| 189 | Thr | Leu | Thr | Val | Ser | Thr | Gln | Gly | Lys | Gln | Val | Gln | Lys | Trp | Asp | Arg | Ile | Ser |
| 666 | AAG | GCG | GCC | TTC | GAG | TGG | GCT | GAC | CAC | CCC | ACC | GCT | GTG | ATC | CCC | GAC | ATG | |
| 206 | Lys | Ala | Ala | Phe | Glu | Trp | Ala | Asp | His | Pro | Thr | Ala | Val | Ile | Pro | Asp | Met | |
| 717 | CAG | AAG | CTT | GGC | ATC | AAG | GAT | AAG | AAC | GAA | GCA | GCG | AGG | ATC | GTT | GCG | CTC | |
| 223 | Gln | Lys | Leu | Gly | Ile | Lys | Asp | Lys | Asn | Glu | Ala | Ala | Arg | Ile | Val | Ala | Leu | |
| 768 | GTT | AAG | AAT | CAA | ACT | ACT | GCC | GCT | GCC | GCT | ACT | GCT | GGA | TCC | GCC | TGA | TCA | |
| 240 | Val | Lys | Asn | Gln | Thr | Thr | Ala | Ala | Ala | Ala | Thr | Ala | Gly | Ser | Ala | End | | |

FIG. 12C

819 ATGCAACGACACATCATGATCTGCTGCTGCACTTAATTACTATGTTCGTATACAAATAAATACACCC
886 GGCGTACGCGGTGTTCCTTATATGGTCTAAAATGTAGCCAGTAAATTTAAACTACTTTCTCGTGCC
953 GAATTCACTGGCCCGGCATGCTATATA

FIG. 13A

```
1    TCCCTCTAGATGCGGGCCTAATTAATTAAGCTTAAAAGGAGGAAAAAAATT ATG AAA
1                                                        Met Lys>

57   AGA ATA GTG CCA AAG TTC ACT GAA ATC TTC CCC GTG GAG GAC GCG
3    Arg Ile Val Pro Lys Phe Thr Glu Ile Phe Pro Val Glu Asp Ala>

102  AAC TAC CCT TAC AGC GCC TTC ATC GCG TCG GTC CGG AAA GAC GTG
18   Asn Tyr Pro Tyr Ser Ala Phe Ile Ala Ser Val Arg Lys Asp Val>

147  ATC AAA CAC TGC ACC GAC CAT AAA GGG ATC TTC CAG CCC GTG CTG
33   Ile Lys His Cys Thr Asp His Lys Gly Ile Phe Gln Pro Val Leu>

192  CCA CCG GAG AAG AAG GTC CCG GAG CTA TGG TTC TAC ACA GAG CTC
48   Pro Pro Glu Lys Lys Val Pro Glu Leu Trp Phe Tyr Thr Glu Leu>

237  AAA ACT AGG ACC AGC TCC ATC ACG CTC GCC ATA CGC ATG GAC AAC
63   Lys Thr Arg Thr Ser Ser Ile Thr Leu Ala Ile Arg Met Asp Asn>

282  CTG TAC CTC GTG GGC TTC GGC ACC CCG GGG GTG TGG TGG GAG
78   Leu Tyr Leu Val Gly Phe Arg Thr Pro Gly Val Trp Trp Glu>

327  TTC GGC AAG GAC GGC GAC ACC CAC CTC CTC GGC GAC AAC CCC AGG
93   Phe Gly Lys Asp Gly Asp Thr His Leu Leu Gly Asp Asn Pro Arg>
```

FIG. 13B

```
372  TGG CTC GGC TTC GGC AGG TAC CAG GAC CTC ATC GGC AAC AAG
108  Trp Leu Gly Phe Gly Arg Tyr Gln Asp Leu Ile Gly Asn Lys>

417  GGT CTG GAG ACC GTC ACC ATG GGC GAA ATG ACC AGG GCC
123  Gly Leu Glu Thr Val Thr Met Gly Glu Met Thr Arg Ala>
                                              NotI            PstI
462  GTC AAC GAC CTG GCG AAG AAG GCC GCC GCT GCA GAC
138  Val Asn Asp Leu Ala Lys Lys Ala Ala Ala Ala Asp>

507  CCA CAG GCC GAC ACG AAG AGC CTG GTG AAG CTG GTC ATG
153  Pro Gln Ala Asp Thr Lys Ser Leu Val Lys Leu Val Met>

552  GTG TGC GAG GGG CTG CGG TTC AAC ACC GTG TCC CGC ACG GTG GAC
168  Val Cys Glu Gly Leu Arg Phe Asn Thr Val Ser Arg Thr Val Asp>

597  GCG GGG TTC AAC AGC CAG CAC GGG GTG ACC TTG ACC GTG ACG CAG
183  Ala Gly Phe Asn Ser Gln His Gly Val Thr Leu Thr Val Thr Gln>

642  GGG AAG CAG GTG CAG AAG TGG GAC AGG ATC TCC AAG GCC TTC
198  Gly Lys Gln Val Gln Lys Trp Asp Arg Ile Ser Lys Ala Phe>
```

FIG. 13C

```
687  GAG TGG GCT GAC CAC CCC ACC GCT GTG ATC CCC GAC ATG CAG AAG
213  Glu Trp Ala Asp His Pro Thr Ala Val Ile Pro Asp Met Gln Lys>

732  CTT GGC ATC AAG GAT AAG AAC GAA GCA GCG AGG ATC GTT GCG CTC
228  Leu Gly Ile Lys Asp Lys Asn Glu Ala Ala Arg Ile Val Ala Leu>

777  GTT AAG AAT CAA ACT ACT GCC GCT GCC GCT ACT GCT GGA TCC GCC
243  Val Lys Asn Gln Thr Thr Ala Ala Ala Thr Ala Gly Ser Ala>

822  TGATCAATGCAACGACACATCATGATCTGCTGCACTTAATTACTATGTTCGTATACA
     End<

882  AATAAATACACCCGGCGTACGCGGTGTTCCTTATATGGTCTAAAATGTAGCCAGTAAATT

942  TTAAACTACTTTCTCGTGCCGAATTCACTGGGCCCGGGCATGCTATATA
```

FIG. 14A

```
  1          TCCCTCTAGATGCGGCCTAATTAAGCTTAAAGGAGGAAAAAATT ATG AAA
  1                                                       Met Lys>

57    AGA ATA GTG CCA AAG TTC ACT GAA ATC TTC CCC GTG GAG GAC GCG
  3    Arg Ile Val Pro Lys Phe Thr Glu Ile Phe Pro Val Glu Asp Ala>

102    AAC TAC CCT TAC AGC GCC TTC ATC GCG TCG GTC CGG AAA GAC GTG
 18    Asn Tyr Pro Tyr Ser Ala Phe Ile Ala Ser Val Arg Lys Asp Val>

147    ATC AAA CAC TGC ACC GAC CAT AAA GGG ATC TTC CAG CCC GTG CTG
 33    Ile Lys His Cys Thr Asp His Lys Gly Ile Phe Gln Pro Val Leu>

192    CCA CCG GAG AAG AAG GTC CCG GAG CTA TGG TTC TAC ACA GAG CTC
 48    Pro Pro Glu Lys Lys Val Pro Glu Leu Trp Phe Tyr Thr Glu Leu>

237    AAA ACT AGG ACC AGC TCC ATC ACG CTC GCC ATA CGC ATG GAC AAC
 63    Lys Thr Arg Thr Ser Ser Ile Thr Leu Ala Ile Arg Met Asp Asn>

282    CTG TAC CTC GTG GGC TTC AGG ACC CCG GGC GTG TGG TGG GAG
 78    Leu Tyr Leu Val Gly Phe Arg Thr Pro Gly Val Trp Trp Glu>
```

FIG. 14B

```
327  TTC GGC AAG GAC GGC GAC ACC CAC CTC CTC GGC GAC AAC CCC AGG
 93  Phe Gly Lys Asp Gly Asp Thr His Leu Leu Gly Asp Asn Pro Arg>

372  TGG CTC GGC TTC GGC AGG TAC CAG GAC CTC ATC GGC AAC AAG
108  Trp Leu Gly Phe Gly Arg Tyr Gln Asp Leu Ile Gly Asn Lys>

417  GGT CTG GAG ACC GTC ACC ATG GGC CGC GCC GAA ATG ACC AGG GCC
123  Gly Leu Glu Thr Val Thr Met Gly Arg Ala Glu Met Thr Arg Ala>

462  GTC AAC GAC CTG GCG AAG AAG AAG GCG GCT GAC CCA CAG GCC
138  Val Asn Asp Leu Ala Lys Lys Lys Ala Ala Asp Pro Gln Ala>

507  GAC ACG AAG AGC AAG CTG GTG AAG CTG GTG ATG GTG TGC GAG
153  Asp Thr Lys Ser Lys Leu Val Lys Leu Val Met Val Cys Glu>

552  GGG CTG CGG TTC AAC ACC GTG TCC CGC ACG GTG GAC GCG GGG TTC
168  Gly Leu Arg Phe Asn Thr Val Ser Arg Thr Val Asp Ala Gly Phe>

597  AAC AGC CAG CAC GGG GTG ACC TTG ACC GTG ACG CAG GGG AAG CAG
183  Asn Ser Gln His Gly Val Thr Leu Thr Val Thr Gln Gly Lys Gln>
```

FIG. 14C

```
642  GTG CAG AAG TGG GAC AGG ATC TCC AAG GCG GCC TTC GAG TGG GCT
198  Val Gln Lys Trp Asp Arg Ile Ser Lys Ala Ala Phe Glu Trp Ala>

687  GAC CAC CCC ACC GCT GTG ATC CCC GAC ATG CAG AAG CTT GGC ATC
213  Asp His Pro Thr Ala Val Ile Pro Asp Met Gln Lys Leu Gly Ile>

732  AAG GAT AAG AAC GAA GCA GCG AGG ATC GTT GCG CTC GTT AAG AAT
228  Lys Asp Lys Asn Glu Ala Ala Arg Ile Val Ala Leu Val Lys Asn>

777  CAA ACT ACT GCC GCT ACT GCT GGA TCC GCT GAT AAC AAT
243  Gln Thr Thr Ala Ala Ala Thr Ala Gly Ser Ala Asp Asn Asn>

822  TTC AAC AAA GAA CAA CAA AAT GCT TTC TAT GAA ATC TTG AAT ATG
258  Phe Asn Lys Glu Gln Gln Asn Ala Phe Tyr Glu Ile Leu Asn Met>

867  CCT AAC TTA AAC GAA GAA CAA CGC AAT GGT TTC ATC CAA AGC TTA
273  Pro Asn Leu Asn Glu Glu Gln Arg Asn Gly Phe Ile Gln Ser Leu>

912  AAA GAT GAC CCA AGC CAA AGT GCT AAC CTA TTG TCA GAA GCT AAA
288  Lys Asp Asp Pro Ser Gln Ser Ala Asn Leu Leu Ser Glu Ala Lys>
```

FIG. 14D

```
 957  AAG TTA AAT GAA TCT CAA GCA CCG AAA GAT CGA TCC GCC TGATCAA
 303  Lys Leu Asn Glu Ser Gln Ala Pro Lys Asp Arg Ser Ala End<
1003  TGCAACGACACATCATGATCTGCTGCACTTAATTACTATGTTCGTATACAAATAAA
1062  TACACCCGGCGTACGCGGTGTCCTTATATGGTCTAAAATGTAGCCAGTAAATTTAAA
1121  CTACTTTCTCGTGCCGAATTCACTGGCCCGGGCATGCTATATA
```

FIG. 15A

```
                  TCCCTCTAGATGGGCCTAATTAAGCTTAAAGGAGGAAAAAATT ATG AAA
                                                              Met Lys>

1
  1

57   AGA ATA GTG CCA AAG TTC ACT GAA ATC TTC CCC GTG GAG GAC GCG
      Arg Ile Val Pro Lys Phe Thr Glu Ile Phe Pro Val Glu Asp Ala>
  3

102   AAC TAC CCT TAC AGC GCC TTC ATC GCG TCG GTC CGG AAA GAC GTG
      Asn Tyr Pro Tyr Ser Ala Phe Ile Ala Ser Val Arg Lys Asp Val>
 18

147   ATC AAA CAC TGC ACC GAC CAT AAA GGG ATC TTC CAG CCC GTG CTG
      Ile Lys His Cys Thr Asp His Lys Gly Ile Phe Gln Pro Val Leu>
 33

192   CCA CCG GAG AAG AAG GTC CCG GAG CTA TGG TTC TAC ACA GAG CTC
      Pro Pro Glu Lys Lys Val Pro Glu Leu Trp Phe Tyr Thr Glu Leu>
 48

237   AAA ACT AGG ACC AGC TCC ATC ACG CTC GCC ATA CGC ATG GAC AAC
      Lys Thr Arg Thr Ser Ser Ile Thr Leu Ala Ile Arg Met Asp Asn>
 63

282   CTG TAC CTC GTG GGC TTC AGG ACC CCG GGC GGG GTG TGG TGG GAG
      Leu Tyr Leu Val Gly Phe Arg Thr Pro Gly Gly Val Trp Trp Glu>
 78

327   TTC GGC AAG GAC GGC GAC ACC CAC CTC GGC GAC AAC CCC AGG
      Phe Gly Lys Asp Gly Asp Thr His Leu Gly Asp Asn Pro Arg>
 93
```

FIG. 15B

```
372  TGG CTC GGC TTC GGC AGG TAC CAG GAC CTC ATC GGC AAC AAG
108  Trp Leu Gly Phe Gly Arg Tyr Gln Asp Leu Ile Gly Asn Lys>

417  GGT CTG GAG ACC GTC ACC ATG GGC CGC GAA ATG ACC AGG GCC
123  Gly Leu Glu Thr Val Thr Met Gly Arg Glu Met Thr Arg Ala>

462  GTC AAC GAC CTG GCG AAG AAG AAG GCC GCC CCA CAG GCC
138  Val Asn Asp Leu Ala Lys Lys Lys Ala Ala Asp Pro Gln Ala>

507  GAC ACG AAG AGC AAG CTG GTG AAG CTG GTC ATG GTG TGC GAG
153  Asp Thr Lys Ser Lys Leu Val Lys Leu Val Met Val Cys Glu>

552  GGG CTG CGG TTC AAC ACC GTG TCC CGC ACG GTG GAC GCG GGG TTC
168  Gly Leu Arg Phe Asn Thr Val Ser Arg Thr Val Asp Ala Gly Phe>

597  AAC AGC CAG CAC GGG GTG ACC TTG ACC GTG ACG CAG GGG AAG CAG
183  Asn Ser Gln His Gly Val Thr Leu Thr Val Thr Gln Gly Lys Gln>

642  GTG CAG AAG TGG GAC AGG ATC TCC AAG GCG GCC TTC GAG TGG GCT
198  Val Gln Lys Trp Asp Arg Ile Ser Lys Ala Ala Phe Glu Trp Ala>

687  GAC CAC CCC ACC GCT GTG ATC CCC GAC ATG CAG AAG CTT GGC ATC
213  Asp His Pro Thr Ala Val Ile Pro Asp Met Gln Lys Leu Gly Ile>
```

FIG. 15C

| | | | | | | | | | | | | | | |
|---|---|---|---|---|---|---|---|---|---|---|---|---|---|---|
| 732<br>228 | AAG<br>Lys | GAT<br>Asp | AAG<br>Lys | AAC<br>Asn | GAA<br>Glu | GCA<br>Ala | GCG<br>Ala | AGG<br>Arg | ATC<br>Ile | GTT<br>Val | GCG<br>Ala | CTC<br>Leu | GTT<br>Val | AAG<br>Lys | AAT<br>Asn> |
| 777<br>243 | CAA<br>Gln | ACT<br>Thr | ACT<br>Thr | GCC<br>Ala | GCT<br>Ala | GCC<br>Ala | GCT<br>Ala | ACT<br>Thr | GCT<br>Ala | GGA<br>Gly | TCC<br>Ser | AAA<br>Lys | CCA<br>Pro | GAA<br>Glu | GTG<br>Val> |
| 822<br>258 | ATC<br>Ile | GAT<br>Asp | GCG<br>Ala | TCT<br>Ser | GAA<br>Glu | TTA<br>Leu | ACA<br>Thr | CCA<br>Pro | GCC<br>Ala | GTG<br>Val | ACA<br>Thr | ACT<br>Thr | TAC<br>Tyr | AAA<br>Lys | CTT<br>Leu> |
| 867<br>273 | GTT<br>Val | ATT<br>Ile | AAT<br>Asn | GGT<br>Gly | AAA<br>Lys | ACA<br>Thr | TTG<br>Leu | AAA<br>Lys | GGC<br>Gly | GAA<br>Glu | ACA<br>Thr | ACT<br>Thr | ACT<br>Thr | GAA<br>Glu | GCT<br>Ala> |
| 912<br>288 | GTT<br>Val | GAT<br>Asp | GCT<br>Ala | GCT<br>Ala | ACT<br>Thr | GCA<br>Ala | GAA<br>Glu | AAA<br>Lys | GTC<br>Val | TTC<br>Phe | AAA<br>Lys | CAA<br>Gln | TAC<br>Tyr | GCT<br>Ala | AAC<br>Asn> |
| 957<br>303 | GAC<br>Asp | AAC<br>Asn | GGT<br>Gly | GTT<br>Val | GAC<br>Asp | GGT<br>Gly | GAA<br>Glu | TGG<br>Trp | ACT<br>Thr | TAC<br>Tyr | GAC<br>Asp | GAT<br>Asp | GCG<br>Ala | ACT<br>Thr | AAG<br>Lys> |
| 1002<br>318 | ACC<br>Thr | TTT<br>Phe | ACA<br>Thr | GTT<br>Val | ACT<br>Thr | GAA<br>Glu | AAA<br>Lys | CCA<br>Pro | GAA<br>Glu | GTG<br>Val | ATC<br>Ile | GAT<br>Asp | GCG<br>Ala | TCT<br>Ser | GAA<br>Glu> |
| 1047<br>333 | TTA<br>Leu | ACA<br>Thr | CCA<br>Pro | GCC<br>Ala | GTG<br>Val | ACA<br>Thr | AGA<br>Arg | TCC<br>Ser | GCT<br>Ala | GAT<br>Asp | AAC<br>Asn | AAT<br>Asn | TTC<br>Phe | AAC<br>Asn | AAA<br>Lys> |

FIG. 15D

```
1092  GAA CAA CAA AAT GCT TTC TAT GAA ATC TTG AAT ATG CCT AAC TTA
 348  Glu Gln Gln Asn Ala Phe Tyr Glu Ile Leu Asn Met Pro Asn Leu>

1137  AAC GAA GAA CAA CGC AAT GGT TTC ATC CAA AGC TTA AAA GAT GAC
 363  Asn Glu Glu Gln Arg Asn Gly Phe Ile Gln Ser Leu Lys Asp Asp>

1182  CCA AGC CAA AGT GCT AAC CTA TTG TCA GAA GCT AAA AAG TTA AAT
 378  Pro Ser Gln Ser Ala Asn Leu Leu Ser Glu Ala Lys Lys Leu Asn>

1227  GAA TCT CAA GCA CCG AAA GAT CGA TCC GCC TGATCAATGCAACGACACA
 393  Glu Ser Gln Ala Pro Lys Asp Arg Ser Ala End<

1276  TCATGATCTGCTGCTGCACTTAATTACTATGTTCGTATACAAATAAATACACCCGGCGT

1335  ACGCGGGTGTTCCTTATATGGTCTAAAATGTAGCCCAGTAAATTTTAAACTACTTTCTCGT

1394  GCCGAATTCACTGGCCCGGCATGCTATATA
```

FIG. 16A

```
1      TCCCTCTAGATGCGGGCCTAATTAAGCTTAAAAGGAGGAAAAAATT ATG AAA
1                                                     Met Lys>

57     AGA ATA GTG CCA AAG TTC ACT GAA ATC TTC CCC GTG GAG GAC GCG
1      Arg Ile Val Pro Lys Phe Thr Glu Ile Phe Pro Val Glu Asp Ala>

102    AAC TAC CCT TAC AGC GCC TTC ATC GCG TCG GTC CGG AAA GAC GTG
18     Asn Tyr Pro Tyr Ser Ala Phe Ile Ala Ser Val Arg Lys Asp Val>

147    ATC AAA CAC TGC ACC GAC CAT AAA GGG ATC TTC CAG CCC GTG CTG
33     Ile Lys His Cys Thr Asp His Lys Gly Ile Phe Gln Pro Val Leu>

192    CCA CCG GAG AAA GTC CCG GAG CTA TGG TTC TAC ACA GAG CTC
48     Pro Pro Glu Lys Val Pro Glu Leu Trp Phe Tyr Thr Glu Leu>

237    AAA ACT AGG ACC AGC TCC ATC ACG CTC GCC ATA CGC ATG GAC AAC
63     Lys Thr Arg Thr Ser Ser Ile Thr Leu Ala Ile Arg Met Asp Asn>

282    CTG TAC CTC GTG GGC TTC AGG ACC CCG GGG GTG TGG TGG GAG
78     Leu Tyr Leu Val Gly Phe Arg Thr Pro Gly Val Trp Trp Glu>

327    TTC GGC AAG GAC GGC GAC ACC CAC CTC CTC GGC GAC AAC CCC AGG
93     Phe Gly Lys Asp Gly Asp Thr His Leu Leu Gly Asp Asn Pro Arg>
```

FIG. 16B

```
372  TGG CTC GGC TTC GGC AGG TAC CAG GAC CTC ATC GGC AAC AAG
108  Trp Leu Gly Phe Gly Arg Tyr Gln Asp Leu Ile Gly Asn Lys>

417  GGT CTG GAG ACC GTC ATG ACC GTC ATG GCC GAA ATG ACC AGG GCC
123  Gly Leu Glu Thr Val Met Thr Val Met Ala Glu Met Thr Arg Ala>

462  GTC AAC GAC CTG GCG AAG AAG CTG GCG AAG AAG AAG GCT CCA CAG GCC
138  Val Asn Asp Leu Ala Lys Lys Leu Ala Lys Lys Ala Ala Pro Gln Ala>

507  GAC ACG AAG AGC AAG CTG GTG CTG GTG AAG CTG GTG GTC ATG GTG TGC GAG
153  Asp Thr Lys Ser Lys Leu Val Lys Leu Val Val Met Val Cys Glu>

552  GGG CTG CGG TTC AAC ACC GTG TCC CGC ACG GTG GAC GCG GGG TTC
168  Gly Leu Arg Phe Asn Thr Val Ser Arg Thr Val Asp Ala Gly Phe>

597  AAC AGC CAG CAC GGG GTG ACC TTG ACC GTG ACG CAG GGG AAG CAG
183  Asn Ser Gln His Gly Val Thr Leu Thr Val Thr Gln Gly Lys Gln>

642  GTG CAG AAG TGG GAC AGG ATC TCC AAG GCG GCC TTC GAG TGG GCT
198  Val Gln Lys Trp Asp Arg Ile Ser Lys Ala Ala Phe Glu Trp Ala>

687  GAC CAC CCC ACC GCT GTG ATC CCC GAC ATG CAG AAG CTT GGC ATC
213  Asp His Pro Thr Ala Val Ile Pro Asp Met Gln Lys Leu Gly Ile>
```

FIG. 16C

```
 732  AAG GAT AAG AAC GAA GCA GCG AGG ATC GTT GCG CTC GTT AAG AAT
 228  Lys Asp Lys Asn Glu Ala Ala Arg Ile Val Ala Leu Val Lys Asn>

777  CAA ACT ACT GCC GCT GCC GCT ACT GCT GGA TCC AAA CCA GAA GTG
 243  Gln Thr Thr Ala Ala Ala Ala Thr Ala Gly Ser Lys Pro Glu Val>

822  ATC GAT GCG TCT GAA TTA ACA CCA GCC GTG ACA ACT TAC AAA CTT
 258  Ile Asp Ala Ser Glu Leu Thr Pro Ala Val Thr Thr Tyr Lys Leu>

867  GTT ATT AAT GGT AAA ACA TTG AAA GGC GAA ACA ACT ACT GAA GCT
 273  Val Ile Asn Gly Lys Thr Leu Lys Gly Glu Thr Thr Thr Glu Ala>

912  GTT GAT GCT GCT ACT GCA GAA AAA GTC TTC AAA CAA TAC GCT AAC
 288  Val Asp Ala Ala Thr Ala Glu Lys Val Phe Lys Gln Tyr Ala Asn>

957  GAC AAC GGT GTT GAC GGT GAA TGG ACT TAC GAC GAT GCG ACT AAG
 303  Asp Asn Gly Val Asp Gly Glu Trp Thr Tyr Asp Asp Ala Thr Lys>

1002  ACC TTT ACA GTT ACT GAA AAA CCA GAA GTG ATC GAT GCG TCT GAA
 318  Thr Phe Thr Val Thr Glu Lys Pro Glu Val Ile Asp Ala Ser Glu>

1047  TTA ACA CCA GCC AGA TCC AAA CCA GAA GTG ATC GAT GCG
 333  Leu Thr Pro Ala Arg Ser Lys Pro Glu Val Ile Asp Ala>
```

FIG. 16D

```
1092  TCT GAA TTA ACA CCA GCC GTG ACA ACT TAC AAA CTT GTT ATT AAT
348   Ser Glu Leu Thr Pro Ala Val Thr Thr Tyr Lys Leu Val Ile Asn>

1137  GGT AAA ACA TTG AAA GGC GAA ACA ACT GAA GCT GTT GAT GCT
363   Gly Lys Thr Leu Lys Gly Glu Thr Thr Glu Ala Val Asp Ala>

1182  GCT ACT GCA GAA AAA GTC TTC AAA CAA TAC GCT AAC GAC AAC GGT
378   Ala Thr Ala Glu Lys Val Phe Lys Gln Tyr Ala Asn Asp Asn Gly>

1227  GTT GAC GGT GAA TGG ACT TAC GAC GAT GCG ACT AAG ACC TTT ACA
393   Val Asp Gly Glu Trp Thr Tyr Asp Asp Ala Thr Lys Thr Phe Thr>

1272  GTT ACT GAA AAA CCA GAA TCC GCT GAT AAC AAT TTC TCT GAA TTA ACA CCA
408   Val Thr Glu Lys Pro Glu Ser Ala Asp Asn Asn Phe Ser Glu Leu Thr Pro>

1317  GCC GTG ACA AGA TCC GCT GAT AAC AAT TTC AAC AAA GAA CAA CAA
423   Ala Val Thr Arg Ser Ala Asp Asn Asn Phe Asn Lys Glu Gln Gln>

1362  AAT GCT TTC TAT GAA ATC TTG AAT ATG CCT AAC TTA AAC GAA GAA
438   Asn Ala Phe Tyr Glu Ile Leu Asn Met Pro Asn Leu Asn Glu Glu>

1407  CAA CGC AAT GGT TTC ATC CAA AGC TTA AAA GAT GAC CCA AGC CAA
453   Gln Arg Asn Gly Phe Ile Gln Ser Leu Lys Asp Asp Pro Ser Gln>
```

FIG. 16E

```
1452  AGT GCT AAC CTA TTG TCA GAA GCT AAA AAG TTA AAT GAA TCT CAA
 468  Ser Ala Asn Leu Leu Ser Glu Ala Lys Lys Leu Asn Glu Ser Gln>

1497  GCA CCG AAA GAT CGA TCC GCC TGATCAATGCAACGACACATCATGATCTGCT
 483  Ala Pro Lys Asp Arg Ser Ala End<

1549  GCTGCACTTAATTACTATGTTCGTATACAAATAAATACACCCGGCGTACGCGGGTGTTCC

1608  TTATATGGTCTAAAATGTAGCCAGTAAATTTTAAACTACTTTCTCGTGCCGAATTCACT

1667  GGCCGGCATGCTATATA
```

FIG. 17A

```
     TCCCTCTAGATGCGGGCCTAATTAATTAAGCTTAAAAGGAGGAAAAAAATT ATG AAA AGA
                                                         Met Lys Arg 1
  1

60  ATA GTG CCA AAG TTC ACT GAA ATC TTC CCC GTG GAG GAC GCG AAC TAC
  4  Ile Val Pro Lys Phe Thr Glu Ile Phe Pro Val Glu Asp Ala Asn Tyr

108  CCT TAC AGC GCC TTC ATC GCG TCG GTC CGG AAA GAC GTG ATC AAA CAC
 20  Pro Tyr Ser Ala Phe Ile Ala Ser Val Arg Lys Asp Val Ile Lys His

156  TGC ACC GAC CAT AAA GGG ATC TTC CAG CCC CTG CCA CCG GAG AAG
 36  Cys Thr Asp His Lys Gly Ile Phe Gln Pro Val Leu Pro Pro Glu Lys

204  AAG GTC CCG GAG CTA TGG TTC TAC ACA GAG CTC AAA ACT AGG ACC AGC
 52  Lys Val Pro Glu Leu Trp Phe Tyr Thr Glu Leu Lys Thr Arg Thr Ser

252  TCC ATC ACG CTC GCC ATA CGC ATG GAC AAC CTG TAC CTC GTG GGC TTC
 68  Ser Ile Thr Leu Ala Ile Arg Met Asp Asn Leu Tyr Leu Val Gly Phe

300  AGG ACC CCG GGC GGG GTG TGG GAG TTC GGC AAG GAC GGC GAC ACC
 84  Arg Thr Pro Gly Gly Val Trp Trp Glu Phe Gly Lys Asp Gly Asp Thr
```

FIG. 17B

```
348  CAC CTC CTC GGC GAC AAC CCC AGG TGG CTC GGC TTC GGC AGG TAC
100  His Leu Leu Gly Asp Asn Pro Arg Trp Leu Gly Phe Gly Arg Tyr

396  CAG GAC CTC ATC GGC AAC AAG GGT CTG GAG ACC GTC ACC ATG GGC CGC
116  Gln Asp Leu Ile Gly Asn Lys Gly Leu Glu Thr Val Thr Met Gly Arg

444  GCC GAA ATG ACC AGG GCC GTC AAC GAC CTG GCG AAG AAG AAG GCG
132  Ala Glu Met Thr Arg Ala Val Asn Asp Leu Ala Lys Lys Lys Ala

492  GCT GAC CCA CAG GCC GAC ACG AAG AGC AAG CTG GTG AAG CTG GTG GTC
148  Ala Asp Pro Gln Ala Asp Thr Lys Ser Lys Leu Val Lys Leu Val Val

540  ATG GTG TGC GAG GGG CTG CGG TTC AAC ACC GTG TCC CGC ACG GTG GAC
164  Met Val Cys Glu Gly Leu Arg Phe Asn Thr Val Ser Arg Thr Val Asp

588  GCG GGG TTC AAC AGC CAG CAC GGG GTG ACC TTG ACC GTG ACG CAG GGG
180  Ala Gly Phe Asn Ser Gln His Gly Val Thr Leu Thr Val Thr Gln Gly

636  AAG CAG GTG CAG AAG TGG GAC AGG ATC TCC AAG GCG GCC TTC GAG TGG
196  Lys Gln Val Gln Lys Trp Asp Arg Ile Ser Lys Ala Ala Phe Glu Trp
```

FIG. 17C

```
684  GCT GAC CAC CCC ACC GCT GTG ATC CCC GAC ATG CAG AAG CTT GGC ATC
212  Ala Asp His Pro Thr Ala Val Ile Pro Asp Met Gln Lys Leu Gly Ile

732  AAG GAT AAG AAC GAA GCA GCG AGG ATC GTT GCG CTC GTT AAG AAT CAA
228  Lys Asp Lys Asn Glu Ala Ala Arg Ile Val Ala Leu Val Lys Asn Gln

Bam HI  Hpa I    Sal I   Eco RI
                           ┤      ┤        ┤       ┤
780  ACT ACT GCC GCT GCC GCT ACT GCT GGA TCC GTT AAC GTC GAC GAA TTC
244  Thr Thr Ala Ala Ala Ala Thr Ala Gly Ser Val Asn Val Asp Glu Phe

828  ACT GGC CGG CAT GCT ATA TA
260  Thr Gly Arg His Ala Ile Xxx
```

FIG. 18A

```
  1      TCCCTCTAGATGCGGCCTAATTAATTAAGCTTAAAAGGAGGAAAAAATT ATG AAA AGA
  1                                                        Met Lys Arg

60      ATA GTG CCA AAG TTC ACT GAA ATC TTC CCC GTG GAG GAC GCG AAC TAC
  4      Ile Val Pro Lys Phe Thr Glu Ile Phe Pro Val Glu Asp Ala Asn Tyr

108      CCT TAC AGC GCC TTC ATC GCG TCG GTC CGG AAA GAC GTG ATC AAA CAC
 20      Pro Tyr Ser Ala Phe Ile Ala Ser Val Arg Lys Asp Val Ile Lys His

156      TGC ACC GAC CAT AAA GGG ATC TTC CAG CCC GTG CTG CCA CCG GAG AAG
 36      Cys Thr Asp His Lys Gly Ile Phe Gln Pro Val Leu Pro Pro Glu Lys

204      AAG GTC CCG GAG CTA TGG TTC TAC ACA GAG CTC AAA ACT AGG ACC AGC
 52      Lys Val Pro Glu Leu Trp Phe Tyr Thr Glu Leu Lys Thr Arg Thr Ser

252      TCC ATC ACG CTC GCC ATA CGC ATG GAC AAC CTG TAC CTC GTG GGC TTC
 68      Ser Ile Thr Leu Ala Ile Arg Met Asp Asn Leu Tyr Leu Val Gly Phe

300      AGG ACC CCG GGC GGG GTG TGG GAG TTC GGC AAG GAC GGC AAG GAC ACC
 84      Arg Thr Pro Gly Gly Val Trp Glu Phe Gly Lys Asp Gly Lys Asp Thr
```

FIG. 18B

```
348  CAC CTC CTC GGC GAC AAC CCC AGG TGG CTC GGC TTC GGC AGG TAC
100  His Leu Leu Gly Asp Asn Pro Arg Trp Leu Gly Phe Gly Arg Tyr

396  CAG GAC CTC ATC GGC AAC AAG GGT CTG GAG ACC GTC ACC ATG GGC CGC
116  Gln Asp Leu Ile Gly Asn Lys Gly Leu Glu Thr Val Thr Met Gly Arg

444  GCC GAA ATG ACC AGG GCC GTC AAC GAC CTG GCG AAG AAG AAG GCG
132  Ala Glu Met Thr Arg Ala Val Asn Asp Leu Ala Lys Lys Lys Ala

492  GCT GAC CCA CAG GCC GAC ACG AAG AGC AAG CTG GTG AAG CTG GTC
148  Ala Asp Pro Gln Ala Asp Thr Lys Ser Lys Leu Val Lys Leu Val Val

540  ATG GTG TGC GAG GGG CTG TTC AAC ACC GTG TCC CGC ACG GTG GAC
164  Met Val Cys Glu Gly Leu Phe Asn Thr Val Ser Arg Thr Val Asp

588  GCG GGG TTC AAC AGC CAG CAC GGG GTG ACC TTG ACC GTG ACG CAG GGG
180  Ala Gly Phe Asn Ser Gln His Gly Val Thr Leu Thr Val Thr Gln Gly

636  AAG CAG GTG CAG AAG TGG GAC AGG ATC TCC AAG GCG GCC TTC GAG TGG
196  Lys Gln Val Gln Lys Trp Asp Arg Ile Ser Lys Ala Ala Phe Glu Trp
```

FIG. 18C

```
684  GCT GAC CAC CCC ACC GCT GTG ATC CCC GAC ATG CAG AAG CTT GGC ATC
212  Ala Asp His Pro Thr Ala Val Ile Pro Asp Met Gln Lys Leu Gly Ile

732  AAG GAT AAG AAC GAA GCA GCG AGG ATC GTT GCG CTC GTT AAG AAT CAA
228  Lys Asp Lys Asn Glu Ala Ala Arg Ile Val Ala Leu Val Lys Asn Gln

Bam HI     Hpa I     Sal I
780  ACT ACT GCC GCT GCC GCT ACT GGA TCC GTT AAC GTC GAC AAA CCA
244  Thr Thr Ala Ala Ala Ala Thr Gly Ser Val Asn Val Asp Lys Pro

828  GAA GTG ATC GAT GCG TCT GAA TTA ACA CCA GCC GTG ACA ACT TAC AAA
260  Glu Val Ile Asp Ala Ser Glu Leu Thr Pro Ala Val Thr Thr Tyr Lys

876  CTT GTT ATT AAT GGT AAA ACA TTG AAA GTC ACA ACT ACT GAA GCT
276  Leu Val Ile Asn Gly Lys Thr Leu Lys Val Thr Thr Thr Glu Ala

924  GTT GAT GCT GCT ACT GCA GAA AAA GTC TTC AAA CAA TAC GCT AAC GAC
292  Val Asp Ala Ala Thr Ala Glu Lys Val Phe Lys Gln Tyr Ala Asn Asp

972  AAC GGT GTT GAC GGT GAA TGG ACT TAC GAC GAT GCG ACT AAG ACC TTT
308  Asn Gly Val Asp Gly Glu Trp Thr Tyr Asp Asp Ala Thr Lys Thr Phe
```

FIG. 18D

```
1020  ACA GTT ACT GAA AAA CCA GAA GTG ATC GAT GCG TCT GAA TTA ACA CCA
324   Thr Val Thr Glu Lys Pro Glu Val Ile Asp Ala Ser Glu Leu Thr Pro

1068  GCC GTG ACA AGA TCC AAA CCA GAA GTG ATC GAT GCG TCT GAA TTA ACA
340   Ala Val Thr Arg Ser Lys Pro Glu Val Ile Asp Ala Ser Glu Leu Thr

1116  CCA GCC GTG ACA ACT TAC AAA CTT GTT ATT AAT GGT AAA ACA TTG AAA
356   Pro Ala Val Thr Thr Tyr Lys Leu Val Ile Asn Gly Lys Thr Leu Lys

1164  GGC GAA ACA ACT GAA ACT GCT GTT GAT GCT GCT ACT GCA GAA AAA GTC
372   Gly Glu Thr Thr Glu Thr Ala Val Asp Ala Ala Thr Ala Glu Lys Val

1212  TTC AAA CAA TAC GCT AAC GAC AAC GGT GTT GAC GGT GAA TGG ACT TAC
388   Phe Lys Gln Tyr Ala Asn Asp Asn Gly Val Asp Gly Glu Trp Thr Tyr

1260  GAC GAT GCG ACT AAG ACC TTT ACA GTT ACT GAA AAA CCA GAA GTG ATC
404   Asp Asp Ala Thr Lys Thr Phe Thr Val Thr Glu Lys Pro Glu Val Ile

1308  GAT GCG TCT GAA TTA ACA CCA GCC GTG ACA AGA TCC GCT GAT AAC AAT
420   Asp Ala Ser Glu Leu Thr Pro Ala Val Thr Arg Ser Ala Asp Asn Asn

1356  TTC AAC AAA GAA CAA CAA AAT GCT TTC TAT GAA ATC TTG AAT ATG CCT
436   Phe Asn Lys Glu Gln Gln Asn Ala Phe Tyr Glu Ile Leu Asn Met Pro
```

FIG. 18E

```
1404  AAC TTA AAC GAA GAA CAA CGC AAT GGT TTC ATC CAA AGC TTA AAA GAT
452   Asn Leu Asn Glu Glu Gln Arg Asn Gly Phe Ile Gln Ser Leu Lys Asp

1452  GAC CCA AGC CAA AGT GCT AAC CTA TTG TCA GAA GCT AAA AAG TTA AAT
468   Asp Pro Ser Gln Ser Ala Asn Leu Leu Ser Glu Ala Lys Lys Leu Asn

1500  GAA TCT CAA GCA CCG AAA GAT CGA TCC GCC TGA TCAATGCAACGACACATCA
484   Glu Ser Gln Ala Pro Lys Asp Arg Ser Ala End

1552  TGATCTGCTGCTGCACTTAATTACTATGTTCGTATACAAATAAATACACCCGGCGTACGCGGT

1615  GTTCCTTATATGGTCTAAAATGTAGCCAGTAAATTTTAAACTACTTTCTCGTGCCGAATTCAC

1678  TGGCCGGCATGCTATATA
```

FIG. 19A

```
1    TCCCTCTAGATGCGGGCCTAATTAATTAAGCTTAAAAGGAGGAAAAAATT ATG AAA AGA
1                                                      Met Lys Arg

60   ATA GTG CCA AAG TTC ACT GAA ATC TTC CCC GTG GAG GAC GCG AAC TAC
4    Ile Val Pro Lys Phe Thr Glu Ile Phe Pro Val Glu Asp Ala Asn Tyr

108  CCT TAC AGC GCC TTC ATC GCG TCG GTC CGG AAA GAC GTG ATC AAA CAC
20   Pro Tyr Ser Ala Phe Ile Ala Ser Val Arg Lys Asp Val Ile Lys His

156  TGC ACC GAC CAT AAA GGG ATC TTC CAG CCC CTG CCA CCG GAG AAG
36   Cys Thr Asp His Lys Gly Ile Phe Gln Pro Val Leu Pro Pro Glu Lys

204  AAG GTC CCG GAG CTA TGG TTC TAC ACA GAG CTC AAA ACT AGG ACC AGC
52   Lys Val Pro Glu Leu Trp Phe Tyr Thr Glu Leu Lys Thr Arg Thr Ser

252  TCC ATC ACG CTC GCC ATA CGC ATG GAC AAC CTG TAC CTC GTG GGC TTC
68   Ser Ile Thr Leu Ala Ile Arg Met Asp Asn Leu Tyr Leu Val Gly Phe

300  AGG ACC CCG GGC GGG GTG TGG TGG GAG TTC GGC AAG GAC GGC GAC ACC
84   Arg Thr Pro Gly Gly Val Trp Trp Glu Phe Gly Lys Asp Gly Asp Thr

348  CAC CTC CTC GGC GAC AAC CCC AGG TGG CTC GGC TTC GGC TAC AGG TAC
100  His Leu Leu Gly Asp Asn Pro Arg Trp Leu Gly Phe Gly Arg Tyr
```

FIG. 19B

| | | | | | | | | | | | | | | | |
|---|---|---|---|---|---|---|---|---|---|---|---|---|---|---|---|
| 396 | CAG | GAC | CTC | ATC | GGC | AAC | AAG | GGT | CTG | GAG | ACC | GTC | ACC | ATG | GGC | CGC |
| 116 | Gln | Asp | Leu | Ile | Gly | Asn | Lys | Gly | Leu | Glu | Thr | Val | Thr | Met | Gly | Arg |
| 444 | GCC | GAA | ATG | ACC | AGG | GCC | GTC | AAC | GAC | CTG | GCG | AAG | AAG | AAG | GCG |
| 132 | Ala | Glu | Met | Thr | Arg | Ala | Val | Asn | Asp | Leu | Ala | Lys | Lys | Lys | Ala |
| 492 | GCT | GAC | CCA | CAG | GCC | GAC | ACG | AAG | AGC | AAG | CTG | GTG | AAG | CTG | GTC |
| 148 | Ala | Asp | Pro | Gln | Ala | Asp | Thr | Lys | Ser | Lys | Leu | Val | Lys | Leu | Val |
| 540 | ATG | GTG | TGC | GAG | GGG | CTG | CGG | TTC | AAC | ACC | GTG | TCC | CGC | ACG | GTG | GAC |
| 164 | Met | Val | Cys | Glu | Gly | Leu | Arg | Phe | Asn | Thr | Val | Ser | Arg | Thr | Val | Asp |
| 588 | GCG | GGG | TTC | AAC | AGC | CAG | CAC | GGG | GTG | ACC | TTG | ACC | GTG | ACG | CAG | GGG |
| 180 | Ala | Gly | Phe | Asn | Ser | Gln | His | Gly | Val | Thr | Leu | Thr | Val | Thr | Gln | Gly |
| 636 | AAG | CAG | GTG | CAG | AAG | TGG | GAC | AGG | ATC | TCC | AAG | GCG | GCC | TTC | GAG | TGG |
| 196 | Lys | Gln | Val | Gln | Lys | Trp | Asp | Arg | Ile | Ser | Lys | Ala | Ala | Phe | Glu | Trp |
| 684 | GCT | GAC | CAC | CAC | CCC | ACC | GCT | GTG | ATC | CCC | GAC | ATG | CAG | AAG | CTT | GGC | ATC |
| 212 | Ala | Asp | His | His | Pro | Thr | Ala | Val | Ile | Pro | Asp | Met | Gln | Lys | Leu | Gly | Ile |
| 732 | AAG | GAT | AAG | AAC | GCA | GCG | AGG | ATC | GTT | GCG | CTC | GTT | AAG | AAT | CAA |
| 228 | Lys | Asp | Lys | Asn | Glu | Ala | Arg | Ile | Val | Ala | Leu | Val | Lys | Asn | Gln |

FIG. 19C

```
                                            Bam HI
                                              |
 780  ACT ACT GCC GCT GCC GCT ACT GCT GGA TCC TCT TGC GCT CGT GTC CGT
 244  Thr Thr Ala Ala Ala Ala Thr Ala Gly Ser Ser Cys Ala Arg Val Arg

Sal I
                            |
 828  CGT TCG AGC TGC GGT GTC GAC AAA CCA GAA GTG ATC GAT GCG TCT GAA
 260  Arg Ser Ser Cys Gly Val Asp Lys Pro Glu Val Ile Asp Ala Ser Glu

876  TTA ACA CCA GCC GTG ACA ACT TAC AAA CTT GTT ATT AAT GGT AAA ACA
 276  Leu Thr Pro Ala Val Thr Thr Tyr Lys Leu Val Ile Asn Gly Lys Thr

924  TTG AAA GGC GAA ACA ACT ACT ACT GAA GCT GTT GAT GCT GCT GCA GAA
 292  Leu Lys Gly Glu Thr Thr Thr Thr Glu Ala Val Asp Ala Ala Ala Glu

972  AAA GTC TTC AAA CAA TAC GCT AAC GAC AAC GGT GTT GAC GGT GAA TGG
 308  Lys Val Phe Lys Gln Tyr Ala Asn Asp Asn Gly Val Asp Gly Glu Trp

1020  ACT TAC GAC GAT GCG ACT AAG ACC TTT ACA GTT ACT GAA AAA CCA GAA
 324  Thr Tyr Asp Asp Ala Thr Lys Thr Phe Thr Val Thr Glu Lys Pro Glu

1068  GTG ATC GAT GCC TCT GAA TTA ACA CCA GCC GTG ACA AGA TCC AAA CCA
 340  Val Ile Asp Ala Ser Glu Leu Thr Pro Ala Val Thr Arg Ser Lys Pro
```

FIG. 19D

```
1116  GAA GTG ATC GAT GCG TCT GAA TTA ACA CCA GCC GTG ACA ACT TAC AAA
356   Glu Val Ile Asp Ala Ser Glu Leu Thr Pro Ala Val Thr Thr Tyr Lys

1164  CTT GTT ATT AAT GGT GCG GCT ACA TTG AAA GGC GAA ACA ACT GAA GCT
372   Leu Val Ile Asn Gly Ala Ala Thr Leu Lys Gly Glu Thr Thr Glu Ala

1212  GTT GAT GCT GCT ACT GCA GAA AAA GTC TTC AAA CAA TAC GCT AAC GAC
388   Val Asp Ala Ala Thr Ala Glu Lys Val Phe Lys Gln Tyr Ala Asn Asp

1260  AAC GGT GTT GAC GGT GAA TGG ACT TAC GAC GAT GCG ACT AAG ACC TTT
404   Asn Gly Val Asp Gly Glu Trp Thr Tyr Asp Asp Ala Thr Lys Thr Phe

1308  ACA GTT ACT GAA AAA CCA GTG ATC GAT GCG TCT GAA TTA ACA CCA
420   Thr Val Thr Glu Lys Pro Val Ile Asp Ala Ser Glu Leu Thr Pro

1356  GCC GTG ACA AGA TCC GCT GAT AAC AAT TTC AAA GAA CAA CAA AAT
436   Ala Val Thr Arg Ser Ala Asp Asn Asn Phe Lys Glu Gln Gln Asn

1404  GCT TTC TAT GAA ATC TTG AAT ATG CCT AAC TTA AAC GAA GAA CAA CGC
452   Ala Phe Tyr Glu Ile Leu Asn Met Pro Asn Leu Asn Glu Glu Gln Arg

1452  AAT GGT TTC ATC CAA AGC TTA AAA GAT GAC CCA AGC CAA AGT GCT AAC
468   Asn Gly Phe Ile Gln Ser Leu Lys Asp Asp Pro Ser Gln Ser Ala Asn
```

FIG. 19E

```
1500  CTA TTG TCA GAA GCT AAA AAG TTA AAT GAA TCT CAA GCA CCG AAA GAT
484   Leu Leu Ser Glu Ala Lys Lys Leu Asn Glu Ser Gln Ala Pro Lys Asp

1548  CGA TCC GCC TGA TCAATGCAACGACACATCATGATCTGCTGCACTTAATTACTATG
500   Arg Ser Ala End

1607  TTCGTATACAAATAAATACACCCGGGCGTACGCGGTGTTCCTTATATGGTCTAAAATGTAGCCA

1670  GTAAATTTTAAACTACTTTCTCGTGCCGAATTCACTGGCCGGGCATGCTATATA
```

RIBOSOME-INACTIVATING PROTEINS, INACTIVE PRECURSOR FORMS THEREOF, A PROCESS FOR MAKING AND A METHOD OF USING

CROSS-REFERENCE TO RELATED APPLICATION

This is a continuation of application Ser. No. 07/987,927 filed Dec. 9, 1992, now abandoned, which is a continuation-in-part application of U.S. Ser. No. 535,636 which was filed on Jun. 11, 1990 and is now U.S. Pat. No. 5,248,606.

FIELD OF THE INVENTION

The present invention relates to recombinant biology and specifically to ribosome-inactivating proteins.

BACKGROUND OF THE INVENTION

Ribosome-inactivating proteins (RIPs) are plant proteins that are capable of catalytically inactivating eukaryotic ribosomes and are consequently extremely potent inhibitors of eukaryotic protein synthesis. RIPs have been divided into two classes: type 1 and type 2 RIPs (see Barbieri and Stirpe (1982), *Cancer Surveys.*, 1:489–520). There is significant amino acid sequence homology between members of both type 1 and type 2 RIPs, and with the bacterial Shiga and Shiga-like toxins which also have the same mechanism of action (see Hovde et al. (1988), *Proc. Natl. Acad. Sci. USA,* 85:2568–2572).

Type 2 RIPs consist of two polypeptides; an RIP (or A-chain) which is covalently attached via a disulfide bond to a lectin-like protein (or B-chain). The B-chain binds to cell surface carbohydrates and facilitates subsequent cellular internalization of the RIP A-chain moiety, which results in rapid inactivation of protein synthesis and cell death. Type 2 RIPs are therefore extremely potent cytotoxins and animal poisons, the best studied example of which is ricin.

In contrast, type 1 RIPs characterized to date consist of a single polypeptide chain equivalent in activity to that of A-chain RIPs but lacking a covalently attached B-chain. Consequently, type 1 RIPs are scarcely toxic to intact cells but retain their extreme potency against cell-free protein translation systems. Typical $IC_{50}$ concentrations of type 1 RIPs are 0.5 to 10 ng/ml (0.16 to 33 pM). Until the discoveries detailed hereinbelow, reported type 1 RIPs were a remarkably homogeneous class of basic proteins with Mr values of about 30,000. Type 1 RIPs are found in a great variety of dicot and monocot plants and they may be ubiquitous. They are often abundant proteins in seeds, roots or latex for example. Their in vivo function is unclear but it has been proposed that they may be antiviral agents (see Stevens et al. (1981), *Experientia,* 37:257–259) or antifungal agents (see Roberts and Seltrennikkoff (1986), *Bioscience Reports,* 6:19–29).

To date, one article has discussed the presence of an inhibitor of animal cell-free protein synthesis in maize, as well as other cereal crops (see Coleman and Roberts (1982), *Biochimica et Biophysica Acta,* 696:239–244). The preparation of the maize inhibitor was via ammonium sulfate precipitation and phosphocellulose column chromatography. It is generally believed that the inhibitor isolated from maize was pure. The reported molecular weight of the inhibitor was 23 kiloDaltons (kD), with a reported $IC_{50}$ of 50 to 100 ng/ml in an ascites cell-free protein synthesis assay.

Where the effect of RIPs on ribosomes has been examined, both type 1 and type 2 RIPs possess a unique and highly specific N-glycosidase activity which cleaves the glycosidic bond of adenine 4324 of the rat liver ribosomal 28S RNA (see Endo (1988), In:*Immunotoxins*, Frankel (ed.), supra).

Commercial interest in RIPs has primarily focused on their use in construction of therapeutic toxins targeted to specific cells such as tumor cells by attachment of a targeting polypeptide, most frequently a monoclonal antibody (see *Immunotoxins* (1988), supra). This mimics the binding functionality of the B-chain of type 2 RIPs but replaces the non-specific action of B chains with a highly selective ligand. Another recent potential use is in HIV therapy (see U.S. Pat. No. 4,869,903 to Lifson et al., (Genelabs Incorporated and The Regents of the University of California)).

However, while a maize-derived protein synthesis inhibitor, like protein synthesis inhibitors from other Panicoideae, would appear to be useful for construction of cytotoxic conjugates, no artisan to date has reported to have successfully characterized a Panicoideae RIP. This is somewhat surprising in view of the success achieved with RIPs from non-Panicoideae plants, including cereals such as barley (see Lambert et al. (1988), In:*Immunotoxins*, supra). In part, the lack of success to date by skilled artisans in successfully utilizing the maize RIP described by Coleman and Roberts may be attributed to the fact that the protein synthesis inhibitor was relatively uncharacterized and reported $IC_{50}$ was relatively poor.

There is interest in expressing recombinant RIP in commonly employed host eukaryotic cells, because of the capacity to provide correct post-translational processing. However, as RIPs effectively inhibit protein synthesis in eukaryotic cells, a predictable problem is that heterologous expression of an RIP will result in host cell death. Thus, eukaryotic cells are generally not used as recombinant host cells. Although eukaryotic cells may be used in certain circumstances, the RIP must be constructed so as to be secreted prior to the cell experiencing toxicity (see EP 0 335 476 to Gelfand et al. (Cetus Corp.)). Therefore, prokaryotic host cells are generally used as hosts, notwithstanding disadvantages such as the inability to glycosylate and properly fold heterologously-expressed proteins.

It is thus an object of the invention to provide a method of preparing inactive forms of RIPs, in which an inactive RIP may be expressed by eukaryotic host cells and then converted to an active form.

It is yet another object of the invention to provide the DNA sequence of a gene encoding at least one inactive form of RIP, as well as expression vehicles, host cells and cell cultures containing such DNA sequence.

Other objects and advantages of the present invention will become apparent from the teachings presented hereinafter.

It is to these objects to which the present invention is directed.

SUMMARY OF THE INVENTION

In a first aspect, the present invention is directed to a substantially pure protein having an amino acid sequence effectively homologous to the amino acid sequence set forth in FIG. 1, termed a proRIP, wherein the proRIP has a selectively removable, internal peptide linker sequence and is incapable of substantially inactivating eukaryotic ribosomes, but which can be converted by removal of the linker into a protein having α and β fragments and being capable of substantially inactivating eukaryotic ribosomes, wherein the α fragment has an amino acid sequence effectively homologous to residues 17 to 161 of FIG. 1 and the β fragment has an amino acid sequence effectively homologous to residues 187 to 287 of FIG. 1.

In a second aspect, the present invention is directed to a substantially pure protein, termed a proRIP, wherein the proRIP has a selectively removable, internal peptide linker sequence and is incapable of substantially inactivating eukaryotic ribosomes, but which can be converted by removal of the linker into a protein having α and β fragments, termed an RIP, that is capable of substantially inactivating eukaryotic ribosomes, said proRIP comprising (1) a Panicoideae RIP selected from barley RIP, ricin A-chain RIP, saporin RIP, abrin A-chain RIP, SLT-1 RIP, and α-trichosanthin RIP, Luffin-A RIP, and Mirabilis antiviral protein RIP and (2) a removable, internal peptide linker sequence inserted between amino acid residues 152–162 of Ricinus communis agglutinin, amino acid residues 138–148 of Abrin-a A-chain, amino acid residues of 138–148 of Luffin-a, 139–149 of Luffin-b, amino acid residues of 138–148 Momordin, amino acid residues 139–149 of Trichosanthin, amino acid residues 151–161 of PAP-S, amino acid residues 145–155 of MAP, amino acid residues 153–163 of Saporin, amino acid residues 148–158 of Barley Translation Inhibitor and amino acid residues 174–184 of Dianthin 30.

In a third aspect, the present invention is directed to a substantially pure protein, termed an RIP, having α and β fragments and being capable of substantially inactivating eukaryotic ribosomes, wherein the α fragment has an amino acid sequence effectively homologous to residues 17 to 161 of FIG. 1 and the β fragment has an amino acid sequence effectively homologous to residues 187 to 287 of FIG. 1.

In a fourth aspect, the present invention is directed to a fusion protein capable of substantially inactivating eukaryotic ribosomes, said protein having an amino acid sequence effectively homologous to one of the amino acid sequences set forth in FIGS. 8, 10, 11, 12, 13, 14, 15, 16, 17, 18 or 19.

In a fifth aspect, the present invention is directed to a conjugate comprising a targeting vehicle and a protein, termed a proRIP, wherein the proRIP has a selectively removable, internal peptide linker sequence and is incapable of substantially inactivating eukaryotic ribosomes, but which can be converted by removal of the linker into a protein having α and β fragments and being capable of substantially inactivating eukaryotic ribosomes, wherein the α fragment has an amino acid sequence effectively homologous to residues 17 to 161 of FIG. 1 and the β fragment has an amino acid sequence effectively homologous to residues 187 to 287 of FIG. 1.

In a sixth aspect, the present invention is directed to a conjugate comprising a targeting vehicle and a fusion protein that is capable of substantially inactivating eukaryotic ribosomes, said protein having an amino acid sequence effectively homologous to an amino acid sequence set forth in FIGS. 8, 10, 11, 12, 13, 14, 15, 16, 17, 18 or 19.

In a seventh aspect, the present invention is directed to a conjugate comprising a targeting vehicle and a protein, termed a proRIP, wherein the proRIP has a selectively removable, internal peptide linker sequence and is incapable of substantially inactivating eukaryotic ribosomes, but which can be converted by removal of the linker into a protein having α and β fragments, termed an RIP, that is capable of substantially inactivating eukaryotic ribosomes, said proRIP comprising (1) a Panicoideae RIP selected from barley RIP, ricin A-chain RIP, saporin RIP, abrin A-chain RIP, SLT-1 RIP, and α-trichosanthin RIP, Luffin-A RIP, and Mirabilis antiviral protein RIP and (2) a removable, internal peptide linker sequence inserted between amino acid residues 152–162 of Ricinus communis agglutinin, amino acid residues 138–148 of Abrin-a A-chain, amino acid residues of 138–148 of Luffin-a, 139–149 of Luffin-b, amino acid residues of 138–148 Momordin, amino acid residues 139–149 of Trichosanthin, amino acid residues 151–161 of PAP-S, amino acid residues 145–155 of MAP, amino acid residues 153–163 of Saporin, amino acid residues 148–158 of Barley Translation Inhibitor and amino acid residues 174–184 of Dianthin 30.

In a eighth aspect, the present invention is directed to a method for converting a proRIP into an RIP, said method comprising the following steps:

a) providing a homogeneous protein, termed a proRIP, wherein the proRIP has a selectively removable, internal peptide linker sequence and is incapable of substantially inactivating eukaryotic ribosomes, but which can be converted by removal of the linker into a protein having α and β fragments, termed an RIP, that is capable of substantially inactivating eukaryotic ribosomes; and b) contacting the proRIP with a cleaving agent capable of deleting the linker to form a protein having α and β fragments, termed an RIP, that is capable of substantially inactivating eukaryotic ribosomes.

In a ninth aspect, the present invention is directed to DNA isolate encoding a protein, said protein having an amino acid sequence effectively homologous to the amino acid sequence set forth in FIG. 1, termed a proRIP, wherein the proRIP has a selectively removable, internal peptide linker sequence and is incapable of substantially inactivating eukaryotic ribosomes, but which can be converted by removal of the linker into a protein having α and β fragments and being capable of substantially inactivating eukaryotic ribosomes, wherein the α fragment has an amino acid sequence effectively homologous to residues 17 to 161 of FIG. 1 and the β fragment has an amino acid sequence effectively homologous to residues 187 to 287 of FIG. 1.

In a tenth aspect, the present invention is directed to a DNA sequence encoding a protein being capable of substantially inactivating eukaryotic ribosomes, said protein having an amino acid sequence effectively homologous to one of the amino acid sequences set forth in FIGS. 8, 10, 11, 12, 13, 14, 15, 16, 17, 18 or 19.

In an eleventh aspect, the present invention is directed to a DNA isolate encoding a protein, termed a proRIP, wherein the proRIP has a selectively removable, internal peptide linker sequence and is incapable of substantially inactivating eukaryotic ribosomes, but which can be converted by removal of the linker into a protein having α and β fragments, termed an RIP, that is capable of substantially inactivating eukaryotic ribosomes, said proRIP comprising (1) a Panicoideae RIP selected from barley RIP, ricin A-chain RIP, saporin RIP, abrin A-chain RIP, SLT-1 RIP, and α-trichosanthin RIP, Luffin-A RIP, and Mirabilis antiviral protein RIP and (2) a removable, internal peptide linker sequence inserted between amino acid residues 152–162 of Ricinus communis agglutinin, amino acid residues 138–148 of Abrin-a A-chain, amino acid residues of 138–148 of Luffin-a, 139–149 of Luffin-b, amino acid residues of 138–148 Momordin, amino acid residues 139–149 of Trichosanthin, amino acid residues 151–161 of PAP-S, amino acid residues 145–155 of MAP, amino acid residues 153–163 of Saporin, amino acid residues 148–158 of Barley Translation Inhibitor and amino acid residues 174–184 of Dianthin 30.

In other aspects, the invention is directed to expression vehicles capable of effecting the production of such aforementioned proteins in suitable host cells. It also includes the host cells and cell cultures which result from transformation with these expression vehicles.

BRIEF DESCRIPTION OF THE DRAWINGS

A number of aspects of the present invention are further illustrated in the accompanying Drawings, in which:

FIGS. 1a through 1c collectively depicts an intact recombinant maize proRIP nucleotide sequence (SEQ. ID. NO. 1) and amino acid sequence (SEQ. ID. NO. 2) of a protein of Mr 33,327.

FIG. 2 shows a schematic representation of the processing of maize proRIP to an active RIP.

FIG. 3 shows a comparison of the maize proRIP amino acid sequence with that of barley RIP.

FIG. 4 shows a comparison of the maize proRIP amino acid sequence with that of ricin A-chain.

FIGS. 5A shows the comparative alignment of the N-terminal amino acid sequence of an α fragment of the maize αβ RIP α fragment with the N-terminal sequences of RIPs from other sources; and FIGS. 5B shows the alignment of maize αβ RIP with regions of homology in the amino acid sequences of other RIPs.

FIGS. 7a through 7b collectively depicts a cDNA sequence of (SEQ. ID. NO. 3) the maize pro-RIP sequence engineered for expression in *Escherichia coli*.

FIGS. 8a through 8c collectively depicts a predicted DNA sequence (SEQ. ID. NO. 4) and deduced amino acid sequence (SEQ. ID. NO. 5) of R30.

FIG. 10a through 10c depicts a predicted DNA sequence (SEQ. ID. NO. 6) and deduced amino acid sequence (SEQ. ID. NO. 7) of R34-DL.

FIGS. 11a through 11c depicts a predicted DNA sequence (SEQ. ID. NO. 8) and deduced amino acid sequence (SEQ. ID. NO. 9) of R30-DL.

FIGS. 12a through 12c depicts the predicted DNA sequence (SEQ. ID. NO. 10) and deduced amino acid sequence (SEQ. ID. NO 11) for RDT.

FIGS. 13a through 13c collectively depicts the predicted DNA sequence (SEQ. ID. NO. 12) and deduced amino acid sequence (SEQ. ID. NO 13) for RDT-NP.

FIGS. 14a through 14d collectively depicts the predicted DNA sequence (SEQ. ID. NO. 14) and deduced amino acid sequence (SEQ. ID. NO 15) of RDT-A.

FIGS. 15a through 15d collectively depicts the predicted DNA sequence (SEQ. ID. NO. 16) and deduced amino acid sequence (SEQ. ID. NO 17) of RDT-G-A.

FIGS. 16a through 16e collectively depicts the predicted DNA sequence (SEQ. ID. NO. 18) and deduced amino acid sequence (SEQ. ID. NO. 19) of RDT-G-G-A.

FIGS. 17a through 17c collectively depicts the predicted DNA sequence (SEQ. ID. NO. 20) and deduced amino acid sequence (SEQ. ID. NO. 21) of RDT-BHSR.

FIGS. 18a through 18e collectively depicts the predicted DNA sequence (SEQ. ID. NO. 22) and deduced amino acid sequence (SEQ. ID. NO. 23) of RDT-BHS-GGA.

FIGS. 19a through 19e collectively depicts the predicted DNA sequence (SEQ. ID. NO 24) and deduced amino acid sequence (SEQ. ID. NO. 25) of RDT-DS-GGA.

DETAILED DESCRIPTION OF THE INVENTION

Figure 6:
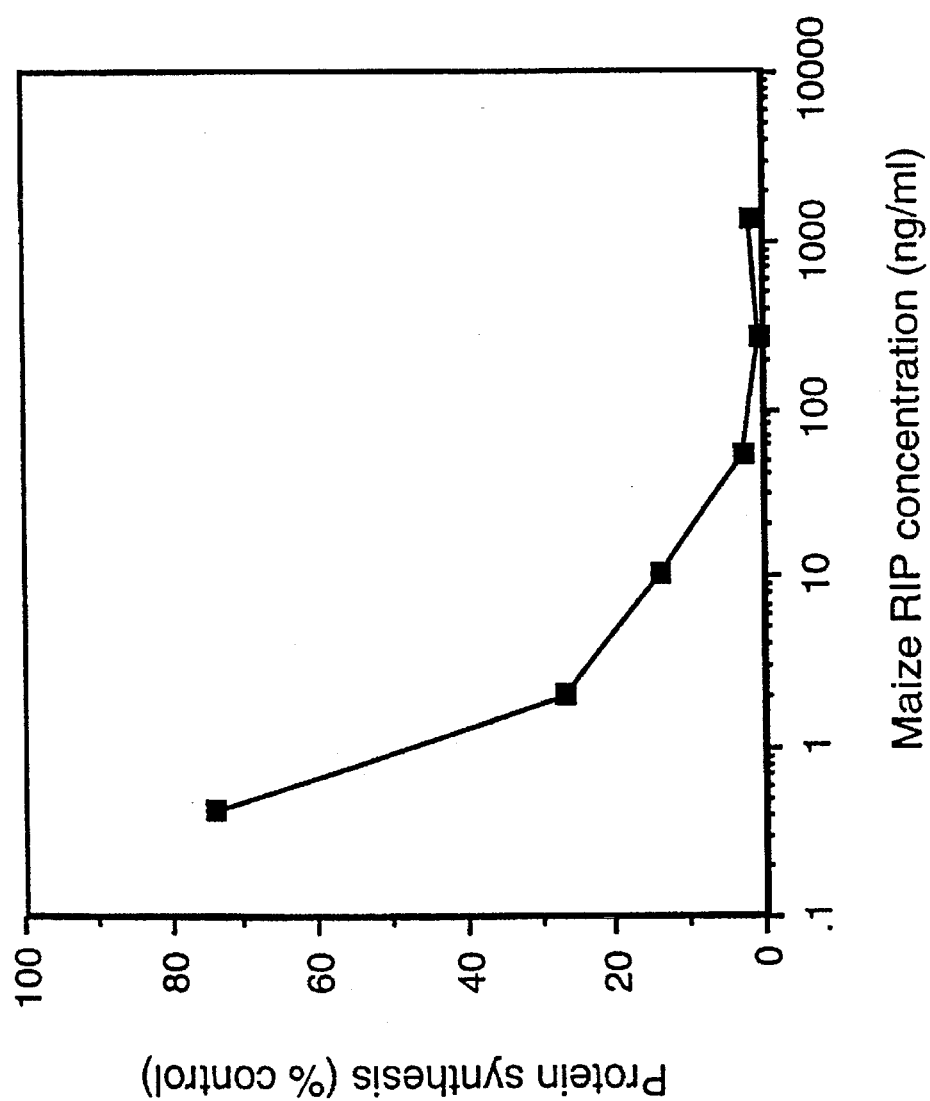
FIG. 6 shows an effect of active maize αβ RIP on mammalian cell-free protein synthesis.
Figure 9A:
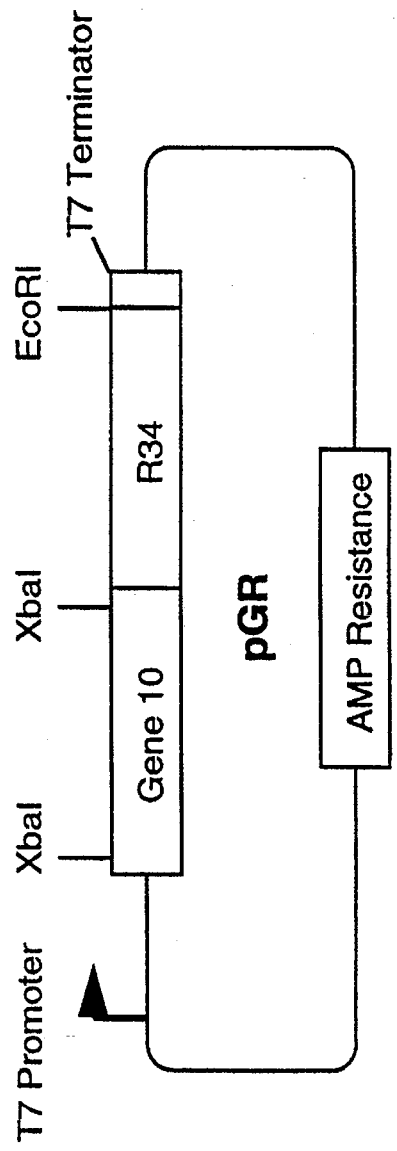
FIG. 9a shows a plasmid map of plasmid pGR and FIG. 9b shows a plasmid map of plasmid pGR1.
Figure 9B:
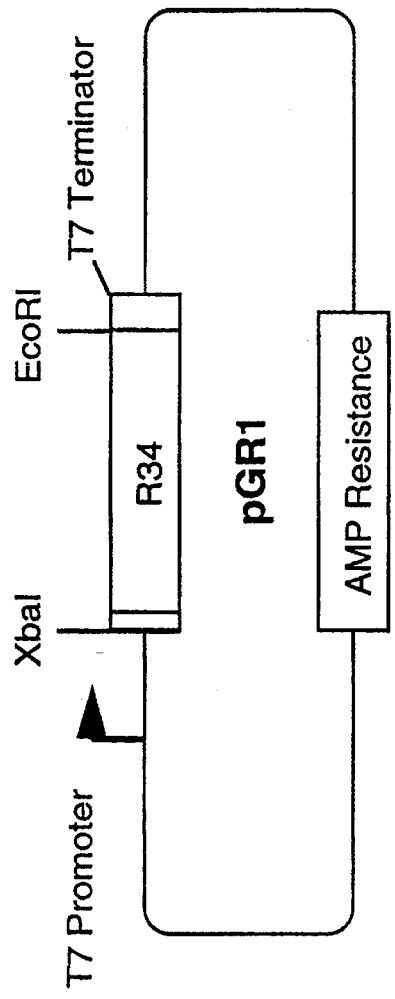

The entire teachings of all references cited herein are incorporated by reference.

Definitions

Nucleic acids, amino acids, peptides, protective groups, active groups and so on, when abbreviated, are abbreviated according to the IUPACIUB (Commission on Biological Nomenclature) or the practice in the fields concerned.

The term "proRIP" means a precursor protein that contains an amino-terminal segment, a linker and a carboxy-terminal segment and that is not capable of inactivating eukaryotic ribosomes.

The term "leader" refers to an N-terminal amino acid sequence of a proRIP that need not be present in the mature, fully active form of the αβ RIP.

The term "linker" refers to an internal amino acid sequence within a proRIP, whereby the linker is of a length and contains residues effective to render the proRIP incapable of catalytically inhibiting translation of a eukaryotic ribosome.

The term "RIP" means a protein that is capable of inactivating eukaryotic ribosomes. The term "αβ RIP" means an RIP having an α fragment, which may or may not contain a leader, and a β fragment and being capable of substantially inactivating eukaryotic ribosomes.

The term "$IC_{50}$" means the concentration of a protein necessary to inhibit protein synthesis by 50 percent in a cell-free protein synthesis assay.

The term "inhibiting amount" refers to the specific ability of RIPs to cause the death or injury of cells against which they are targeted.

The term "target cells" means those cells having ribosomes which the αβ RIP of the present invention is capable of inhibiting. The target cells may be present in living organisms or they may be preserved or maintained in vitro. The cells may be individual or associated to form an organ. Exemplary target cells include any eukaryotic cell (e.g., mammalian, insect, fungal and plant cells).

The term "targeting vehicle" means a carrier moiety containing a ligand capable of binding to a receptor of a specific cell or tissue.

"Gene" refers to the entire DNA portion involved in the synthesis of a protein. A gene embodies the structural or coding portion which begins at the 5' end from a translation start codon and extends at the 3' end to a stop codon. It also contains a promoter region, usually located 5' or upstream to the structural coding portion, which initiates and regulates the expression of a structural gene and a 3' nontranslated region downstream from the translated region.

"Expression" refers to a two-part process for the transcription and translation of a gene. The DNA defining the gene is transcribed into a precursor RNA, which is processed to its mature form, messenger RNA (mRNA). During translation, the cell's ribosomes, in conjunction with transfer RNA, translate the RNA "message" into proteins.

Preferred Embodiments of the Invention

Surprisingly, it has been discovered that studied members of Panicoideae contain αβ RIP and proRIP. Panicoideae is a subfamily of Gramineae (order) and Graminaceae (family). The subfamily Panicoideae contains three tribes: Maydeae (e.g., Tripsacum, Coix, Euchlaena and Zea), Andropogoneae (e.g., Sorghum) and Paniceae. For further taxonomic information, see Arber (1934), *The Gramineae, A Study of Cereal, Bamboo and Grass*, Cambridge University Press, p 410–411.

The present invention pertains to proteins which are derived from a plant within the subfamily Panicoideae. As taught herein, proteins obtained from various plants within the subfamily Panicoideae have shown antigenic cross reactivity (i.e., showing evidence of proRIP in Panicoideae as well as α and β fragments of an αβ RIP).

By "derived" from a plant within the subfamily Panicoideae means a protein that is effectively homologous, as defined below, with a proRIP or αβ RIP from Panicoideae, regardless of the manner in which the protein is produced. Given the present teachings it now becomes possible to prepare generally homogeneous proRIP and αβ RIP exclusive of irrelevant proteins and contaminants naturally associated therewith in the cellular environment or in extracellular fluids. For example, a substantially pure protein will show constant and reproducible characteristics within standard experimental deviations for parameters such as the following: molecular weight, chromatographic behavior, and such other parameters. The term, however, is not meant to exclude artificial or synthetic mixtures of a protein with other compounds. The term is not meant to exclude the presence of minor impurities which do not interfere with the biological activity of the protein and which may be present, for example, due to incomplete purification.

Both the proRIP and αβ RIP may be purified directly from mature and germinating seeds and developing kernels of plants within the subfamily. Generally, the purification of the Panicoideae αβ RIP and proRIP may be accomplished as set forth below.

Seeds or immature kernels of plants within the subfamily Panicoideae may be homogenized to disrupt the individual seeds or kernels. This can be accomplished by any type of commercially available homogenizer.

The Panicoideae proRIP and/or αβ RIP may be purified from the homogenization product by any appropriate protein purification technique. Exemplary techniques include gel filtration chromatographic techniques, such as conventional liquid chromatography, ion exchange chromatography, high performance liquid chromatography, and reverse phase chromatography.

Upon purification, the Panicoideae proRIP will have insignificant ribosome inactivating ability relative to its corresponding αβ RIP. For example, maize proRIP has an $IC_{50}$ of greater than about 10 micrograms per milliliter (µg/ml) in a cell-free protein synthesis assay, whereas the maize αβ RIP has an $IC_{50}$ of about 1 nanogram per milliliter (ng/ml) in a mammalian cell-free protein translation assay.

The maize proRIP has a molecular weight of about 34 kD, as determined by SDS-PAGE (see Laemmli (1970), supra), and will move as a single peak on ion exchange chromatography. Homogeneous maize αβ RIP will comprise two associated fragments, an α and β fragment, having molecular weights of approximately 16.5 kD and 11.0 kD, respectively (as determined by sodium dodecyl sulfate polyacrylamide-gel electrophoresis (SDS-PAGE), see Laemmli (1970), *Nature*, 22:680–685). The homogeneous protein will exhibit two dissociated peaks on reverse phase chromatography, and a single associated peak on ion exchange chromatography. Polyclonal antisera against each fragment both crossreact with a polypeptide present in maize kernels having a molecular weight of about 34 kD as determined by SDS-PAGE. This demonstrates that the two fragments of the maize αβ RIP are in fact derived from a common precursor (i.e., the maize proRIP).

The maize proRIP amino acid sequence (as set forth in FIG. 1) contains five sequence subsegments: (1) a leader sequence, from residues 1 to 16, (2) an α fragment, from residues 17 to 161, (3) an internal linker sequence, from residues 162 to 186, and (4) a β fragment, from residues 187 to 287 and a C-terminal segment from residues 288–301.

The net charges of these polypeptides are as follows: leader sequence –3; α fragment, +10; linker, –5; β fragment, +6 and C-terminal segment, –5. Removal of the leader and linker results in a dramatic change in net charge from the maize proRIP (+3) to maize αβ RIP (+16). Additionally, the proRIP isolated from maize has an observed pI of about 6.5 which agrees well with the value of about 6.1 derived from the deduced amino acid sequence. The pI of the active maize αβ RIP is ≧9, compared to the calculated value from the deduced amino acid sequence of about 9.06 (i.e., after deletion of the acidic leader, linker and C-terminal sequences). Thus, the maize αβ RIP has a basic pI, which is consistent with the pI of other RIPs.

When the internal linker sequence of the proRIP is removed (see FIG. 2), the αβ RIP has significant ribosome inactivating activity. The activity has been found to be significant regardless of whether the leader sequence has been removed (e.g., by recombinant methods). However, the proRIP is most active when the leader sequence is also removed and when up to fourteen C-terminus residues are also removed. In nature, it is thought that the linker is cleaved by endogenous proteases released by germinating seeds. Significantly, it has been discovered that the linker may also be cleaved in vitro by certain proteases, e.g., papain, subtilisin Carlberg to yield active maize αβ RIP from the precursor. While not intended to be bound by theory, it is thought that papain likely mimics the effect of endogenous endoproteinases released during germination.

It appears that, after removal of the internal linker, the two fragments of the processed polypeptide are held together by noncovalent forces. That is, the association of the two polypeptide chains does not depend upon interchain disulfide bonds or the formation of a peptide bond between the fragments.

Although not intended to be bound by theory, it is believed that the linker forms an external loop with exposed amino acid residues that are susceptible to proteolysis. Support for this suggestion comes from the alignment of the amino acid sequence of the maize proRIP with that of ricin A chain, the three dimensional structure of which is known (see Montfort et al. (1987), *J. Biol. Chem.*, 262:5398). The Glu 177, Arg 180, Asn 209 and Trp 211 of ricin A have been implicated in the active site region of the molecule (see Robertus (1988), In:*Immunotoxins*, supra).

Based on this alignment, homologous residues of maize αβ RIP can be positioned within the three dimensional structure of ricin A chain. The superimposed structures indicate that the C-terminal lysine of the α fragment (at residue 162) is in corresponding alignment with an externally positioned threonine (at residue 156) of the ricin A-chain. Also, the N-terminal alanine of the β fragment (at residue 187) is in corresponding alignment with an externally positioned glycine (at residue 157) of the ricin A-chain.

Any of a variety of procedures may be used to clone proRIP-encoding gene sequence. One method for cloning the proRIP gene sequence entails determining the amino acid sequence of the proRIP molecule. To accomplish this task proRIP or αβ RIP protein may be purified (as described above), and analyzed to determine the amino acid sequence of the proRIP or αβ RIP. Any method capable of elucidating such a sequence can be employed, however, Edman degradation is preferred. The use of automated sequenators is especially preferred.

It is possible to synthesize in vitro the proRIP and αβ RIP from their constituent amino acids. A suitable technique includes the solid phase method (see Merrifield (1963), *J. Amer. Chem. Soc.*, 85:2149–2154; and *Solid Phase Peptide*

*Synthesis* (1969), (eds.) Stewart and Young). Automated synthesizers are also available.

The peptides thus prepared may be isolated and purified by procedures well known in the art (see *Current Protocols in Molecular Biology* (1989), (eds.) Ausebel, et al., Vol. 1 and Sambrook et al. (1989), *Molecular Cloning: A Laboratory Manual*).

Using the amino acid sequence information, the DNA sequences capable of encoding them are examined in order to clone the gene encoding the proRIP. Because the genetic code is degenerate, more than one codon may be used to encode a particular amino acid.

Although it is possible to determine the entire amino acid sequence of the proRIP or αβ RIP, it is preferable to determine the sequence of peptide fragments of the molecule, and to use such sequence data to prepare oligonucleotide probes which can be used to isolate the entire proRIP gene sequence. The proRIP peptide fragments can be obtained by incubating the intact molecule with cyanogen bromide, or with proteases such as papain, chymotrypsin or trypsin.

Using the genetic code one or more different oligonucleotides can be identified. The probability that a particular oligonucleotide will, in fact, constitute the actual proRIP encoding sequence can be estimated by considering abnormal base pairing relationships and the frequency with which a particular codon is actually used (to encode a particular amino acid) in eukaryotic cells. Using these rules, a single oligonucleotide, or a set of oligonucleotides, that contains a theoretical "most probable" nucleotide sequence capable of encoding the proRIP or αβ RIP peptide sequences may be identified.

The oligonucleotide, or set of oligonucleotides, containing the theoretical "most probable" sequence capable of encoding the proRIP gene fragments may be used to identify the sequence of a complementary oligonucleotide, or set of oligonucleotides, which is capable of hybridizing to the "most probable" sequence, or set of sequences. An oligonucleotide containing such a complementary sequence can be employed as a probe to identify and isolate the toxin gene (see Sambrook et al. (1989), supra).

By hybridizing an oligonucleotide having a sequence complementary to the "most probable" gene sequence, one obtains a DNA molecule (or set of DNA molecules), capable of functioning as a probe to identify and isolate the proRIP gene.

The present invention also relates to DNA sequences that encode recombinant proRIP and αβ RIP. The recombinantly-produced proRIP and αβ RIP share the following properties with the proRIP and αβ RIP isolated from nature and characterized according to the teachings herein: (1) portions of the amino acid sequence deduced from the nucleotide sequence are equivalent to amino acid sequences obtained directly from nature; (2) the polypeptide is recognized by anti-RIP antibodies; (3) the molecular weight of the proRIP and αβ RIP polypeptides encoded corresponds with the naturally occurring proteins; (4) each proRIP protein is convertible to an αβ RIP; and (5) each proRIP and αβ RIP protein exhibits relatively equivalent ribosome inactivating activity.

The process for genetically engineering the proRIP or αβ RIP according to the invention is facilitated through the cloning of genetic sequences which are capable of encoding the proRIP or αβ RIP, or effectively homologous variants thereof as discussed below, and through the expression of such genetic sequences. As used herein, the term "genetic sequences" is intended to refer to a nucleic acid molecule (preferably DNA). Genetic sequences which are capable of encoding the toxin may be derived from a variety of sources. These sources include genomic DNA, cDNA, synthetic DNA, and combinations thereof.

Cells containing the desired sequence may be isolated, and genomic DNA fragmented by one or more restriction enzymes. The genomic DNA may or may not include naturally-occurring introns. The genomic DNA digested with selected restriction endonucleases yields fragments containing varying numbers of base pairs (bp).

Specifically comprehended as part of this invention are genomic DNA sequences encoding allelic variant forms of the proRIP gene which may or may not include naturally occurring introns. The allelic gene may be derived using a hybridization probe made from the DNA or RNA of the proRIP gene as well as its flanking regions. "Flanking regions" are meant to include those DNA sequences 5' and 3' of the proRIP encoding sequences.

The DNA isolate encoding the proRIP gene may also be obtained from a cDNA library. The mRNA may be isolated from a suitable source employing standard techniques of RNA isolation, and the use of oligo-dT cellulose chromatography to enrich for poly-A mRNA. A cDNA library is then prepared from the mixture of mRNA using a suitable primer, preferably a nucleic acid sequence which is characteristic of the desired cDNA. A single stranded DNA copy of the mRNA is produced using the enzyme reverse transcriptase. From the single stranded cDNA copy of the mRNA, a double-stranded cDNA molecule may be synthesized using either reverse transcriptase or DNA polymerase.

It is also possible to use primers to amplify the DNA from cells of appropriately prepared seeds and immature kernels by the polymerase chain reaction (PCR). PCR involves exponentially amplifying DNA in vitro using sequence specified oligonucleotides (see Mullis et al. (1987), *Meth. Enz.*, 155:335–350); Horton et al. (1989), *Gene*, 77:61; and *PCR Technology: Principles and Applications for DNA Amplification*, (ed.) Erlich (1989).

The DNA encoding the proRIP or αβ RIP may be chemically synthesized by manual procedures, e.g., the phosphotriester and phosphodiester methods (see Caruthers (1983), In:*Methodology of DNA and RNA*, (ed.) Weissman); or automated procedures, e.g., using diethylphosphoramidites are used as starting materials (see Beaucage et al.(1981), *Tetrahedron Letters*, 22:1859–1962). The DNA may be constructed by standard techniques of annealing and ligating fragments or by other methods.

Thereafter, the desired sequences may be isolated and purified by procedures well known in the art (see *Current Protocols in Molecular Biology* (1989), supra and Sambrook et al. (1989), *Molecular Cloning: A Laboratory Manual*, supra).

The nucleotide sequence of the maize proRIP cDNA and the deduced amino acid sequence of such the corresponding maize proRIP is set forth in FIG. 1. However, one need not be confined to the amino acid sequences of proRIP and αβ RIP found in nature. Thus, it is possible to selectively produce both proRIP and αβ RIP via the application of recombinant DNA technology. This in turn allows the production of sufficient quality and quantity of material to create novel forms of the protein unimpeded by the restriction necessarily inherent in the isolation methods involving production and extraction of the protein from natural sources.

A comparison of the maize proRIP (SEQ. ID. NO. 2) with that of barley, a monocot, is set forth in FIG. 3. The upper sequence shows maize αβ RIP (SEQ. ID. NO. 2) and the lower sequence barley RIP (SEQ. ID. NO. 26), as taught by Asano et al. (1986), *Carlsberg Res. Commun.*, 51:129. Identical residues are denoted by a solid line, conservative substitutions by a dotted line, and dashes indicate insertions to maximize homology. Residues are numbered on the left.

As set forth in FIG. 3, there is an overall homology of about 28 percent (about 34 percent including conservative substitutions) between the maize αβ RIP and barley RIP. However, the unique nature of the linker region of maize proRIP is clearly shown by the resulting gap that has been introduced in the published barley sequence to maintain homology. A lower, but significant, degree of homology is seen when the maize proRIP sequence is compared to the sequence of ricin A-chain (as set forth in FIG. 4). The upper sequence is maize αβ RIP (SEQ. ID. NO. 2) and the lower sequence is ricin A (SEQ. ID. NO. 27), as taught by Lamb et al. (1985), *Eur. J. Biochem.*, 148:265. Identical residues are denoted by a solid line and conservative substitutions by a dotted line, dashes indicate insertions to maximize homology. Residues are numbered on the left, the numbering of the ricin sequence corresponds to that of the mature protein.

As set forth in FIG. 4, a gap was again introduced in the published ricin A sequence to maximize homology corresponding to the linker region of the maize proRIP.

Further comparison of the maize proRIP sequence with published full-length sequences of other non-Panicoideae RIPs indicate that there are four regions of significant homology between these proteins (as set forth in FIGS. 5a and 5b).

FIG. 5A shows the first region and the comparative alignment of the N-terminal amino acid sequence of the maize αβ RIP residues 13 to 49 of SEQ. ID. NO. 2 a fragment with the N-terminal sequences of RIPs from other sources. The sequences are taken from: barley (residues 1 to 39 of SEQ. ID. NO. 26) (see Asano et al. (1986), supra); ricin A-chain (residues 25 to 58 of SEQ. ID. NO. 27) (see Lamb et al. (1985), supra); dodecandrin (SEQ. ID. NO. 28) (see Ready et al. (1985), *Biochem. Biophys, Acta,* 791:314); pokeweed antiviral protein 2 (SEQ. ID. NO. 29) (see Bjorn et al. (1985), *Biochem. Biophys. Acta,* 790:154); Shiga-like toxin (SEQ. ID. NO. 30) (see Calderwood et al. (1987), *Proc. Nat. Acad. Sci. USA,* 84:4364); and α-trichosanthin (SEQ. ID. NO. 31), momordins (SEQ. ID. NO. 32), bryodin (SEQ. ID. NO. 33), gelonin (SEQ. ID. NO. 34), dodecandrin, pokeweed antiviral protein-2, saporin 5 (SEQ. ID. NO. 35) and saporin 4 (SEQ. ID. NO. 36) (see Montecucchi et al. (1989), *Int. J. Peptide Res.,* 33:263). Positions showing homology in four or more sequences are noted by solid lines (showing identical residues) or dotted lines (showing conservatively substituted residues).

FIG. 5b shows that the other three regions are internally oriented. FIG. 5b specifically shows the alignment of maize αβ RIP residues 84 to 98; 201 to 215 and 237 to 247 of SEQ. ID. NO. 2 with regions of homology in the amino acid sequences of other RIPs. The sequences are available from the following references: barley residues 76 to 91; 168 to 182 and 208 to 218 of SEQ. ID. NO. 26 (see Asano et al. (1986), supra and Leah et al. (1991), *J Biol. Chem.,* 266:1564–1573); ricin A-chain (residues 70 to 84; 171 to 185 and 207 to 217 of SEQ. ID. NO. 27) (see Lamb et al. (1985), supra); abrin A-chain (SEQ. ID. NO. residues 64 to 78 are SEQ. ID. NO. 47, residues 159 to 173 are SEQ. ID. NO. 48 and residues 194 to 204 are SEQ. ID. NO. 49) (see Funatsu et al. (1988), *Agric. Biol. Chem.* 52:1095); saporin-6 (SEQ. ID. residues 62 to 76 are SEQ. ID. NO. 37, residues 170 to 184 are SEQ. ID. NO. 38 and residues 205 to 214 are SEQ. ID. NO. 46) (see Benatti et al. (1989) *Eur. J. Biochem.*, 183:465); Shiga-like toxin 1A (residues 62 to 76 are SEQ. ID. NO. 50, residues 183 to 197 are SEQ. ID. NO. 51 and residues 222 to 231 are SEQ. ID. NO. 52) (see Calderwood et al. (1987), supra); and α-trichosanthin (residues 58 to 67 are SEQ. ID. NO. 53, residues 77 to 81, residues 161 to 175 are SEQ. ID. NO. 54, residues 161 to 175, residues 196 to 207 are SEQ. ID. NO. 55, and residues 196 to 207 are SEQ. ID. NO. 56) (see Montecucchi et al. (1989), supra); Xuejun and Jiahuai (1986), *Nature,* 321:477; Chow et al. (1990), *J. Biol. Chem.,* 265:8670–8674 and Maragonore et al. (1987), *J. Biol. Chem.,* 262:11628–11633). Positions showing identity or conservative substitutions in four or more sequences are underlined, dashes indicate insertions to maximize homology. Vertical lines indicate residues that are conserved in all seven sequences. The starting amino acid of each sequence is indicated (note that trichosanthin contains an insertion sequence at residues 67 to 76).

The sequences and partial sequences of various additional Type I RIPs are set forth in the following articles: luffin-A (see Islam et al. (1990), *Agric. Biol. Chem.,* 54:2967–2978); mirabilis antiviral protein (see Habuka et al. (1989) *J. Bio. Chem.,* 264:6629–6637); trichokirin, (see Casellas et al. (1988), *Eur. J. Biochem.,* 176:581–588); momordins (see Barbieri et al. (1980), *Biochem. J.,* 186:443–452); dianthins (see Reisbig and Bruland (1983), *Arch. Biochem. Biophys.,* 224:700–706); saporins (see Maras et al., (1990), *Biochem. Intl.,* 21:831–838) and Lappi et al. (1985), *Biochem. Biophys. Res Commun.,* 129:934–942; and momorcochin-S (see Bolognesi et al. (1989), *Biochem. Biophys. Acta,* 993:287–292).

As set forth in FIG. 5b, RIPs for which a full-length sequence has been determined contain regions with significant homology. Additionally, the similarities of N-terminal sequences in an even greater number of RIPs have been compared (set forth in FIGS. 5a and 5b). It is likely that these regions have particular effect upon the function of the respective RIPs. The RIPs set forth in FIG. 5a are intended for exemplification purposes only. RIPs characterized in the future that meet the above criteria are also considered to be a part of this invention.

An RIP having a known amino acid sequences may now be altered into an inactive, proRIP form by the insertion of a linker, wherein the insertion of the linker substantially reduces the ribosome inactivating ability of the RIP. By "substantially reduce" is meant that the insertion of a cleavable linker into an active RIP lowers the $IC_{50}$ value of the resultant protein by at least 10-fold, preferably 100-fold, and more preferably 1000-fold.

Based on the information deduced from the maize system set forth herein, it now becomes possible to engineer inactive forms of any RIP having a three dimensional structure similar to the three dimensional structure of ricin A chain. Cleavage of the linker will result in an αβ RIP not heretofore found in nature.

The art has discussed the methodology for modifying the three dimensional structure of proteins (see, for example, Van Brunt (1986), *Biotechnology,* 4:277–283). The first step involves selecting plausible sites on the RIP between which the linker may be inserted. One of those sites is the exposed amino acid residues surrounding residue 156 of ricin A-chain or its equivalent in other RIP sequences. Residue 156 is located in a surface loop connecting helices D and E in the three dimensional structure of Ricin A. Thus, the present invention is intended to encompass the insertion of a peptide linker within a surface loop analogous to the surface loop of connecting helices D and E in the three dimensional structure of Ricin A, provided that the insertion of the linker substantially reduces the ribosome inactivating ability of the RIP. Specifically, in the surface loop connecting helices D and E in the three dimensional structure of Ricin A is defined by amino acids 152-162 (as published by Funatsu, et al. (1991), *Biochimie*, 73:1157-1161).

As stated previously, ricin A-chain has been shown to have sequence homology to many single chain RIPs. The present invention is intended to include the construction of αβ RIP and proRIP forms of any RIP. For example, regions in other RIPs analogous to amino acid sequence 152-162 in ricin A chain are as follows:

| RIP | Amino Acid Numbers* |
| --- | --- |
| Ricinus communis agglutinin | 152-162 |
| Abrin-a A-chain | 138-148 |
| Luffin-a | 138-148 |
| Luffin-b | 139-149 |
| Momordin | 138-148 |
| Trichosanthin | 139-149 |
| PAP-S | 151-161 |
| MAP | 145-155 |
| Saporin | 153-163 |
| Barley Translation Inhibitor | 148-158 |
| Dianthin 30 | 174-184 |

*All amino acid numbers are taken from Funatsu, et al. (1991), supra, except for the amino acid numbers for Dianthin 30, which are taken from Legname, et al. (1991), Biochimica et Biophysica Acta., 1090:119-122.

Other Type I and Type II RIPs have also been purified to homogeneity and these include; momorcharins (see Yeung et al. (1986), *Int. J. Peptide Res.*, 28:518-524); tritins (see Roberts and Stewart (1979), Biochem., 18:2615-2621); rye (see Coleman and Roberts (1982), *Biochem. Biophys. Acta*, 696:239-244); agrostins and RIPs from *Hura crepitans* (see Stirpe et al. (1983), *Biochem. J.*, 216:617-625); *Asparagus officianalis* (see Stirpe et al. (1983), *Biochem. J.*, 216:617-625); *Cucumis melo* (see Ferreras et al. (1989), *Biochem Intl.*, 19:201-207); Cucurbitaceae (see Ng et al., *Int. J. Biochem.*, 21:1353-1358); Petrocoptis (see Ferreras et al., *Cell. Molec. Biol.*, 35:89-95); volkensina (see Barbieri et al. (1984), *FEBS Lett.*, 171:277-279); viscumin-a (see Olsnes et al. (1982), *J. Biol. Chem.*, 257:123263-123270); modeccin-a (see Gasperi-Campani (1978), *Biochem. J.*, 174:491-496); *Momordia charantia* lectin-a (see Lin et al. (1978), *Linn. Toxicon.*, 16:653-660); and *Phloradendron californicum* lectin-a (see Franz et al. (1989), *FEBS lett.*, 248:115-118).

Proteins from the following other plants have also been shown to possess ribosome inactivating activity: *Stellarea holostea, Lychnis flos-cuculi, Hordeum murinum, Aegylops geniculata, Euphorbia serrata, Capsella bursapastoris, Muscari comosum* (see Merino et al. (1990), *J. Exp Botany*, 41:67-70); and proteins from *Croton tiglium* and *Jatropha curcas* (see Stirpe et al. (1976), *Biochem J.*, 156:1-6).

Recombinant procedures make possible the production of effectively homologous proteins possessing part or all of the primary structural conformation and/or one or more of the biological properties of the αβ RIP. For purpose of this investigation, an amino acid sequence is effectively homologous to a second amino acid sequence if at least 70 percent, preferably at least 80 percent, and most preferably at least 90 percent of the active portions of the amino acid sequence are identical and retains its intended function. Thus more importantly and critical to the definition, an effectively homologous sequence to the αβ RIP retains the capacity to interact with and inactivate eukaryotic ribosomes. The effectively homologous sequence to the proRIP must retain the capacity to be converted into an αβ RIP. That is, the effectively homologous proRIP must have a linker sequence which, when cleaved, will yield a biologically functional αβ RIP.

General categories of potentially-equivalent amino acids are set forth below, wherein, amino acids within a group may be substituted for other amino acids in that group: (1) glutamic acid and aspartic acid; (2) lysine, arginine and histidine; (3) hydrophobic amino acids such as alanine, valine, leucine and isoleucine; (4) asparagine and glutamine; (5) threonine and serine; (6) phenylalanine, tyrosine and tryptophan; and (7) glycine and alanine.

It is envisioned that, compared with changes to the α and β fragments, more significant changes may be made to the proRIP in the leader and linker regions. That is, since the leader and linker sequences are to be cleaved, the length and amino acid residues in their sequences may better be tolerated and considered insignificant, because it will not alter the functionality of the final product.

Thus, the linker sequence of the proRIP need not be limited to the amino acid sequence set forth in FIG. 1. Generally, the linker may be of a length, may be of an amino acid sequence, and may be internally positioned so as to substantially reduce the ribosome inactivating activity of the RIP. Obviously, since the Panicoideae linker(s) is the only known RIP linker found in nature, it is expected that such an amino acid sequence will logically be a primary candidate for insertion into other RIPs. However the present invention is intended to encompass linkers having effectively homologous sequences to a selected maize linker. The factors to be considered in synthetically preparing effectively homologous linkers for αβ RIPs generally are the same as set forth above for selecting effectively homologous linkers for a selected maize linker. For example, the length of the linker may be modified, provided that (1) the linker is cleavable, and (2) upon cleavage of the linker the resultant protein has an $IC_{50}$ value that is at least about 10 times lower than the $IC_{50}$ value of the protein containing the linker.

Primary criteria for selecting an effectively homologous linker include altering the net charge of the αβ RIP (e.g., more acidic); creating a conformational shift in the protein or providing steric hindrance to the active site of the protein.

As noted previously, the maize αβ RIP, like other RIPs, is basic. However, the maize proRIP has a slightly acidic pI. Thus, it is preferred that any effectively homologous linker selected for the maize proRIP will be acidic.

The linker should be of a length which, while capable of altering the three-dimensional structure of the protein, when cleaved will permit the protein to retain most of the three dimensional features of the active αβ RIP molecule.

To ensure that the linker is cleavable it is generally required that the conformation of the proRIP be such that the linker cleavage sites are readily accessible to a selected cleavage agent.

It is also envisioned that at least one restriction enzyme site may be engineered into the genetic sequence encoding an RIP, allowing DNA sequences encoding various polypeptide linkers to be inserted into the gene and tested for their ability to create an inactive, yet activatable RIP.

Nucleotide replacement may be achieved by the addition, deletion or substitution of various nucleotides, provided that the proper reading frame is maintained. Exemplary techniques for nucleotide replacement include polynucleotide-mediated, site-directed mutagenesis, i.e., using a single strand as a template for extension of the oligonucleotide to produce a strand containing the mutation (see Zoller et al. (1982), *Nuc. Acids Res.*, 10:6487-6500); Norris et al. (1983), *Nuc. Acids Res.*, 11:5103-5112; Zoller et al. (1984), *DNA*, 3:479-488; and Kramer et al. (1982), *Nuc. Acids Res.*, 10:6475-6485) and PCR, i.e., using sequence specified oligonucleotides to incorporate selected changes by exponentially amplifying DNA in vitro (see *PCR Technology: Principles and Applications for DNA Amplification*, Erlich, (ed.) (1989), supra; and Horton et al., supra).

Most commonly, cleavage will be effected outside of the replactive environment, for example, following harvest of microbial culture. Thus, when genetically modifying the proRIP, it may be preferable, in some instances, that the internal linker domain of the proRIP be retained, or altered so as to mimic the manner in which a natural, inactive proRIP is processed to the active $\alpha$ and $\beta$ fragments.

Any chemical or enzymatic method which recognizes a specific sequence or structure and causes an appropriate cleavage at a selected site may be utilized for the present invention. For example, it may be desirable to design carboxy termini and amino termini of the linker sequences that are subject to cleavage with selected agents. Exemplary of such sequences are Pro-Xxx-Gly-Pro (where Xxx is unspecified), which is selectively cleaved by collagenase; Ile-Glu-Gly-Arg, which is selectively cleaved by Factor Xa; and Gly-Pro-Arg, which is selectively cleaved by thrombin (see Nilsson et al. (1988), In: *Advances in Gene Technology; Protein Engineering and Production*, (ed.) Brew et al.).

A chemical or enzymatic method may not be suitable if its cleavage site occurs within the active amino acid sequences of the $\alpha$ and $\beta$ fragments. That is, cleavage within the native amino acid sequence of the $\alpha$ and $\beta$ fragments will generally have a greater likelihood of deleteriously affecting the enzymatic activity of the $\alpha\beta$ RIP. It is possible to select a specific cleavage sequence of only one amino acid residue so long as that residue does is not accessible in the amino acid sequences of the $\alpha$ and $\beta$ fragments. It is preferred, however, to utilize a specific cleavage sequence which contains two or more amino acid residues, i.e., an extended specific cleavage sequence. This type of sequence takes advantage of the extended active sites of various enzymes. Additionally, by utilizing an extended specific cleavage sequence, it is highly probable that cleavage will only occur at the desired site and not at other sites within the protein.

The cleavage techniques discussed here are by way of example and are but representative of the many variants which will occur to the skilled artisan in light of the specification.

In some instances it may prove desirable to effect cleavage of the proRIP within the cell. For examples an expression vehicle with an appropriate promoter may be provided with a DNA sequence coding for enzymes which convert the proRIP to the active form, operating in tandem with the other DNA sequence coding expression of the proRIP.

Further, as is well known, protein sequences may be modified by post-translation processing such as by becoming associated with other molecules, for example, glycosides, lipids, or such inorganic ions as phosphate. The ionization status will also vary depending on the pH of the medium or the pH at which crystallization or precipitation of the isolated form occurs. Further, the presence of air may cause oxidation of labile groups, such as —SH. Thus, included within the definition of the proRIP and αβ RIP, and fragments, thereof are all such modifications of a particular primary structure, e.g., both glycosylated and non-glycosylated forms, neutral forms, acidic and basic salts, lipid or other associated peptide forms, side chain alterations due to oxidation or derivatization, and any other such modifications of an amino acid sequence which would be encoded by the same genetic codon sequence.

By appropriate choice of restriction sites, the desired DNA fragment may be positioned in a biologically functional vector which may contain appropriate control sequences not present in the selected DNA fragment. By "biologically functional" is meant that the vector provides for replication and/or expression in an appropriate host, either by maintenance as an extrachromosomal element or by integration into the host genome. A large number of vectors are available or can be readily prepared, and are well known to skilled artisans.

In general, vectors containing the appropriate promoters, which can be used by the host organism for expression of its own protein, also contain control sequences, ribosome binding sites, and transcription termination sites. Generally, the replicon and control sequences which are derived from species compatible with the host cell are used in connection with these hosts. Finally, the vectors should desirably have a marker gene that is capable of providing a phenotypical property which allows for identification of host cells containing the vector.

When expressing the αβ RIP, the DNA fragments encoding the α fragment and the β fragment may be inserted into separate vectors, or into the same vector. Specifically, when the α and β fragments are contained in separate vectors, the host cells may be transformed via either cotransformation or targeted transformation techniques.

Construction of suitable vectors containing the desired coding and control sequences may be produced by using well-known techniques (see Sambrook et al. (1989), supra). Thereafter, the vector constructions may be used in transforming an appropriate host cell. Suitable host cells include cells derived from unicellular as well as multicellular organisms which are capable of being grown in cultures or by fermentation.

Various unicellular microorganisms can be used for both cloning and expression. Prokaryotes include members of the Enterobacteriaceae, such as strains of *Escherichia coli*, and Salmonella; Bacillaeeae, such as *Bacillus subtilis*; Pneumococcus, Streptococcus, and *Haemophilus influenzae*.

In addition to prokaryotes, eukaryotic cells may be employed. As previously stated, eukaryotic cells have not heretofore been used as recombinant host cells for RIPs. By providing inactive forms of RIPs, the present invention provides skilled artisans with the flexibility to use eukaryotic cells as recombinant hosts. By transforming eukaryotic cells with the proRIP gene, the protein may be expressed at high levels without being toxic to the host cell. Since the protein is lacking in bioactivity pending extra-cellular cleavage, the effect of expressing a proRIP to enhance the biosafety of the procedure. The proRIP may then be selectively chemically or enzymatically converted to the desired αβ RIP.

Exemplary eukaryotic microbes include yeast. *Saccharomyces cerevisae*, or common baker's yeast, is the most commonly used among eukaryotic microorganisms, although a number of other hosts are commonly available.

In addition to eukaryotic microbes, cultures of cells derived from multicellular organisms may also be used as hosts. Examples of useful host mammalian cell lines are Sp2/0, VERO and HeLa cells, Chinese hamster ovary (CHO) cell lines, and W138, BHK, COS-7 and MDCK cell lines. Other suitable hosts and expression systems are the baculovirus systems maintained in cultured insect cells, e.g., from *Spodoptera frugiperda*.

Finally, cells from and portions of higher plants have been found useful as recombinant hosts, and appropriate control sequences are available for expression in these systems. Suitable plant cells include cells derived from, or seedlings of, tobacco, petunia, tomato, potato, rice, maize and the like.

The expression vehicle may be inserted into the host cell by any suitable method. Conventional technologies for introducing biological material into living cells include electroporation (see Shigekawa and Dower (1988), *Biotechniques*, 6:742; Miller, et al. (1988), *Proc. Natl. Acad. Sci. USA*, 85:856–860; and Powell, et al (1988), *Appl. Environ. Microbiol.*, 54:655–660); direct DNA uptake mechanisms (see Mandel and Higa (1972), *J. Mol. Biol.*, 53:159–162; Dityatkin, et al. (1972), *Biochimica et Biophysica Acta*, 281:319–323; Wigler, et al. (1979), *Cell*, 16:77; and Uchimiya, et al. (1982), In: *Proc. 5th Intl. Cong. Plant Tissue and Cell Culture*, A. Fujiwara (ed.), Jap. Assoc. for Plant Tissue Culture, Tokyo, pp. 507–508); fusion mechanisms (see Uchidaz, et al. (1980), In:*Introduction of Macromolecules Into Viable Mammalian Cells*, Baserga et al. (eds.) Wistar Symposium Series, 1:169–185); infectious agents (see Fraley, et al. (1986), *CRC Crit. Rev. Plant Sci.*, 4:1–46; and Anderson (1984), *Science*, 226:401–409); microinjection mechanisms (see Crossway, et al. (1986), *Mol. Gen. Genet.*, 202:179–185); and high velocity projectile mechanisms (see EPO 0 405 696 to Miller, Schuchardt, Skokut and Gould, (DowElanco). The appropriate procedure may be chosen in accordance with the plant species used.

Generally after transformation, the host cells may be grown for about 48 hours to allow for expression of marker genes. The cells are then placed in selective medium and/or screenable media, where untransformed cells ace distinguished from transformed cells, either by death or a biochemical property. The transformed cells are grown under conditions appropriate to the production of the desired protein, and assayed for expression thereof. Exemplary assay techniques include enzyme-linked immunosorbent assay, radioimmunoassay, or fluorescence-activated cell sorter analysis, immunohistochemistry and the like. Selected positive cultures are subcloned in order to isolate pure transformed colonies. A suitable technique for obtaining subclones is via the limiting dilution method.

Uses

Essentially all of the uses that the prior art has envisioned for RIPs are intended for the novel $\alpha\beta$ RIP and proRIP set forth herein (see Immunotoxins (1988), supra; and U.S. Pat. No. 4,869,903 to Lifson et al. (Genelabs Incorporated and the Regents of the University of California)).

By providing inactive precursor forms of the $\alpha\beta$ RIP, it is now possible to provide protein synthesis inhibitors with uses in practical and improved ways not before possible. The inactive form of the $\alpha\beta$ RIP offers the additional advantage, over active RIPs, of not being active until removal of the linker sequence. Although the RIP is not toxic to the majority of mammalian cells it is known that RIP may be made specifically cytotoxic by attachment to a targeting vehicle which is capable of binding to and into target cells.

Exemplary targeting vehicles include any peptide hormone, growth factor, or other polypeptide cell recognition protein for which a specific receptor exists. A few examples include: antibodies and antibody fragments, lectins, insulin, glucagon, endorphins, growth hormone, melanocyte-stimulating hormone, transferrin, bombesin, low density lipoprotein, luteinizing hormone and asialoglycoprotein that bind selectively to target cells (see *Immunotoxins* (1988), supra). It is well established that conjugates which contain RIP exhibit maximal cytotoxicity only when the RIP moiety is released from the targeting vehicle.

Since the αβ RIP and proRIP do not contain a reactive sulfhydryl group, it may be necessary to modify the proteins using chemical crosslinking reagents in order to link such proRIP and αβ RIP to targeting vehicles.

Conjugates of a monoclonal antibody and the αβ RIP and proRIP may be made using a variety of bifunctional protein coupling agents. General examples of such reagents are N-succinimidyl-3-(2-pyridyldithio)propionate, 2-iminothiolane, bifunctional derivatives of imidoesters such as dimethyl adipimidate, active esters such as disuccinimidyl suberate, aldehydes such as glutaraldehyde, bis-azido compounds such as bis(p-diazoniumbenzoyl) ethylenediamine, diisocyanates such as toluene 2,6-diisocyanate, and bis-active fluorine compounds such as 1,5-difluoro-2,4-dinitrobenzene (see, for example, WO 86/05098). In addition, recombinant DNA methodologies may be employed to construct a cytotoxic fusion protein. For a general discussion of chimeric toxins (see, for example, Pastan and FitzGerald (1989), *The Journal of Biological Chemistry*, 264:15157–15160; and U.S. Pat. No. 4,892,827 to Pastan et al. (The United States of America as represented by the Department of Health and Human Services)).

EXAMPLES

The present invention is illustrated in further detail by the following examples. The examples are for the purposes of illustration only, and are not to be construed as limiting the scope of the present invention. All temperatures not otherwise indicated are Centigrade. All parts and percentages are by weight unless otherwise specifically noted. All DNA sequences are given in the conventional 5' to 3' direction. All amino acid sequences are given in conventional amino-terminus to carboxy-terminus direction.

Example 1

Isolation of Maize αβ RIP

All steps were performed at 4° C., except for high performance liquid chromatography (HPLC) which was performed at room temperature. Five hundred grams (500 g) of finely ground mature maize kernels were extracted for at least 2 hours and up to 24 hours (hr) with 1500 ml, 25 mM sodium phosphate, pH 7.2 (PB)+50 mM sodium chloride. After the extract was strained through several layers of cheesecloth, the protein precipitating between 55 percent and 85 percent ammonium sulfate was collected and redissolved in PB, then dialyzed overnight against the same buffer. The solution was clarified by centrifugation and applied to a 2.5×10 centimeter (cm) DE-52 cellulose column equilibrated with PB. The protein passing straight through the column was collected and applied to a Mono S 10/10 column (Pharmacia LKB Biotechnology, Piscataway, N.J.) equilibrated with PB, and eluted with a linear gradient of 0 to 200 mM sodium chloride in PB over 90 minutes at 2 milliliter/minute (ml/min). Alternatively, the protein can be precipitated with 85 percent ammonium sulfate and be dialyzed overnight before applying to the Mono S 10/10 column.

Fractions containing ribosome inactivating protein activity (as measured by rabbit reticulocyte protein synthesis assay, described below) were pooled and concentrated to 0.5 ml in Centricon-10 devices (Amicon, Danvers, Mass.), and applied to a Superose 12 column equilibrated in PB (Pharmacia LKB Biotechnology) at a flow-rate of 0.4 ml/min. Fractions containing ribosome inactivating protein activity (as measured by a rabbit reticulocyte protein synthesis assay, described below) (the first major peak) were pooled. At this stage, the αβ RIP was usually quite pure as identified by SDS-PAGE (see Laemmli (1970), supra). If necessary, further purification can be achieved by applying the protein to a Mono S 5/5 column (Pharmacia LKB Biotechnology) equilibrated with PB and eluted at 1 ml/min with 0 to 50 mM sodium chloride in PB over 5 minutes, then 50 to 200 mM sodium chloride in PB over 25 min.

Results from a typical purification are presented in Table 1. The effect of purified maize αβ RIP on mammalian protein synthesis is shown in FIG. 6.

TABLE 1

Purification of maize RIP from Mature Kernels

| Step | Protein (mg) | Total units* ×10⁶ | Yield (%) | Fold Purification | IC₅₀ (ng/ml) |
|---|---|---|---|---|---|
| Crude extract | 6816 | 384 | 100 | 1.0 | 323 |
| 85% Ammonium sulfate | 1010 | 115 | 30 | 2.0 | 161 |
| post-DE52 treatment | 428 | 144 | 38 | 5.9 | 54 |
| Mono S10/10 pool | 10.2 | 58 | 15 | 102 | 3.2 |
| Superose 12 pool | 1.8 | 33 | 8.6 | 327 | 0.99 |
| Mono S 5/5 pool | 1.32 | 32.4 | 8.4 | 436 | 0.74 |

*One unit of activity is the amount of protein required to produce 50% inhibition in the rabbit reticulocyte lysate protein synthesis assay.

A. Rabbit Reticulocyte Cell-Free Protein Synthesis Assay

The inhibitory activity of the maize αβ RIP toward mammalian protein synthesis was measured in a rabbit reticulocyte lysate system following the procedures of Pelham and Jackson (see (1976), *Eur. J. Biochem.*, 67:247–256).

A mix of the following reagents was prepared (2.5 milliliter (ml) total volume): 125 microliter (μl) 200 mM Tris-HCl, pH 7.6+40 mM magnesium acetate+1.6M potassium chloride; 12.5 μl 3 mM hemin hydrochloride in 50 percent ethylene glycol; 1.0 ml untreated rabbit reticulocyte lysate (Promega, Madison, Wis.); 1.0 ml $H_2O$; 62.5 μl amino acid mix; 125 μl 20 mM ATP+4 mM GTP; 125 μl 200 mM creatine phosphate; 50 μl 2.5 mg/ml creatine phosphokinase in 50 percent ethylene glycol. The amino acid mix contained 50 μM of each amino acid except glycine (100 μM), arginine, isoleucine, methionine and tryptophan (10 μM each) and contained no leucine. All stock solutions were previously adjusted to pH 7.5 prior to addition.

Five microliters (5 μl) of appropriate dilutions of samples to be assayed were placed in the wells of a 96-well plate and 50 μl of the mix added. After 10 minutes, 50 nanoCuries (nCi) $^{14}C$-leucine in 10 μl was added to each well. After a further 10 minutes, the reaction was quenched with 10 μl 1.5M potassium hydroxide and incubated for 45 minutes. Twenty-five microliters (25 μl) of each sample was then pipetted onto individual 2.1 cm Whatman 3 MM paper disks (Whatman, Clifton, N.J.) and after drying for 2 to 3 minutes, the disks were washed successively by swirling in a flask with 250 ml 10 percent trichloroacetic acid, 250 ml 5 percent trichloroacetic acid (twice), 125 ml ethanol, 250 ml 1:1 ethanol/acetone, and 125 ml acetone. After drying, the filters were placed into vials with 10 ml scintillation cocktail and counted.

B. Antisera and Western blot analysis:

The α and β polypeptide bands were cut from 3 millimeter (mm) SDS-PAGE gels after brief staining with Coomassie blue and were electroeluted using an electroelution device (Bio-Rad, Richmond Calif.) according to the manufacturer's directions. The polypeptide preparations were then used to immunize rabbits to yield polyclonal anti-sera (prepared by RIBI Immunochem, Montana).

Western blots from Phastgels™ reagent (Pharmacia LKB Biotechnology) were performed by removing the gel from the plastic backing and then electroblotting onto Immobilon paper (Millipore Corporation, Bedford, Mass.). Blots were developed using the maize αβ RIP primary antiserum at 1:2000 dilution and alkaline phosphatase-conjugated goat anti-rabbit secondary antibody (Bio-Rad), according to the manufacturer's instructions.

Example 2

Isolation of Maize proRIP

The polyclonal antisera against the α and β fragments were used to identify a common 34 kD precursor polypeptide in crude extracts of maize kernels (maize proRIP). The presence of the maize proRIP was monitored during subsequent purification by Western blot analysis as set forth above. All steps of the purification were performed at 4° C., except for HPLC which was performed at room temperature.

Two hundred fifty grams (250 g) of immature maize kernels were homogenized in 600 ml 25 mM sodium phosphate, pH 7.2 (PB)+5 μg/ml antipapain. After the extract was strained through several layers of cheesecloth, the protein precipitating between 45 and 80 percent ammonium sulfate was collected and redissolved in 15 ml PB, then passed over a 2.5×15 cm Sephadex G-25 column (Pharmacia LKB Biotechnology) equilibrated in PB. Fractions containing protein were pooled and diluted to ~60 ml with water. The solution was applied to a Q-Sepharose (fast-flow) column packed in a 10/10 FPLC column (Pharmacia LKB Biotechnology) equilibrated with PB, and eluted with a 0 to 300 mM NaCl gradient at 2 ml/min over 75 minutes. Fractions containing the 34 kD precursor were pooled and concentrated by a Centriprep 10 device (Amicon) to 1.5 ml. This was diluted four-fold with water and applied to a Mono Q 5/5 column (Pharmacia LKB Biotechnology) equilibrated in PB. The column was eluted with a 0 to 250 mM NaCl gradient over 60 minutes. Fractions containing the 34 kD polypeptide were pooled, concentrated to 0.5 ml and applied to a Superose 12 column (Pharmacia LKB Biotechnology) equilibrated in PB. The major peak from this column contained the 34 kD maize RIP precursor and appropriate fractions were pooled and stored at −20° C.

Example 3

PAGE Analysis of Maize αβ RIP and proRIP

SDS-PAGE was performed with a Phastsystem™ reagent (Pharmacia LKB Biotechnology) using 20 percent Phastgels™ reagent and following the manufacturer's instructions. Native PAGE was performed at pH 4.2 as described in the Phastsystem™ reagent application file no. 300, method 1 (Pharmacia LKB Biotechnology).

SDS-PAGE of highly purified, active maize αβ RIP exhibited two polypeptides: an α fragment (16.5 kD) and a β fragment (11.0 kD) under both reducing and non-reducing conditions. A single band was seen in native PAGE analysis of purified, active maize αβ RIP. The minimal Mr value of the associated, native maize αβ RIP was therefore 27.5 kD.

By SDS-PAGE, highly purified maize proRIP migrated with a value of 34 kD.

Example 4

In vitro activation of Maize proRIP by Papain

A purified sample of proRIP was incubated at 0.5 mg/ml with papain, a plant thiol protease, at 0.01 mg/ml in sodium acetate buffer, pH 6 containing 2 mM dithiothreitol. After 1 to 2 hours at room temperature, the 34 kD proRIP was digested to a stable product exhibiting a polypeptide pattern almost identical to that of native, active maize αβ RIP. There was a concomitant increase in ribosome inactivating activity in the incubation; the undigested proRIP had no ribosome inactivating activity up to 2 µg/ml, whereas papain-treated proRIP had an $IC_{50}$ of <80 ng/ml. In contrast trypsin had no effect on maize proRIP.

Example 5

Chemically-determined amino acid sequences

A. N-Terminal Amino Acid Sequences of Maize αβ RIP α fragment and β fragment.

A sample of maize αβ RIP was electrophoresced by the method of Laemmli (1970), supra) in 1.5 mm thick gels and the gel electroblotted onto Immobilon PVDF paper (Millipore) using a Transphor™ apparatus (Pharmacia LKB Biotechnology). The paper was stained briefly with Coomassie blue and the bands corresponding to the α and β kD polypeptides were cut out. These were N-terminal sequenced directly from the PVDF paper using a 470A gas phase sequencer (Applied Biosystems, Foster City, Calif.). The following data was obtained (bracketed residues denote lower confidence assignments):

N-Terminal sequence of α fragment (residues 17 to 48 of FIG. 1):
K R I V P K I T E I F P V E D A N Y P V S A F I A [G] V X K D V I An additional minor species (~20 percent of the total species) had the following N-Terminal sequence (residues 13 to 22 of FIG. 1) of:
A Q T N K [L] I V P K N-Terminal sequence (residues 187 to 215 of FIG. 1) of β fragment:
A A D P Q A D T K S X L V K L V V M V S/C E G L X F N T V S B. α fragment C-Terminal Amino Acid Sequence The carboxy-terminal amino acid sequence of the α maize αβ RIP α fragment was determined using sequencing grade carboxypeptidase P from *Penicillium japonicum* (Boehringer Mannheim, Indianapolis, Ind.). A sample of a fragment was purified by reverse-phase HPLC using a Vydac 5µ C4 4.6×30 mm RP column. The column was equilibrated with 0.1 percent trifluoroacetic acid (TFA), and eluted with 0 to 40 percent of 0.1 percent TFA+80 percent acetonitrile over 8 minutes, then 40 to 60 percent of 0.1 percent TFA+80 percent acetonitrile over 20 minutes. The β fragment eluted after 21.9 minutes and the α fragment eluted after 23.3 minutes.

A lyophilized sample of the α fragment was dissolved in 20 mM sodium acetate, pH 5.8+4M urea. The digestion mix contained the following in 0.1 ml: 1.6 µg carboxypeptidase P, 66 µg β fragment, 0.12M sodium acetate pH 4.2, 0.8M urea. After 1, 5, 15, 60, 120 and 480 minutes, duplicate 8 µl aliquots from the digestion were added to 8 µl 0.4M sodium borate, pH 10.5 and frozen on dry ice.

Amino acid analysis was performed essentially as described by Jones (1986), In: *Methods of Protein Microcharacterization* (ed.) J. E. Shively. The following sequence is obtained: $NH_2$-Asp-Leu-Ala-(Lys)n-COOH, where n=2-4. This was the carboxy terminus of the α polypeptide, therefore this and the N-terminus sequence of the β fragment define the linker region contained in the precursor (see amino acid sequence of the recombinant maize proRIP derived from cDNA in FIG. 1).

C. N-Terminal Amino Acid Sequence of Maize proRIP

No N-Terminal sequence data was obtained from a sample of the 34 kD maize proRIP indicating that this polypeptide is N-terminal blocked.

Example 6

Isolation and Characterization of cDNA for Maize proRIP
A. Isolation

Immature kernels from field grown Pioneer hybrid 3737 were harvested, shelled from the cob, and stored at −20° C. Ten grams (10 g) of kernels were frozen in liquid nitrogen for several minutes then ground to a powder in a Waring blender. The powder was suspended in 20 ml of ice cold TENS buffer (10 mM Tris pH 7.4, 1 mM EDTA, 0.5 percent SDS, 0.3M NaCl) and extracted immediately with an equal volume of phenol:chloroform-isoamyl alcohol (25:24:1) saturated with TENS buffer. The aqueous phase was collected and extracted three more times with fresh phenol mixtures.

Nucleic acids were precipitated from the aqueous phase by adjusting it to 0.3M sodium acetate pH 5.5 and adding 2.5 volumes of 100 percent ethanol. Nucleic acids were collected by centrifugation and suspended directly in 1 ml phenol-chloroform-isoamyl alcohol plus 1 ml TENS and extracted by vortexing. The nucleic acid was precipitated from the aqueous phase by ethanol precipitation as above. The precipitate was collected by centrifugation and resuspended in TE buffer (10 mM Tris pH 7.4, 1 mM EDTA). Single strand nucleic acid was precipitated by adjusting the solution to 2M LiCl and incubating for 4 to 12 hours at 4° C. Centrifugation yielded a pellet which consisted of between 2.2 to 2.5 mg of total RNA.

Poly(A)-containing RNA was enriched from the total RNA sample by using Hybond mAP™ mRNA purification affinity paper (Amersham Corporation, Arlington Heights Ill.). The supplier's protocol was followed. Typically 5 to 10 µg of poly(A) enriched RNA were recovered per milligram of total RNA.

Five micrograms (5 µg) of poly(A) enriched RNA were converted into double stranded cDNA using a cDNA Synthesis™ kit (Pharmacia LKB Biotechnology). The cDNA was ligated into the cloning vector Lambda gt11 (Stratagene Inc., La Jolla Calif.) following the supplier's instructions. Packaging of the ligated vector-insert mixture was done with the Gigapack plus packaging extract (Stratagene, Inc.) again following the supplier's protocol.

The PicoBlue Immunodetection™ kit (Stratagene, Inc.) was used to screen the Lambda gt11 maize kernel cDNA library using rabbit polyclonal antisera raised against the maize proRIP, as described above.

Positive clones were purified to homogeneity and the cDNA inserts characterized by Eco RI restriction enzyme analysis. One of the largest Eco RI-generated cDNA inserts (about 1,100 bp) was ligated into the Eco RI site of plasmid pUC19 (Bethesda Research Labs, Gaithersberg, Md.). Clones carrying the proRIP cDNA insert in both orientations were identified by restriction digestion and used for large scale plasmid purification.

B. Sequencing the maize proRIP cDNA

The nucleotide sequence of the proRIP cDNA (set forth in FIG. 1) was determined by dideoxy chain termination sequencing using the Sequenase™ DNA sequencing kit (United States Biochemical Corp., Cleveland Ohio). The double stranded pUC19-RIP was used as template following the manufacturer's instructions. The first round of sequencing was initiated by the M13/pUC forward sequencing primer (Bethesda Research Labs). Subsequent primers were derived from the sequenced maize proRIP cDNA. Both strands of the cDNA were fully sequenced at least once.

The open reading frame encoding the αβ RIP protein was confirmed by comparing the cDNA deduced amino acid sequence (set forth in FIG. 1) to the chemically determined protein sequence data.

Example 7

Determination of C-terminal Processing of Maize proRIP

Attempts at chemically determining the C-terminal sequence if the β fragment gave equivocal results, as only the only residue that could be firmly identified was alanine. However, alanine accounts for 25% of the 60 C-terminal residues of pro-RIP. The extent of C-terminal proteolytic processing of maize pro-RIP to generate αβ RIP was therefore determined by accurately establishing the molecular weight of the β fragment by electrospray mass spectrometry (ES/MS). Samples of pure β fragment were prepared by reverse-phase HPLC as described in Example 5 from three different preparations of purified αβ RIP prepared as described in Example 1. These were then subjected to ES/MS analysis at the Harvard Microchemical Facility. A value of 11,020 (±20) for the molecular mass of the β fragment was obtained. Using this accurate value, in combinations with the previously-determined N-terminal sequence of the β fragment (Example 5) and deduced amino acid sequence of the pro-RIP (Example 6), the C-terminus of the naturally-occurring β fragment was established as Ala-287. Thus, 14 residues (1,336 Daltons, residues 288-301) are removed from the C-terminus of maize proRIP during processing to generate active αβ RIP.

Example 8

Expression of Maize proRIP and Derivatives in *Escherichia coli*

Various genetic derivatives of maize proRIP may be expressed in *E. coli* and tested for ribosome inactivating activity. A summary of several constructions and their properties is given below.

A. R34 (the amino acid and nucleotide sequences of which are set forth in FIG. 7) represents the recombinant proRIP gene engineered for expression in *Escherichia coli*, which encodes a protein of Mr 33,327 and as expected is not a potent inhibitor of protein synthesis. Upon papain or subtilisin Carlsberg treatment it is processed into two associated polypeptides (of approximately 17+12 kD) by SDS Phastgel™ analysis with very potent ribosome inactivating activity. N34 (not shown) represents the native proRIP as isolated from nature.

B. R30 (the amino acid and nucleotide sequences of which are set forth in FIG. 8). R30 represents the proRIP with no N-terminal leader and no linker.

Expression of the recombinant maize proRIP in *E. coli* was accomplished by engineering the cDNA via PCR amplification. A 5' primer was synthesized which contained termination codons in all three reading frames to stop translation of vector-encoded proteins upstream of the maize proRIP cDNA. The primer also contained a Shine-Dalgarno sequence several base pairs upstream of an ATG start codon followed by 23 bases which were homologous to the maize proRIP cDNA. The 3' primer spans the 3' cDNA end-pUC19 junction (the primers were shown by the underlined regions set forth in FIG. 1). PCR amplification of the cDNA in pUC19 using the GeneAmp™ kit (Perkin Elmer-Cetus, Norwalk, Conn.) yielded a predominant amplification product of approximately 1100 base pairs, as expected.

The engineered, amplified product, was purified from an agarose gel and ligated into the filled-in Hind III site of the expression vector pGEMEX-1 (Promega Corp., Madison, Wis.) to give plasmid pGR, set forth in FIG. **9*a***.

This was transformed into *E. coli* DH5α (Bethesda Research Labs). Plasmids containing the maize proRIP cDNA were isolated by colony hybridization (see Sambrook et al., supra) with a 5' maize proRIP cDNA probe and characterized. Those containing the cDNA probe for the maize proRIP in the correct orientation were tested for expression. Plasmids were transformed into competent *E. coli* JM109(DE3) (Promega Corp., Madison, Wis.), transformed cells were grown in 15 ml cultures under ampicillin selection to an optical density at 600 nm of 0.4 to 1.0. Isopropylthio-β-galactoside (IPTG) was added to 1.3 mM to induce the production of recombinant proRIP and the cultures were grown an additional 4 hours at 37° C. The cells were collected by centrifugation and stored as a pellet at −20° C.

The protein produced from the maize proRIP cDNA was analyzed by lysing the induced cells in TE containing 1 mg/ml lysozyme 37° C. for 15 minutes. The lysate was fractionated into a crude supernatant and pellet by microcentrifugation. The fractions were analyzed by SDS-PAGE using 20 percent Phastgels™ reagent (Pharmacia LKB Biotechnology). Coomassie blue staining and Western blot analysis of the gels with anti-maize proRIP sera identified a 34 kD band which was greatly increased upon induction of the cells with IPTG. Cells not carrying the plasmid or containing the plasmid with the maize proRIP cDNA in the inverted orientation did not contain this 34 kD immunoreactive band. The majority of the recombinant maize proRIP was contained in the cellular pellet suggesting the material was insoluble under these conditions.

To test if R34 could acquire the folding pattern of N34 the pellet fraction of an induced culture was dissolved in 6M guanidine HCl and allowed to denature at room temperature for 3 hours. The material was then diluted 200-fold into ice cold TE and incubated at 4° C. overnight to allow refolding of the denatured R34. The diluted material was then concentrated by a Centricon 10 device (Amicon). To test whether refolded R34 could undergo the correct proteolytic processing to the fragmented form of the maize proRIP, the material was treated with 10 μg/ml papain for various times, and samples were analyzed by SDS-Phastgel and Western blot analysis. The R34 material was processed to a stable mixture of two immuno-reactive bands which comigrate with N34 papain-processed material indicating the correct proteolytic processing had occurred.

In an effort to simplify purification of the R34 polypeptide from induced lysates, the gone 10 coding region of the pGEMEX-1 vector was removed by cutting the maize proRIP gone-containing plasmid (pGR) with Xba I and gel purifying the vector/proRIP DNA away from the gene 10 encoding DNA. Recircularization of pGR, now minus the gone 10 coding region, resulted in a plasmid called pGR1 set forth in FIG. **9*b***.

The plasmid pGR1 was transformed into JM109(DE3) cells and tested for production of R34 following induction with IPTG. As with pGR, large amounts of R34 were identified in cellular lysates both by Western blot and Coomassie blue staining. Unlike pGR, R34 produced from pGR1 was soluble and fractionated in the supernatant of lysed cells. This soluble material was treated with papain at 10 μg/ml and the R34 produced from pGR1 was cleaved to products which comigrate with N34, papain-cleaved product. The papain-treated material inhibited translation of reticulocyte lysates at significantly higher dilutions than the untreated material, indicating that the soluble R34 was processed to an active form.

C. R34-DL represents the proRIP without the linker (the amino acid and nucleotide sequences of which are set forth in FIG. 10. The sequences encoding α and β were joined directly without intervening linker DNA, i.e., nucleotides A-520 to A-594, inclusive of the intact recombinant maize proRIP nucleotide sequence (see FIG. 1) are deleted. The R34-DL gene encoded a 30.6 kD protein which was a potent inhibitor of protein synthesis. Treatment of R34-DL with papain resulted in a 28 kD polypeptide with increased ribosome inactivating activity over the untreated molecule.

Confirmation that removal of the linker from maize proRIP activated the molecule was obtained independently through genetic engineering. The 75 bp linker encoding region of R34 (A-520 to A-594 inclusive) was deleted using PCR amplification. The new construction R34-DL joined directly, in frame, the DNA encoding both the α and β fragments.

In the pGEMEX-1 system the R34-DL gene directed the synthesis of a polypeptide approximately 30.6 kD, which was recognized by antisera specific for the maize proRIP. At high dilution, *E. coli* lysates containing R34-DL protein were potent inhibitors of protein synthesis in rabbit reticulocyte lysates, in marked contrast to *E. coli* lysates containing the R34 polypeptide.

These genetic deletion data confirm that removal of the linker served to activate the R34 (proRIP) molecule. This experiment also demonstrated that covalent linkage of the α and the β polypeptide fragments resulted in an active αβ RIP. The maize proRIP did not require a break in the polypeptide backbone for enzymatic activity, removal of the linker region was sufficient to confer potent ribosome inactivating activity.

In addition, when R34-DL lysates were treated with papain a slight decrease in the molecular weight of R34-DL protein is noted (from 30.6 kD to approximately 28 kD). The R34-DL polypeptide remained intact, that is, it was not cleaved to the characteristic maize αβ RIP α and β fragments. Associated with this small change in molecular weight was an increase in protein synthesis inhibition in the *E. coli* lysates. These data indicated that in bacterial lysates removal of the linker region activated the ribosomal inactivating activity of the protein at least 250-fold, but that additional processing from the ends of the protein increased the activity.

D. Another genetic construction was made using PCR technology to remove the leader region from R34-DL. The new construction called R30-DL (nucleotides C-40 to C-84 and A-520 to A-594), inclusive, of the intact recombinant maize proRIP nucleotide sequence are deleted) encoded a protein (approximately 29.5 kD) which was slightly smaller than R34-DL (the amino acid sequence and the nucleotide sequence of which are set forth in FIG. 11). *E. coli* lysates containing R30-DL appeared to be even more potent inhibitors of protein synthesis than R34-DL lysates. Papain treatment of R30-DL containing lysates further enhanced protein synthesis inhibiting activity. Following this treatment the R30-DL protein underwent a slight decrease in molecular weight representing processing at the ends of the polypeptide.

Example 9

Expression of a Fully-Activated Maize RIP Derivative

A segment of the R30-DL gene was deleted which encodes several acidic residues at the carboxy terminus of the protein. The deletion was accomplished using the PCR engineering methods.

A thermocycler (Perkin-Elmer Cetus, Norwalk, Conn.) was used for the indicated constructions. A typical run was a one minute denaturation step, a 2 minute annealing, and a 3 minute extension step. Temperatures used were 94° C., 37° C. or 50° C., and 72° C. respectively. Following 25 cycles the reaction was held at 72° C. for 7 minutes for extension of unfinished products.

Amplification engineering reactions were done in four separate tubes of 100 μL each. The tubes were combined following amplification. Normally 100 ng of template was included in each tube. DNA primers were synthesized on a PCR Mate or 380A DNA synthesizer (Applied Biosystems) and were purified on acrylamide gels. Fifty pmol of each primer were included in each reaction. The reaction conditions for the amplification were those recommended by Perkin Elmer Cetus (10 mM Tris-HCl pH8.3, 50 mM KCl, 1.5 mM $MgCl_2$, 0.001 percent gelatin, 200 μM dNTPs and 2.5 units of Taq DNA polymerase or AmpliTaq™ thermostable DNA polymerase).

Several methods of genetic engineering were employed to produce the genetic derivatives described below. Standard methods of DNA purification, restriction enzyme digestion, agarose gel analysis, DNA fragment isolation, ligation and transformation were employed (see *Current Protocols in Molecular Biology* (1989), supra and Sambrook et al. (1989), supra).

Enzymes used for the engineering were from one of three manufacturers (Pharmacia LKB Biotechnology; Bethesda Research Labs; or New England Biolabs, Beverly, Mass.). Buffers and protocols used were provided by the manufacturer.

Using PCR, a modified RIP fragment was amplified from an RIP plasmid template, purified, then used to replace the unmodified region in the RIP gene. All fragment replacements were done in RIP genes already inserted into a pGEMEX expression plasmid.

A pGEMEX plasmid containing R30-DL, which had the 3' half of the gene removed by Nco I and Stu I digestion followed by gel purification was used as the template for PCR. The 3' half of the RIP gene was replaced with the PCR modified fragment described below.

A 3' PCR primer was synthesized which encoded the 7 amino acid residue deletion near the carboxy terminus and introduced a new unique Bam HI site. The 5' primer directed the deletion of the αβ linker and included a Nco I site. The sequences of the 5' primer and the 3' primer for the PCR amplification of RDT are given in below.

5' Primer (SEQ. ID. NO. 39):

5'-ACC GTC ACC ATG GGC CGC GCC GAA ATG ACC AGG GCC GTC AAC GAC CTG GCG AAG AAG AAG AAG GCG GCT GAC CCA CAG GCC GAC ACG AAG AGC-3'

3' Primer (SEQ. ID. NO. 40):

5'-CGG ATC CAG CAG TAG CGG CAG CGG CAG TAG-3'

The primers were used to amplify a modified DNA fragment from a pGEMEX R34-DL template. The amplified fragment was phenol extracted and ethanol precipitated. The insert DNA was cut with Nco I and ligated into the pGEMEX-R30-DL vector.

The new RIP gene derivative is designated RDT and encodes a protein of predicted a 28,233 Daltons and pI of ~9.5. The RDT gene encodes a protein with a truncated leader, deleted linker and truncated carboxy terminus.

The predicted DNA sequence and deduced amino acid sequence for RDT is shown in FIG. 12.

The RDT gene, expressed in *E. coli* using the pGEMEX system described above, was purified from bacterial lysates to apparent homogeneity. RDT protein appears to be a more potent inhibitor of protein synthesis than R30-DL. Using the reticulocyte lysate protein synthesis assay, purified RDT has a $IC_{50}$ value of 1 ng/ml.

Example 10

Modification of RDT for Fusion to Other Polypeptides

RDT was further engineered to produce another gene called RDT-NP. This construction differs from RDT in having two unique restriction sites engineered into the gene. The sites were introduced using PCR methods described in Example 9. The PCR primer was designed such that it included the desired change and a unique restriction site in the maize RIP DNA sequence. A 99 bp primer was developed to introduce the Not I and Pst I sites at the 3' end of the primer and had to be built back to the unique Nco I site for cloning purposes. The sequences of the 5' primer and 3' primer for the PCR amplification are shown below 5' Primer (SEQ. ID. NO. 41):

5'-ACC GTC ACC ATG GGC CGC GCC GAA ATG ACC AGG GCC GTC AAC GAC CTG GCG AAG AAG AAG AAG GCG GCC GCC GCT GCA GAC CCA CAG GCC GAC ACG AAG-3'

3' Primer (SEQ. ID. NO. 42):

5'-CAT GCC GGC CAG TGA ATT CGG-3'

The restriction sites (Not I and Pst I) correspond to the site of the alpha/beta linker insertion in the RIP polypeptide. RDT-NP allows DNA segments encoding various polypeptide linkers to be inserted into the gene and tested for their ability to create an inactive, yet protease activatable RIP. The predicted DNA sequence and deduced amino acid sequence for RDT-NP is shown in FIG. 13.

The RDT-NP polypeptide had a predicted molecular weight of 28,446 Daltons and pI of 9.5. Crude lysates of E. coli expressing RDT-NP from a pGEMEX vector are potent inhibitors of eukaryotic protein synthesis.

Example 11

Maize RIP Fused to a Protein A Antibody-binding Domain

To create an RIP molecule which would bind to immunoglobulin IgG, a single Antibody Binding Region (ABR) domain from the Staphylococcus aureus antibody binding Protein A was subcloned from the plasmid pRIT5 (Pharmacia LKB Biotechnology) using PCR techniques. The antibody binding domain of protein A (ABR-A) was PCR engineered to have a Bam HI site at its 5' end and a Bgl II site at it's 3' end. This allowed insertion of the ABR-A domain into the RDT Bam HI site while retaining the unique Bam HI site. The predicted DNA sequence and deduced amino acid sequence of RDT-A is shown in FIG. 14.

RDT-A was expressed in E. coli cells using the pGEMEX system. The resulting polypeptide had a predicted molecular weight of 35,198 Daltons and pI of 9.2. It was recognized by antisera to both protein A and maize RIP indicating the chimeric nature of the protein. Crude lysates of bacteria expressing RDT-A had potent eukaryotic protein synthesis inhibition activity.

RDT-A was shown to bind specifically to IgG Sepharose (Pharmacia LKB Biotechnology) following the manufacturer's instructions. Binding was best at pH 7.0. When washed at pH 5.0 the chimeric protein was released in small but detectable quantities from the resin. RDT alone does not bind to the gel.

Example 12

Maize RIP-fused to Protein A and Protein G Antibody-binding Domain

To increase the binding ability of the RDT-A to IgG antibodies the Antibody Binding Domain from Streptococcal Group G protein G (ABR-G) was synthesized using oligonucleotides. The sequence synthesized was that of the naturally occurring sequence described by Guss et al. ((1986), EMBO Journal, 5:1567–1575). The only change was the addition of Bam HI and Bgl II sites at the 5' and 3' ends respectively of the synthetic DNA.

The ABR-G fragment was inserted into the Bam HI site of RDT-A. Two classes of clones have been studied. RDT-G-A contains a single ABR-G domain inserted in the correct orientation between the 3' end of RDT and the 5' end of ABR-A. A second class contains two properly oriented ABR-G domains. The predicted DNA sequence and deduced amino acid sequence for RDT-G-A are shown in FIG. 15; and the predicted nucleotide sequence and deduced amino acid sequence for RDT-G-G-A are shown in FIG. 16.

When these genes were expressed in E. coli using the pGEMEX system the expected chimeric proteins were produced. The RDT-G-A produced a protein of predicted molecular weight 44,576 Daltons (pI 7.2). RDT-G-G-A produced a slightly larger polypeptide predicted to be 53,955 Daltons with a predicted pI of 5.4.

Crude bacterial lysates of cells expressing RDT-G-A or RDT-G-G-A were potent inhibitors or eukaryotic protein synthesis in the rabbit reticulocyte assay described in Example 2. Papain treatment of the lysates further increases activity. Analysis of the papain treated lysates indicates that the intact RDT domain is released from the ABR domains.

Both RDT-G-A and RDT-G-G-A bind tightly to IgG Sepharose (Pharmacia LKB Biotechnology). Binding is stable at pH 5.0 Elution was accomplished with 0.5M ammonium acetate pH 3.5 or by boiling the resin in SDS.

Example 13

Introduction of a Disulfide-containing, Proteolytically-sensitive Linker Peptide between RDT and Antibody-binding Domains The maize RIP (RDT) antibody binding domain (GGA) fusions described above (see Examples 11 and 12) have been shown to have both RIP and antibody binding activity. A third component was added to the constructions which would allow separation of the domains following proteolysis with trypsin and reduction with reducing agents. This was accomplished by inserting a segment of DNA between the RDT and GGA domains which encodes a protein with two cysteine residues. The cysteine residues form a disulfide bond with a 7 amino acid loop. The resulting disulfide bonded loop contains the recognition sequence for the protease trypsin. Completion of this construction required several steps as indicated below.

A. Construction of RDT-BHSR

To simplify the insertion of sequences between the RDT and GGA domains in the gene RDT-GGA, two restriction sites were added. This was done by cutting the plasmid containing RDT-GGA with the enzymes Bam HI and Eco RI. The GGA encoding region was removed from the plasmid and replaced with the synthetic oligonucleotide linker shown below (the top nucleotide sequence is SEQ. ID. NO. 43 and the bottom nucleotide sequence is SEQ. ID. NO. 45).

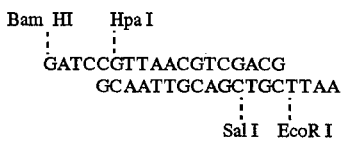

The linker restores the Bam HI and Eco RI sites while adding Hpa I and Sal I sites. The resulting construction RDT-BHSR (the predicted nucleotide sequence and deduced amino acid sequence is shown in FIG. 17).

B. Construction of RDT-BHSR-GGA

A Sal I site was placed on the end of the GGA domains by PCR amplification of the segment using the primer shown below (SEQ. ID. NO 44):

and a 3' primer which primes downstream of the Eco RI site. Following amplification, the PCR product was cut with Sal I and Eco RI and ligated into the Sal I and Eco RI sites of RDT-BHSR to create a new construction called RDT-BHSR-GGA (the predicted nucleotide sequence and deduced amino acid sequence is shown in FIG. 18).

C. Construction of RDT-DS-GGA

A linker was designed and synthesized which encodes a trypsin cleavage site flanked by two cysteine residues. The cysteine residues were expected to form a disulfide bond under appropriate conditions. The predicted nucleotide and deduced amino acid sequence for the DS linker (the top nucleotide sequence is SEQ. ID. NO. 57, the bottom nucleotide sequence is SEQ. ID. NO. 58 and the amino acid sequence is SEQ. ID. NO. 59) is set forth below:

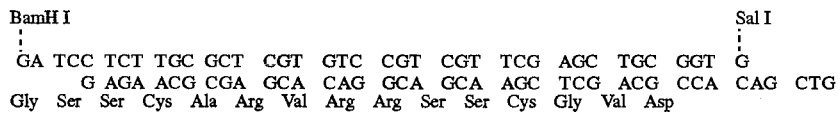

The gene RDT-BHSR-GGA was cut with Bam HI and Sal I and the synthetic double stranded oligonucleotide as shown below was ligated into the gene to create RDT-DS-GGA (see FIG. 19 for the predicted DNA sequence and deduced amino acid sequence of RDT-BHSR-GGA).

The gene RDT-DS-GGA was expressed in E. coli using the T7 expression system and purified on an IgG Sepharose column as described below.

D. Expression in *Escherichia coli* of RDT-DS-GGA using the T7 System

The expression system used was based on the T7 system as described by Moffat and Studier ("Use of T7 RNA Polymerase to Direct Expression of Cloned Genes", F. W. Studier et al. (1990), *Methods in Enzymology* 185:60–89). The expression strain JM109(DE3) is lysogenic for the T7 RNA polymerase gene under lac promoter control. Typically, JM109(DE3) (Genotype: recA1, endoA1, gyrA96, thi-, hsdR17, supE44, relA1, D(lac, pro), F' traD36 proAB lacIq, lacZ DM15: DE3, Promega, Madison Wis.) was transformed with the RDT-DS-GGA expression plasmid the night before an expression experiment. The freshly transformed cells were harvested from plates and transferred to Luria Broth (5×107 cells/ml). The culture was shaken vigorously at 37° C. for 30–60 minutes then induced with 1–10 mM IPTG. The cultures were harvested 3 hours following induction by centrifugation. Cell pellets were stored at −20° C.

Cell pellets were subjected to two freeze thaw cycles before being suspended in 1/5 volume lysis buffer (10 mM Tris pH 8.0, 1 mM EDTA, 150 mM NaCl, 0.1% Triton X-100, 1 mg/ml Lysozyme, 100 µg/ml DNase and 100 pg/ml RNase). The cells were allowed to incubate in lysis buffer 15 minutes at 37° C. The extract was fractionated by centrifugation at 4000× G for 10 minutes at room temperature. The supernatant was collected and stored at −20° C. for purification.

E. Purification

A 5 ml column of IgG Sepharose 6FF (Pharmacia, Piscataway N.J.) was prepared as directed by manufacturer's instructions. The column was equiliberated in TST (50 mM Tris pH 7.5, 150 mM NaCl, 0.05% Tween 20).

The lysate was mixed with an equal volume of TST containing protease inhibitors (100 uM antipain and 2 mM PMSF, Sigma Chemical, St Louis, Mo.) and applied to the column. The column was washed with 5–10 volumes TST. Elution of bound material was with 2 column volumes 0.5M NaAcetate pH 3.5. After elution the sample was dialyzed against 4 liters 20 mM Tris pH 8.0, 100 mM NaCl, 2 mM EDTA overnight 4° C. The affinity purified RDT-DS-GGA was concentrated in a Centriprep 30 concentrating unit. SDS Polyacrylamide gel analysis of the purified RDT-DS-GGA protein indicated it was greater than 95% pure. The material ran as a single band at approximately 55 kD.

F. Trypsin Treatment of RDT-DS-GGA

The purified RDT-DS-GGA was treated with sequencing grade trypsin (Boehringer Mannheim, Indianapolis Ind.) at a 1:100 (wt:wt) ratio 35° C. for 2 minutes (50 mM Tris pH 8.0, 2 mM CaCl$_2$). The reaction was stopped by adding a 10× weight excess of soybean trypsin inhibitor (Sigma Chemical, St Louis, Mo.).

G. Characterization of RDT-DS-GGA

Analysis of trypsin treated RDT-DS-GGA was done using 20% Phast Gels (Pharmacia, Piscataway N.J.) with or without reducing agents in the sample buffer. Under oxidizing conditions untreated RDT-DS-GGA migrates at approximately 55 kD whereas trypsin-treated RDT-DS-GGA migrates at approximately 42 kD. We have shown that RDT alone is not cleaved by trypsin under these conditions and therefore conclude that the 42 kD polypeptide is a result of trypsin cleavage within the GGA domains. When analyzed under reducing conditions the 42 kD polypeptide splits into a major band at 28 kD (co-migrating with RDT) and some smaller molecular weight fragments. The 28 kD band is recognized by anti-maize RIP antibodies. These data indicate that the engineered trypsin site between the RDT and GGA domains is clipped by trypsin and the domains are held together via a disulfide bond. These observations were confirmed by testing RDT-BHSR-GGA under the same conditions. When treated with trypsin RDT-BHSR-GGA produces a 42 kD species which is stable under reducing conditions.

Trypsin treated RDT-DS-GGA is quantitatively retained by a IgG-Sepharose column indicating that the trypsin truncated fusion protein binds IgG. When the column is eluted with reducing agent (TST with 10 mM DTT) a single 28 kD band is quantitatively eluted. The band is recognized by maize RIP antibodies and has potent RIP activity.

Example 14

Detection of Maize proRIP and αβ RIP Homologs in Panicodeae.
A. Immunological Detection Se

| | | | | | | | | | | | | | | | | |
|---|---|---|---|---|---|---|---|---|---|---|---|---|---|---|---|---|
| GCG | TCG | GTC | CGG | AAA | GAC | GTG | ATC | AAA | CAC | TGC | ACC | GAC | CAT | AAA | GGG | 195 |
| Ala | Ser | Val | Arg | Lys | Asp | Val | Ile | Lys | His | Cys | Thr | Asp | His | Lys | Gly | |
| | | | | 45 | | | | | 50 | | | | | 55 | | |
| ATC | TTC | CAG | CCC | GTG | CTG | CCA | CCG | GAG | AAG | AAG | GTC | CCG | GAG | CTA | TGG | 243 |
| Ile | Phe | Gln | Pro | Val | Leu | Pro | Pro | Glu | Lys | Lys | Val | Pro | Glu | Leu | Trp | |
| | | | 60 | | | | | 65 | | | | | 70 | | | |
| TTC | TAC | ACA | GAG | CTC | AAA | ACT | AGG | ACC | AGC | TCC | ATC | ACG | CTC | GCC | ATA | 291 |
| Phe | Tyr | Thr | Glu | Leu | Lys | Thr | Arg | Thr | Ser | Ser | Ile | Thr | Leu | Ala | Ile | |
| | | 75 | | | | | 80 | | | | | 85 | | | | |
| CGC | ATG | GAC | AAC | CTG | TAC | CTC | GTG | GGC | TTC | AGG | ACC | CCG | GGC | GGG | GTG | 339 |
| Arg | Met | Asp | Asn | Leu | Tyr | Leu | Val | Gly | Phe | Arg | Thr | Pro | Gly | Gly | Val | |
| | 90 | | | | | 95 | | | | | 100 | | | | | |
| TGG | TGG | GAG | TTC | GGC | AAG | GAC | GGC | GAC | ACC | CAC | CTC | CTC | GGC | GAC | AAC | 387 |
| Trp | Trp | Glu | Phe | Gly | Lys | Asp | Gly | Asp | Thr | His | Leu | Leu | Gly | Asp | Asn | |
| 105 | | | | | 110 | | | | | 115 | | | | | 120 | |
| CCC | AGG | TGG | CTC | GGC | TTC | GGC | GGC | AGG | TAC | CAG | GAC | CTC | ATC | GGC | AAC | 435 |
| Pro | Arg | Trp | Leu | Gly | Phe | Gly | Gly | Arg | Tyr | Gln | Asp | Leu | Ile | Gly | Asn | |
| | | | | 125 | | | | | 130 | | | | | 135 | | |
| AAG | GGT | CTG | GAG | ACC | GTC | ACC | ATG | GGC | CGC | GCC | GAA | ATG | ACC | AGG | GCC | 483 |
| Lys | Gly | Leu | Glu | Thr | Val | Thr | Met | Gly | Arg | Ala | Glu | Met | Thr | Arg | Ala | |
| | | | 140 | | | | | 145 | | | | | 150 | | | |
| GTC | AAC | GAC | CTG | GCG | AAG | AAG | AAG | AAG | ATG | GCG | ACA | CTG | GAG | GAG | GAG | 531 |
| Val | Asn | Asp | Leu | Ala | Lys | Lys | Lys | Lys | Met | Ala | Thr | Leu | Glu | Glu | Glu | |
| | | 155 | | | | | 160 | | | | | 165 | | | | |
| GAG | GTG | AAG | ATG | CAG | ATG | CAG | ATG | CCG | GAG | GCC | GCT | GAT | CTG | GCG | GCG | 579 |
| Glu | Val | Lys | Met | Gln | Met | Gln | Met | Pro | Glu | Ala | Ala | Asp | Leu | Ala | Ala | |
| | 170 | | | | | 175 | | | | | 180 | | | | | |
| GCG | GCA | GCG | GCT | GAC | CCA | CAG | GCC | GAC | ACG | AAG | AGC | AAG | CTG | GTG | AAG | 627 |
| Ala | Ala | Ala | Ala | Asp | Pro | Gln | Ala | Asp | Thr | Lys | Ser | Lys | Leu | Val | Lys | |
| 185 | | | | | 190 | | | | | 195 | | | | | 200 | |
| CTG | GTG | GTC | ATG | GTG | TGC | GAG | GGG | CTG | CGG | TTC | AAC | ACC | GTG | TCC | CGC | 675 |
| Leu | Val | Val | Met | Val | Cys | Glu | Gly | Leu | Arg | Phe | Asn | Thr | Val | Ser | Arg | |
| | | | | 205 | | | | | 210 | | | | | 215 | | |
| ACG | GTG | GAC | GCG | GGG | TTC | AAC | AGC | CAG | CAC | GGG | GTG | ACC | TTG | ACC | GTG | 723 |
| Thr | Val | Asp | Ala | Gly | Phe | Asn | Ser | Gln | His | Gly | Val | Thr | Leu | Thr | Val | |
| | | | 220 | | | | | 225 | | | | | 230 | | | |
| ACG | CAG | GGG | AAG | CAG | GTG | CAG | AAG | TGG | GAC | AGG | ATC | TCC | AAG | GCG | GCC | 771 |
| Thr | Gln | Gly | Lys | Gln | Val | Gln | Lys | Trp | Asp | Arg | Ile | Ser | Lys | Ala | Ala | |
| | | 235 | | | | | 240 | | | | | 245 | | | | |
| TTC | GAG | TGG | GCT | GAC | CAC | CCC | ACC | GCT | GTG | ATC | CCC | GAC | ATG | CAG | AAG | 819 |
| Phe | Glu | Trp | Ala | Asp | His | Pro | Thr | Ala | Val | Ile | Pro | Asp | Met | Gln | Lys | |
| | 250 | | | | | 255 | | | | | 260 | | | | | |
| CTT | GGC | ATC | AAG | GAT | AAG | AAC | GAA | GCA | GCG | AGG | ATC | GTT | GCG | CTC | GTT | 867 |
| Leu | Gly | Ile | Lys | Asp | Lys | Asn | Glu | Ala | Ala | Arg | Ile | Val | Ala | Leu | Val | |
| 265 | | | | | 270 | | | | | 275 | | | | | 280 | |
| AAG | AAT | CAA | ACT | ACT | GCC | GCT | GCC | GCT | ACT | GCT | GCC | AGT | GCT | GAC | AAC | 915 |
| Lys | Asn | Gln | Thr | Thr | Ala | Ala | Ala | Ala | Thr | Ala | Ala | Ser | Ala | Asp | Asn | |
| | | | | 285 | | | | | 290 | | | | | 295 | | |
| GAC | GAC | GAC | GAG | GCC | TGATCAATGC | AACGACACAT | CATGATCTGC | TGCTGCACTT | | | | | | | | 970 |
| Asp | Asp | Asp | Glu | Ala | | | | | | | | | | | | |
| | | | 300 | | | | | | | | | | | | | |

AATTACTATG TTCGTATACA AATAAATACA CCCGGCGTAC GCGGTGTTCC TTATATGGTC   1030

TAAAATGTAG CCAGTAAATT TTAAACTACT TTCTCGTGCC GAATTC   1076

( 2 ) INFORMATION FOR SEQ ID NO:2:

( i ) SEQUENCE CHARACTERISTICS:
        ( A ) LENGTH: 301 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Glu | Ile | Thr | Leu | Glu | Pro | Ser | Asp | Leu | Met | Ala | Gln | Thr | Asn |
|---|---|---|---|---|---|---|---|---|---|---|---|---|---|---|---|
| 1 | | | | 5 | | | | | 10 | | | | | 15 | |

| Lys | Arg | Ile | Val | Pro | Lys | Phe | Thr | Glu | Ile | Phe | Pro | Val | Glu | Asp | Ala |
|---|---|---|---|---|---|---|---|---|---|---|---|---|---|---|---|
| | | | 20 | | | | | 25 | | | | | 30 | | |

| Asn | Tyr | Pro | Tyr | Ser | Ala | Phe | Ile | Ala | Ser | Val | Arg | Lys | Asp | Val | Ile |
|---|---|---|---|---|---|---|---|---|---|---|---|---|---|---|---|
| | | 35 | | | | | 40 | | | | | 45 | | | |

| Lys | His | Cys | Thr | Asp | His | Lys | Gly | Ile | Phe | Gln | Pro | Val | Leu | Pro | Pro |
|---|---|---|---|---|---|---|---|---|---|---|---|---|---|---|---|
| | 50 | | | | | 55 | | | | | 60 | | | | |

| Glu | Lys | Lys | Val | Pro | Glu | Leu | Trp | Phe | Tyr | Thr | Glu | Leu | Lys | Thr | Arg |
|---|---|---|---|---|---|---|---|---|---|---|---|---|---|---|---|
| 65 | | | | | 70 | | | | | 75 | | | | | 80 |

| Thr | Ser | Ser | Ile | Thr | Leu | Ala | Ile | Arg | Met | Asp | Asn | Leu | Tyr | Leu | Val |
|---|---|---|---|---|---|---|---|---|---|---|---|---|---|---|---|
| | | | | 85 | | | | | 90 | | | | | 95 | |

| Gly | Phe | Arg | Thr | Pro | Gly | Gly | Val | Trp | Trp | Glu | Phe | Gly | Lys | Asp | Gly |
|---|---|---|---|---|---|---|---|---|---|---|---|---|---|---|---|
| | | | 100 | | | | | 105 | | | | | 110 | | |

| Asp | Thr | His | Leu | Leu | Gly | Asp | Asn | Pro | Arg | Trp | Leu | Gly | Phe | Gly | Gly |
|---|---|---|---|---|---|---|---|---|---|---|---|---|---|---|---|
| | | 115 | | | | | 120 | | | | | 125 | | | |

| Arg | Tyr | Gln | Asp | Leu | Ile | Gly | Asn | Lys | Gly | Leu | Glu | Thr | Val | Thr | Met |
|---|---|---|---|---|---|---|---|---|---|---|---|---|---|---|---|
| | 130 | | | | | 135 | | | | | 140 | | | | |

| Gly | Arg | Ala | Glu | Met | Thr | Arg | Ala | Val | Asn | Asp | Leu | Ala | Lys | Lys | Lys |
|---|---|---|---|---|---|---|---|---|---|---|---|---|---|---|---|
| 145 | | | | | 150 | | | | | 155 | | | | | 160 |

| Lys | Met | Ala | Thr | Leu | Glu | Glu | Glu | Val | Lys | Met | Gln | Met | Gln | Met |
|---|---|---|---|---|---|---|---|---|---|---|---|---|---|---|
| | | | | 165 | | | | | 170 | | | | | 175 |

| Pro | Glu | Ala | Ala | Asp | Leu | Ala | Ala | Ala | Ala | Ala | Asp | Pro | Gln | Ala |
|---|---|---|---|---|---|---|---|---|---|---|---|---|---|---|
| | | | 180 | | | | | 185 | | | | | 190 | |

| Asp | Thr | Lys | Ser | Lys | Leu | Val | Lys | Leu | Val | Val | Met | Val | Cys | Glu | Gly |
|---|---|---|---|---|---|---|---|---|---|---|---|---|---|---|---|
| | | 195 | | | | | 200 | | | | | 205 | | | |

| Leu | Arg | Phe | Asn | Thr | Val | Ser | Arg | Thr | Val | Asp | Ala | Gly | Phe | Asn | Ser |
|---|---|---|---|---|---|---|---|---|---|---|---|---|---|---|---|
| | 210 | | | | | 215 | | | | | 220 | | | | |

| Gln | His | Gly | Val | Thr | Leu | Thr | Val | Thr | Gln | Gly | Lys | Gln | Val | Gln | Lys |
|---|---|---|---|---|---|---|---|---|---|---|---|---|---|---|---|
| 225 | | | | | 230 | | | | | 235 | | | | | 240 |

| Trp | Asp | Arg | Ile | Ser | Lys | Ala | Ala | Phe | Glu | Trp | Ala | Asp | His | Pro | Thr |
|---|---|---|---|---|---|---|---|---|---|---|---|---|---|---|---|
| | | | | 245 | | | | | 250 | | | | | 255 | |

| Ala | Val | Ile | Pro | Asp | Met | Gln | Lys | Leu | Gly | Ile | Lys | Asp | Lys | Asn | Glu |
|---|---|---|---|---|---|---|---|---|---|---|---|---|---|---|---|
| | | | 260 | | | | | 265 | | | | | 270 | | |

| Ala | Ala | Arg | Ile | Val | Ala | Leu | Val | Lys | Asn | Gln | Thr | Thr | Ala | Ala | Ala |
|---|---|---|---|---|---|---|---|---|---|---|---|---|---|---|---|
| | | 275 | | | | | 280 | | | | | 285 | | | |

| Ala | Thr | Ala | Ala | Ser | Ala | Asp | Asn | Asp | Asp | Asp | Glu | Ala |
|---|---|---|---|---|---|---|---|---|---|---|---|---|
| | 290 | | | | | 295 | | | | | 300 | |

( 2 ) INFORMATION FOR SEQ ID NO:3:

( i ) SEQUENCE CHARACTERISTICS:
        ( A ) LENGTH: 1105 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GCTTAATTAA TTAAGCTTAA AAGGAGGAAA AAAATTATGG CCGAGATAAC CCTAGAGCCG      60
AGTGATCTTA TGGCGCAAAC AAACAAAAGA ATAGTGCCAA AGTTCACTGA AATCTTCCCC     120
GTGGAGGACG CGAACTACCC TTACAGCGCC TTCATCGCGT CGGTCCGGAA AGACGTGATC     180
```

```
AAACACTGCA CCGACCATAA AGGGATCTTC CAGCCCGTGC TGCCACCGGA GAAGAAGGTC    240
CCGGAGCTAT GGTTCTACAC AGAGCTCAAA ACTAGGACCA GCTCCATCAC GCTCGCCATA    300
CGCATGGACA ACCTGTACCT CGTGGGCTTC AGGACCCCGG GCGGGGTGTG GTGGGAGTTC    360
GGCAAGGACG GCGACACCCA CCTCCTCGGC GACAACCCCA GGTGGCTCGG CTTCGGCGGC    420
AGGTACCAGG ACCTCATCGG CAACAAGGGT CTGGAGACCG TCACCATGGG CCGCGCCGAA    480
ATGACCAGGG CCGTCAACGA CCTGGCGAAG AAGAAGAAGA TGGCGACACT GGAGGAGGAG    540
GAGGTGAAGA TGCAGATGCA GATGCCGGAG GCCGCTGATC TGGCGGCGGC GGCAGCGGCT    600
GACCCACAGG CCGACACGAA GAGCAAGCTG GTGAAGCTGG TGGTCATGGT GTGCGAGGGG    660
CTGCGGTTCA ACACCGTGTC CCGCACGGTG GACGCGGGGT TCAACAGCCA GCACGGGGTG    720
ACCTTGACCG TGACGCAGGG GAAGCAGGTG CAGAAGTGGG ACAGGATCTC CAAGGCGGCC    780
TTCGAGTGGG CTGACCACCC CACCGCTGTG ATCCCCGACA TGCAGAAGCT TGGCATCAAG    840
GATAAGAACG AAGCAGCGAG GATCGTTGCG CTCGTTAAGA ATCAAACTAC TGCCGCTGCC    900
GCTACTGCTG CCAGTGCTGA CAACGACGAC GACGAGGCCT GATCAATGCA ACGACACATC    960
ATGATCTGCT GCTGCACTTA ATTACTATGT TCGTACACAA ATAAATACAC CCGGCGTACG   1020
CGGTGTTCCT TATATGGTCT AAAATGTAGC CAGTAAATTT TAAACTACTT TCTCGTGCCG   1080
AATTCACTGG CCGGCATGCT ATATA                                        1105
```

( 2 ) INFORMATION FOR SEQ ID NO:4:

( i ) SEQUENCE CHARACTERISTICS:
        ( A ) LENGTH: 1074 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..911

( x i ) SEQUENCE DESCRIPTION: SEQ ID NO:4:

```
TCCCTCTAGA TGCGGCCTAA TTAATTAAGC TTAAAAGGAG GAAAAAAATT ATG AAA       56
                                                      Met Lys
                                                        1

AGA ATA GTG CCA AAG TTC ACT GAA ATC TTC CCC GTG GAG GAC GCG AAC    104
Arg Ile Val Pro Lys Phe Thr Glu Ile Phe Pro Val Glu Asp Ala Asn
      5              10                  15

TAC CCT TAC AGC GCC TTC ATC GCG TCG GTC CGG AAA GAC GTG ATC AAA    152
Tyr Pro Tyr Ser Ala Phe Ile Ala Ser Val Arg Lys Asp Val Ile Lys
    20                  25                  30

CAC TGC ACC GAC CAT AAA GGG ATC TTC CAG CCC GTG CTG CCA CCG GAG    200
His Cys Thr Asp His Lys Gly Ile Phe Gln Pro Val Leu Pro Pro Glu
 35                  40                  45                   50

AAG AAG GTC CCG GAG CTA TGG TTC TAC ACA GAG CTC AAA ACT AGG ACC    248
Lys Lys Val Pro Glu Leu Trp Phe Tyr Thr Glu Leu Lys Thr Arg Thr
                 55                  60                  65

AGC TCC ATC ACG CTC GCC ATA CGC ATG GAC AAC CTG TAC CTC GTG GGC    296
Ser Ser Ile Thr Leu Ala Ile Arg Met Asp Asn Leu Tyr Leu Val Gly
             70                  75                  80

TTC AGG ACC CCG GGC GGG GTG TGG TGG GAG TTC GGC AAG GAC GGC GAC    344
Phe Arg Thr Pro Gly Gly Val Trp Trp Glu Phe Gly Lys Asp Gly Asp
         85                  90                  95

ACC CAC CTC CTC GGC GAC AAC CCC AGG TGG CTC GGC TTC GGC GGC AGG    392
Thr His Leu Leu Gly Asp Asn Pro Arg Trp Leu Gly Phe Gly Gly Arg
     100                 105                 110
```

-continued

| | | | | | | | | | | | | | | | | |
|---|---|---|---|---|---|---|---|---|---|---|---|---|---|---|---|---|
| TAC | CAG | GAC | CTC | ATC | GGC | AAC | AAG | GGT | CTG | GAG | ACC | GTC | ACC | ATG | GGC | 440 |
| Tyr | Gln | Asp | Leu | Ile | Gly | Asn | Lys | Gly | Leu | Glu | Thr | Val | Thr | Met | Gly | |
| 115 | | | | 120 | | | | | 125 | | | | | 130 | | |
| CGC | GCC | GAA | ATG | ACC | AGG | GCC | GTC | AAC | GAC | CTG | GCG | AAG | AAG | AAG | AAG | 488 |
| Arg | Ala | Glu | Met | Thr | Arg | Ala | Val | Asn | Asp | Leu | Ala | Lys | Lys | Lys | Lys | |
| | | | | 135 | | | | | 140 | | | | | 145 | | |
| ATG | GCG | ACA | CTG | GAG | GAG | GAG | GAG | GTG | AAG | ATG | CAG | ATG | CAG | ATG | CCG | 536 |
| Met | Ala | Thr | Leu | Glu | Glu | Glu | Glu | Val | Lys | Met | Gln | Met | Gln | Met | Pro | |
| | | | 150 | | | | | 155 | | | | | 160 | | | |
| GAG | GCC | GCT | GAT | CTG | GCG | GCG | GCG | GCA | GCG | GCT | GAC | CCA | CAG | GCC | GAC | 584 |
| Glu | Ala | Ala | Asp | Leu | Ala | Ala | Ala | Ala | Ala | Ala | Asp | Pro | Gln | Ala | Asp | |
| | | 165 | | | | 170 | | | | | 175 | | | | | |
| ACG | AAG | AGC | AAG | CTG | GTG | AAG | CTG | GTG | GTC | ATG | GTG | TGC | GAG | GGG | CTG | 632 |
| Thr | Lys | Ser | Lys | Leu | Val | Lys | Leu | Val | Val | Met | Val | Cys | Glu | Gly | Leu | |
| | 180 | | | | | 185 | | | | | 190 | | | | | |
| CGG | TTC | AAC | ACC | GTG | TCC | CGC | ACG | GTG | GAC | GCG | GGG | TTC | AAC | AGC | CAG | 680 |
| Arg | Phe | Asn | Thr | Val | Ser | Arg | Thr | Val | Asp | Ala | Gly | Phe | Asn | Ser | Gln | |
| 195 | | | | | 200 | | | | | 205 | | | | | 210 | |
| CAC | GGG | GTG | ACC | TTG | ACC | GTG | ACG | CAG | GGG | AAG | CAG | GTG | CAG | AAG | TGG | 728 |
| His | Gly | Val | Thr | Leu | Thr | Val | Thr | Gln | Gly | Lys | Gln | Val | Gln | Lys | Trp | |
| | | | | 215 | | | | 220 | | | | | 225 | | | |
| GAC | AGG | ATC | TCC | AAG | GCG | GCC | TTC | GAG | TGG | GCT | GAC | CAC | CCC | ACC | GCT | 776 |
| Asp | Arg | Ile | Ser | Lys | Ala | Ala | Phe | Glu | Trp | Ala | Asp | His | Pro | Thr | Ala | |
| | | | 230 | | | | 235 | | | | | 240 | | | | |
| GTG | ATC | CCC | GAC | ATG | CAG | AAG | CTT | GGC | ATC | AAG | GAT | AAG | AAC | GAA | GCA | 824 |
| Val | Ile | Pro | Asp | Met | Gln | Lys | Leu | Gly | Ile | Lys | Asp | Lys | Asn | Glu | Ala | |
| | | 245 | | | | 250 | | | | | 255 | | | | | |
| GCG | AGG | ATC | GTT | GCG | CTC | GTT | AAG | AAT | CAA | ACT | ACT | GCC | GCT | GCC | GCT | 872 |
| Ala | Arg | Ile | Val | Ala | Leu | Val | Lys | Asn | Gln | Thr | Thr | Ala | Ala | Ala | Ala | |
| | 260 | | | | | 265 | | | | | 270 | | | | | |
| ACT | GCT | GCC | AGT | GCT | GAC | AAC | GAC | GAC | GAC | GAG | GCC | TGATCAATGC | | | | 918 |
| Thr | Ala | Ala | Ser | Ala | Asp | Asn | Asp | Asp | Asp | Glu | Ala | | | | | |
| 275 | | | | 280 | | | | | 285 | | | | | | | |

```
AACGACACAT CATGATCTGC TGCTGCACTT AATTACTATG TTCGTATACA AATAAATACA    978
CCCGGCGTAC GCGGTGTTCC TTATATGGTC TAAAATGTAG CCAGTAAATT TTAAACTACT   1038
TTCTCGTGCC GAATTCACTG GCCGGCATGC TATATA                              1074
```

( 2 ) INFORMATION FOR SEQ ID NO:5:

( i ) SEQUENCE CHARACTERISTICS:
        ( A ) LENGTH: 286 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
| Met | Lys | Arg | Ile | Val | Pro | Lys | Phe | Thr | Glu | Ile | Phe | Pro | Val | Glu | Asp |
| 1 | | | | 5 | | | | | 10 | | | | | 15 | |
| Ala | Asn | Tyr | Pro | Tyr | Ser | Ala | Phe | Ile | Ala | Ser | Val | Arg | Lys | Asp | Val |
| | | | 20 | | | | | 25 | | | | | 30 | | |
| Ile | Lys | His | Cys | Thr | Asp | His | Lys | Gly | Ile | Phe | Gln | Pro | Val | Leu | Pro |
| | | | 35 | | | | 40 | | | | | 45 | | | |
| Pro | Glu | Lys | Lys | Val | Pro | Glu | Leu | Trp | Phe | Tyr | Thr | Glu | Leu | Lys | Thr |
| | 50 | | | | | 55 | | | | | 60 | | | | |
| Arg | Thr | Ser | Ser | Ile | Thr | Leu | Ala | Ile | Arg | Met | Asp | Asn | Leu | Tyr | Leu |
| 65 | | | | | 70 | | | | | 75 | | | | | 80 |
| Val | Gly | Phe | Arg | Thr | Pro | Gly | Gly | Val | Trp | Trp | Glu | Phe | Gly | Lys | Asp |
| | | | | 85 | | | | | 90 | | | | | 95 | |

| | | | | | | | | | | | | | | |
|---|---|---|---|---|---|---|---|---|---|---|---|---|---|---|
| Gly | Asp | Thr | His | Leu | Leu | Gly | Asp | Asn | Pro | Arg | Trp | Leu | Gly | Phe | Gly |
| | | | 100 | | | | | 105 | | | | | 110 | | |

Gly Arg Tyr Gln Asp Leu Ile Gly Asn Lys Gly Leu Glu Thr Val Thr
           115                   120                  125

Met Gly Arg Ala Glu Met Thr Arg Ala Val Asn Asp Leu Ala Lys Lys
 130                     135                     140

Lys Lys Met Ala Thr Leu Glu Glu Glu Val Lys Met Gln Met Gln
145               150                 155                160

Met Pro Glu Ala Ala Asp Leu Ala Ala Ala Ala Ala Asp Pro Gln
                165             170                175

Ala Asp Thr Lys Ser Lys Leu Val Lys Leu Val Val Met Val Cys Glu
         180                185             190

Gly Leu Arg Phe Asn Thr Val Ser Arg Thr Val Asp Ala Gly Phe Asn
        195               200             205

Ser Gln His Gly Val Thr Leu Thr Val Thr Gln Gly Lys Gln Val Gln
   210                 215              220

Lys Trp Asp Arg Ile Ser Lys Ala Ala Phe Glu Trp Ala Asp His Pro
225              230             235             240

Thr Ala Val Ile Pro Asp Met Gln Lys Leu Gly Ile Lys Asp Lys Asn
            245             250            255

Glu Ala Ala Arg Ile Val Ala Leu Val Lys Asn Gln Thr Thr Ala Ala
        260               265             270

Ala Ala Thr Ala Ala Ser Ala Asp Asn Asp Asp Asp Glu Ala
     275               280             285

( 2 ) INFORMATION FOR SEQ ID NO:6:

( i ) SEQUENCE CHARACTERISTICS:
        ( A ) LENGTH: 1029 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 36..863

( x i ) SEQUENCE DESCRIPTION: SEQ ID NO:6:

```
GCTAATTAAT TAAGCTTAAA AGGAGGAAAA AAATT ATG GCC GAG ATA ACC CTA        53
                                       Met Ala Glu Ile Thr Leu
                                        1               5

GAG CCG AGT GAT CTT ATG GCG CAA ACA AAC AAA AGA ATA GTG CCA AAG      101
Glu Pro Ser Asp Leu Met Ala Gln Thr Asn Lys Arg Ile Val Pro Lys
             10                  15                  20

TTC ACT GAA ATC TTC CCC GTG GAG GAC GCG AAC TAC CCT TAC AGC GCC     149
Phe Thr Glu Ile Phe Pro Val Glu Asp Ala Asn Tyr Pro Tyr Ser Ala
         25                  30                  35

TTC ATC GCG TCG GTC CGG AAA GAC GTG ATC AAA CAC TGC ACC GAC CAT     197
Phe Ile Ala Ser Val Arg Lys Asp Val Ile Lys His Cys Thr Asp His
     40                  45                  50

AAA GGG ATC TTC CAG CCC GTG CTG CCA CCG GAG AAG AAG GTC CCG GAG     245
Lys Gly Ile Phe Gln Pro Val Leu Pro Pro Glu Lys Lys Val Pro Glu
 55                  60                  65                  70

CTA TGG TTC TAC ACA GAG CTC AAA ACT AGG ACC AGC TCC ATC ACG CTC     293
Leu Trp Phe Tyr Thr Glu Leu Lys Thr Arg Thr Ser Ser Ile Thr Leu
                 75                  80                  85

GCC ATA CGC ATG GAC AAC CTG TAC CTC GTG GGC TTC AGG ACC CCG GGC     341
Ala Ile Arg Met Asp Asn Leu Tyr Leu Val Gly Phe Arg Thr Pro Gly
         90                  95                 100

GGG GTG TGG TGG GAG TTC GGC AAG GAC GGC GAC ACC CAC CTC CTC GGC     389
```

| | | | | | | | | | | | | | | | | |
|---|---|---|---|---|---|---|---|---|---|---|---|---|---|---|---|---|
| | Gly | Val | Trp 105 | Trp | Glu | Phe | Gly | Lys 110 | Asp | Gly | Asp | Thr | His 115 | Leu | Leu | Gly |
| GAC | AAC | CCC | AGG | TGG | CTC | GGC | TTC | GGC | GGC | AGG | TAC | CAG | GAC | CTC | ATC | 437 |
| Asp | Asn 120 | Pro | Arg | Trp | Leu 125 | Gly | Phe | Gly | Gly 130 | Arg | Tyr | Gln | Asp | Leu | Ile | |
| GGC | AAC | AAG | GGT | CTG | GAG | ACC | GTC | ACC | ATG | GGC | CGC | GCC | GAA | ATG | ACC | 485 |
| Gly 135 | Asn | Lys | Gly | Leu 140 | Glu | Thr | Val | Thr 145 | Met | Gly | Arg | Ala | Glu 150 | Met | Thr | |
| AGG | GCC | GTC | AAC | GAC | CTG | GCG | AAG | AAG | AAG | AAG | GCG | GCT | GAC | CCA | CAG | 533 |
| Arg | Ala | Val | Asn 155 | Asp | Leu | Ala | Lys | Lys 160 | Lys | Lys | Ala | Ala | Asp 165 | Pro | Gln | |
| GCC | GAC | ACG | AAG | AGC | AAG | CTG | GTG | AAG | CTG | GTG | GTC | ATG | GTG | TGC | GAG | 581 |
| Ala | Asp | Thr 170 | Lys | Ser | Lys | Leu | Val 175 | Lys | Leu | Val | Val | Met 180 | Val | Cys | Glu | |
| GGG | CTG | CGG | TTC | AAC | ACC | GTG | TCC | CGC | ACG | GTG | GAC | GCG | GGG | TTC | AAC | 629 |
| Gly | Leu | Arg 185 | Phe | Asn | Thr | Val | Ser 190 | Arg | Thr | Val | Asp | Ala 195 | Gly | Phe | Asn | |
| AGC | CAG | CAC | GGG | GTG | ACC | TTG | ACC | GTG | ACG | CAG | GGG | AAG | CAG | GTG | CAG | 677 |
| Ser | Gln 200 | His | Gly | Val | Thr | Leu 205 | Thr | Val | Thr | Gln | Gly 210 | Lys | Gln | Val | Gln | |
| AAG | TGG | GAC | AGG | ATC | TCC | AAG | GCG | GCC | TTC | GAG | TGG | GCT | GAC | CAC | CCC | 725 |
| Lys 215 | Trp | Asp | Arg | Ile | Ser 220 | Lys | Ala | Ala | Phe | Glu 225 | Trp | Ala | Asp | His | Pro 230 | |
| ACC | GCT | GTG | ATC | CCC | GAC | ATG | CAG | AAG | CTT | GGC | ATC | AAG | GAT | AAG | AAC | 773 |
| Thr | Ala | Val | Ile | Pro 235 | Asp | Met | Gln | Lys | Leu 240 | Gly | Ile | Lys | Asp | Lys 245 | Asn | |
| GAA | GCA | GCG | AGG | ATC | GTT | GCG | CTC | GTT | AAG | AAT | CAA | ACT | ACT | GCC | GCT | 821 |
| Glu | Ala | Ala | Arg 250 | Ile | Val | Ala | Leu | Val 255 | Lys | Asn | Gln | Thr | Thr 260 | Ala | Ala | |
| GCC | GCT | ACT | GCT | GCC | AGT | GCT | GAC | AAC | GAC | GAC | GAC | GAG | GCC | | | 863 |
| Ala | Ala | Thr 265 | Ala | Ala | Ser | Ala | Asp 270 | Asn | Asp | Asp | Asp | Glu 275 | Ala | | | |

```
TGATCAATGC AACGACACAT CATGATCTGC TGCTGCACTT AATTACTATG TTCGTATACA        923
AATAAATACA CCCGGCGTAC GCGGTGTTCC TTATATGGTC TAAAATGTAG CCAGTAAATT        983
TTAAACTACT TTCTCGTGCC GAATTCACTG GCCGGCATGC TATATA                      1029
```

( 2 ) INFORMATION FOR SEQ ID NO:7:

( i ) SEQUENCE CHARACTERISTICS:
        ( A ) LENGTH: 276 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | |
|---|---|---|---|---|---|---|---|---|---|---|---|---|---|---|
| Met 1 | Ala | Glu | Ile | Thr 5 | Leu | Glu | Pro | Ser | Asp 10 | Leu | Met | Ala | Gln | Thr Asn 15 |
| Lys | Arg | Ile | Val 20 | Pro | Lys | Phe | Thr | Glu 25 | Ile | Phe | Pro | Val | Glu 30 | Asp Ala |
| Asn | Tyr | Pro 35 | Tyr | Ser | Ala | Phe | Ile 40 | Ala | Ser | Val | Arg | Lys 45 | Asp | Val Ile |
| Lys | His 50 | Cys | Thr | Asp | His | Lys 55 | Gly | Ile | Phe | Gln | Pro 60 | Val | Leu | Pro Pro |
| Glu 65 | Lys | Lys | Val | Pro | Glu 70 | Leu | Trp | Phe | Tyr | Thr 75 | Glu | Leu | Lys | Thr Arg 80 |
| Thr | Ser | Ser | Ile | Thr 85 | Leu | Ala | Ile | Arg | Met 90 | Asp | Asn | Leu | Tyr | Leu Val 95 |
| Gly | Phe | Arg | Thr | Pro | Gly | Gly | Val | Trp | Trp | Glu | Phe | Gly | Lys | Asp Gly |

|     |     |     |     |     |     |     |     |     |     |     |     |     |     |
| --- | --- | --- | --- | --- | --- | --- | --- | --- | --- | --- | --- | --- | --- |
|     |     |     |     |     | 100 |     |     |     |     | 105 |     |     | 110 |
| Asp | Thr | His | Leu | Leu | Gly | Asp | Asn | Pro | Arg | Trp | Leu | Gly | Phe | Gly | Gly |
|     |     | 115 |     |     |     |     | 120 |     |     |     |     | 125 |     |     |     |
| Arg | Tyr | Gln | Asp | Leu | Ile | Gly | Asn | Lys | Gly | Leu | Glu | Thr | Val | Thr | Met |
|     |     | 130 |     |     |     |     | 135 |     |     |     |     | 140 |     |     |     |
| Gly | Arg | Ala | Glu | Met | Thr | Arg | Ala | Val | Asn | Asp | Leu | Ala | Lys | Lys | Lys |
| 145 |     |     |     |     | 150 |     |     |     |     | 155 |     |     |     |     | 160 |
| Lys | Ala | Ala | Asp | Pro | Gln | Ala | Asp | Thr | Lys | Ser | Lys | Leu | Val | Lys | Leu |
|     |     |     |     | 165 |     |     |     |     | 170 |     |     |     |     | 175 |     |
| Val | Val | Met | Val | Cys | Glu | Gly | Leu | Arg | Phe | Asn | Thr | Val | Ser | Arg | Thr |
|     |     |     | 180 |     |     |     |     | 185 |     |     |     |     | 190 |     |     |
| Val | Asp | Ala | Gly | Phe | Asn | Ser | Gln | His | Gly | Val | Thr | Leu | Thr | Val | Thr |
|     |     |     | 195 |     |     |     |     | 200 |     |     |     |     | 205 |     |     |
| Gln | Gly | Lys | Gln | Val | Gln | Lys | Trp | Asp | Arg | Ile | Ser | Lys | Ala | Ala | Phe |
|     | 210 |     |     |     |     | 215 |     |     |     |     |     | 220 |     |     |     |
| Glu | Trp | Ala | Asp | His | Pro | Thr | Ala | Val | Ile | Pro | Asp | Met | Gln | Lys | Leu |
| 225 |     |     |     |     | 230 |     |     |     |     | 235 |     |     |     |     | 240 |
| Gly | Ile | Lys | Asp | Lys | Asn | Glu | Ala | Ala | Arg | Ile | Val | Ala | Leu | Val | Lys |
|     |     |     |     | 245 |     |     |     |     | 250 |     |     |     |     | 255 |     |
| Asn | Gln | Thr | Thr | Ala | Ala | Ala | Ala | Thr | Ala | Ala | Ser | Ala | Asp | Asn | Asp |
|     |     |     | 260 |     |     |     |     | 265 |     |     |     |     | 270 |     |     |
| Asp | Asp | Glu | Ala |
|     |     |     | 275 |

(2) INFORMATION FOR SEQ ID NO:8:

(i) SEQUENCE CHARACTERISTICS:
        (A) LENGTH: 985 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 37..822

(xi) SEQUENCE DESCRIPTION: SEQ ID NO:8:

```
GCTTAATTAA TTAAGCTTAA AAGGAGGAAA AAAATT ATG AAA AGA ATA GTG CCA        54
                                        Met Lys Arg Ile Val Pro
                                          1               5

AAG TTC ACT GAA ATC TTC CCC GTG GAG GAC GCG AAC TAC CCT TAC AGC       102
Lys Phe Thr Glu Ile Phe Pro Val Glu Asp Ala Asn Tyr Pro Tyr Ser
             10                  15                  20

GCC TTC ATC GCG TCG GTC CGG AAA GAC GTG ATC AAA CAC TGC ACC GAC       150
Ala Phe Ile Ala Ser Val Arg Lys Asp Val Ile Lys His Cys Thr Asp
         25                  30                  35

CAT AAA GGG ATC TTC CAG CCC GTG CTG CCA CCG GAG AAG AAG GTC CCG       198
His Lys Gly Ile Phe Gln Pro Val Leu Pro Pro Glu Lys Lys Val Pro
     40                  45                  50

GAG CTA TGG TTC TAC ACA GAG CTC AAA ACT AGG ACC AGC TCC ATC ACG       246
Glu Leu Trp Phe Tyr Thr Glu Leu Lys Thr Arg Thr Ser Ser Ile Thr
 55                  60                  65                  70

CTC GCC ATA CGC ATG GAC AAC CTG TAC CTC GTG GGC TTC AGG ACC CCG       294
Leu Ala Ile Arg Met Asp Asn Leu Tyr Leu Val Gly Phe Arg Thr Pro
                 75                  80                  85

GGC GGG GTG TGG TGG GAG TTC GGC AAG GAC GGC GAC ACC CAC CTC CTC       342
Gly Gly Val Trp Trp Glu Phe Gly Lys Asp Gly Asp Thr His Leu Leu
             90                  95                 100

GGC GAC AAC CCC AGG TGG CTC GGC TTC GGC GGC AGG TAC CAG GAC CTC       390
Gly Asp Asn Pro Arg Trp Leu Gly Phe Gly Gly Arg Tyr Gln Asp Leu
```

|     |     |     |     | 105 |     |     |     |     | 110 |     |     |     |     | 115 |     |     |
|---|---|---|---|---|---|---|---|---|---|---|---|---|---|---|---|---|

| ATC | GGC | AAC | AAG | GGT | CTG | GAG | ACC | GTC | ACC | ATG | GGC | CGC | GCC | GAA | ATG | 438 |
| Ile | Gly | Asn | Lys | Gly | Leu | Glu | Thr | Val | Thr | Met | Gly | Arg | Ala | Glu | Met |     |
|     | 120 |     |     |     |     | 125 |     |     |     |     | 130 |     |     |     |     |     |

| ACC | AGG | GCC | GTC | AAC | GAC | CTG | GCG | AAG | AAG | AAG | AAG | GCG | GCT | GAC | CCA | 486 |
| Thr | Arg | Ala | Val | Asn | Asp | Leu | Ala | Lys | Lys | Lys | Lys | Ala | Ala | Asp | Pro |     |
| 135 |     |     |     |     | 140 |     |     |     |     | 145 |     |     |     |     | 150 |     |

| CAG | GCC | GAC | ACG | AAG | AGC | AAG | CTG | GTG | AAG | CTG | GTG | GTC | ATG | GTG | TGC | 534 |
| Gln | Ala | Asp | Thr | Lys | Ser | Lys | Leu | Val | Lys | Leu | Val | Val | Met | Val | Cys |     |
|     |     |     |     | 155 |     |     |     |     | 160 |     |     |     |     | 165 |     |     |

| GAG | GGG | CTG | CGG | TTC | AAC | ACC | GTG | TCC | CGC | ACG | GTG | GAC | GCG | GGG | TTC | 582 |
| Glu | Gly | Leu | Arg | Phe | Asn | Thr | Val | Ser | Arg | Thr | Val | Asp | Ala | Gly | Phe |     |
|     |     |     | 170 |     |     |     |     | 175 |     |     |     |     | 180 |     |     |     |

| AAC | AGC | CAG | CAC | GGG | GTG | ACC | TTG | ACC | GTG | ACG | CAG | GGG | AAG | CAG | GTG | 630 |
| Asn | Ser | Gln | His | Gly | Val | Thr | Leu | Thr | Val | Thr | Gln | Gly | Lys | Gln | Val |     |
|     |     | 185 |     |     |     |     | 190 |     |     |     |     | 195 |     |     |     |     |

| CAG | AAG | TGG | GAC | AGG | ATC | TCC | AAG | GCG | GCC | TTC | GAG | TGG | GCT | GAC | CAC | 678 |
| Gln | Lys | Trp | Asp | Arg | Ile | Ser | Lys | Ala | Ala | Phe | Glu | Trp | Ala | Asp | His |     |
|     | 200 |     |     |     |     | 205 |     |     |     |     | 210 |     |     |     |     |     |

| CCC | ACC | GCT | GTG | ATC | CCC | GAC | ATG | CAG | AAG | CTT | GGC | ATC | AAG | GAT | AAG | 726 |
| Pro | Thr | Ala | Val | Ile | Pro | Asp | Met | Gln | Lys | Leu | Gly | Ile | Lys | Asp | Lys |     |
| 215 |     |     |     |     | 220 |     |     |     |     | 225 |     |     |     |     | 230 |     |

| AAC | GAA | GCA | GCG | AGG | ATC | GTT | GCG | CTC | GTT | AAG | AAT | CAA | ACT | ACT | GCC | 774 |
| Asn | Glu | Ala | Ala | Arg | Ile | Val | Ala | Leu | Val | Lys | Asn | Gln | Thr | Thr | Ala |     |
|     |     |     |     | 235 |     |     |     |     | 240 |     |     |     |     | 245 |     |     |

| GCT | GCC | GCT | ACT | GCT | GCC | AGT | GCT | GAC | AAC | GAC | GAC | GAC | GAG | GCC | TGATCAATGC | 829 |
| Ala | Ala | Ala | Thr | Ala | Ala | Ser | Ala | Asp | Asn | Asp | Asp | Asp | Glu | Ala |            |     |
|     |     |     | 250 |     |     |     |     | 255 |     |     |     |     | 260 |     |            |     |

| AACGACACAT | CATGATCTGC | TGCTGCACTT | AATTACTATG | TTCGTATACA | AATAAATACA | 889 |
| CCCGGCGTAC | GCGGTGTTCC | TTATATGGTC | TAAAATGTAG | CCAGTAAATT | TTAAACTACT | 949 |
| TTCTCGTGCC | GAATTCACTG | GCCGGCATGC | TATATA     |            |            | 985 |

( 2 ) INFORMATION FOR SEQ ID NO:9:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | Lys | Arg | Ile | Val | Pro | Lys | Phe | Thr | Glu | Ile | Phe | Pro | Val | Glu | Asp |
|---|---|---|---|---|---|---|---|---|---|---|---|---|---|---|---|
| 1 |     |     |     | 5 |     |     |     |     | 10 |     |     |     |     | 15 |     |

| Ala | Asn | Tyr | Pro | Tyr | Ser | Ala | Phe | Ile | Ala | Ser | Val | Arg | Lys | Asp | Val |
|     |     |     | 20 |     |     |     |     | 25 |     |     |     |     | 30 |     |     |

| Ile | Lys | His | Cys | Thr | Asp | His | Lys | Gly | Ile | Phe | Gln | Pro | Val | Leu | Pro |
|     |     | 35 |     |     |     |     | 40 |     |     |     |     | 45 |     |     |     |

| Pro | Glu | Lys | Lys | Val | Pro | Glu | Leu | Trp | Phe | Tyr | Thr | Glu | Leu | Lys | Thr |
|     | 50 |     |     |     |     | 55 |     |     |     |     | 60 |     |     |     |     |

| Arg | Thr | Ser | Ser | Ile | Thr | Leu | Ala | Ile | Arg | Met | Asp | Asn | Leu | Tyr | Leu |
| 65 |     |     |     |     | 70 |     |     |     |     | 75 |     |     |     |     | 80 |

| Val | Gly | Phe | Arg | Thr | Pro | Gly | Gly | Val | Trp | Trp | Glu | Phe | Gly | Lys | Asp |
|     |     |     |     | 85 |     |     |     |     | 90 |     |     |     |     | 95 |     |

| Gly | Asp | Thr | His | Leu | Leu | Gly | Asp | Asn | Pro | Arg | Trp | Leu | Gly | Phe | Gly |
|     |     |     | 100 |     |     |     |     | 105 |     |     |     |     | 110 |     |     |

| Gly | Arg | Tyr | Gln | Asp | Leu | Ile | Gly | Asn | Lys | Gly | Leu | Glu | Thr | Val | Thr |
|     |     | 115 |     |     |     |     | 120 |     |     |     |     | 125 |     |     |     |

```
Met Gly Arg Ala Glu Met Thr Arg Ala Val Asn Asp Leu Ala Lys Lys
    130                 135                 140

Lys Lys Ala Ala Asp Pro Gln Ala Asp Thr Lys Ser Lys Leu Val Lys
145                 150                 155                 160

Leu Val Val Met Val Cys Glu Gly Leu Arg Phe Asn Thr Val Ser Arg
                165                 170                 175

Thr Val Asp Ala Gly Phe Asn Ser Gln His Gly Val Thr Leu Thr Val
            180                 185                 190

Thr Gln Gly Lys Gln Val Gln Lys Trp Asp Arg Ile Ser Lys Ala Ala
        195                 200                 205

Phe Glu Trp Ala Asp His Pro Thr Ala Val Ile Pro Asp Met Gln Lys
    210                 215                 220

Leu Gly Ile Lys Asp Lys Asn Glu Ala Ala Arg Ile Val Ala Leu Val
225                 230                 235                 240

Lys Asn Gln Thr Thr Ala Ala Ala Ala Thr Ala Ala Ser Ala Asp Asn
                245                 250                 255

Asp Asp Asp Glu Ala
            260
```

( 2 ) INFORMATION FOR SEQ ID NO:10:

( i ) SEQUENCE CHARACTERISTICS:
        ( A ) LENGTH: 978 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..815

( x i ) SEQUENCE DESCRIPTION: SEQ ID NO:10:

```
TCCCTCTAGA TGCGGCCTAA TTAATTAAGC TTAAAAGGAG GAAAAAAATT ATG AAA            56
                                                      Met Lys
                                                        1

AGA ATA GTG CCA AAG TTC ACT GAA ATC TTC CCC GTG GAG GAC GCG AAC         104
Arg Ile Val Pro Lys Phe Thr Glu Ile Phe Pro Val Glu Asp Ala Asn
          5                  10                  15

TAC CCT TAC AGC GCC TTC ATC GCG TCG GTC CGG AAA GAC GTG ATC AAA         152
Tyr Pro Tyr Ser Ala Phe Ile Ala Ser Val Arg Lys Asp Val Ile Lys
         20                  25                  30

CAC TGC ACC GAC CAT AAA GGG ATC TTC CAG CCC GTG CTG CCA CCG GAG         200
His Cys Thr Asp His Lys Gly Ile Phe Gln Pro Val Leu Pro Pro Glu
 35                  40                  45                  50

AAG AAG GTC CCG GAG CTA TGG TTC TAC ACA GAG CTC AAA ACT AGG ACC         248
Lys Lys Val Pro Glu Leu Trp Phe Tyr Thr Glu Leu Lys Thr Arg Thr
                 55                  60                  65

AGC TCC ATC ACG CTC GCC ATA CGC ATG GAC AAC CTG TAC CTC GTG GGC         296
Ser Ser Ile Thr Leu Ala Ile Arg Met Asp Asn Leu Tyr Leu Val Gly
             70                  75                  80

TTC AGG ACC CCG GGC GGG GTG TGG TGG GAG TTC GGC AAG GAC GGC GAC         344
Phe Arg Thr Pro Gly Gly Val Trp Trp Glu Phe Gly Lys Asp Gly Asp
         85                  90                  95

ACC CAC CTC CTC GGC GAC AAC CCC AGG TGG CTC GGC TTC GGC GGC AGG         392
Thr His Leu Leu Gly Asp Asn Pro Arg Trp Leu Gly Phe Gly Gly Arg
100                 105                 110

TAC CAG GAC CTC ATC GGC AAC AAG GGT CTG GAG ACC GTC ACC ATG GGC         440
Tyr Gln Asp Leu Ile Gly Asn Lys Gly Leu Glu Thr Val Thr Met Gly
115                 120                 125                 130

CGC GCC GAA ATG ACC AGG GCC GTC AAC GAC CTG GCG AAG AAG AAG AAG         488
```

|     |     |     |     |     |     |     |     |     |     |     |     |     |     |     |
| --- | --- | --- | --- | --- | --- | --- | --- | --- | --- | --- | --- | --- | --- | --- |
| Arg | Ala | Glu | Met | Thr | Arg | Ala | Val | Asn | Asp | Leu | Ala | Lys | Lys | Lys | Lys |
|     |     |     |     | 135 |     |     |     | 140 |     |     |     |     | 145 |     |     |

```
GCG GCT GAC CCA CAG GCC GAC ACG AAG AGC AAG CTG GTG AAG CTG GTG             536
Ala Ala Asp Pro Gln Ala Asp Thr Lys Ser Lys Leu Val Lys Leu Val
            150             155             160

GTC ATG GTG TGC GAG GGG CTG CGG TTC AAC ACC GTG TCC CGC ACG GTG             584
Val Met Val Cys Glu Gly Leu Arg Phe Asn Thr Val Ser Arg Thr Val
        165             170             175

GAC GCG GGG TTC AAC AGC CAG CAC GGG GTG ACC TTG ACC GTG ACG CAG             632
Asp Ala Gly Phe Asn Ser Gln His Gly Val Thr Leu Thr Val Thr Gln
    180             185             190

GGG AAG CAG GTG CAG AAG TGG GAC AGG ATC TCC AAG GCG GCC TTC GAG             680
Gly Lys Gln Val Gln Lys Trp Asp Arg Ile Ser Lys Ala Ala Phe Glu
195             200             205             210

TGG GCT GAC CAC CCC ACC GCT GTG ATC CCC GAC ATG CAG AAG CTT GGC             728
Trp Ala Asp His Pro Thr Ala Val Ile Pro Asp Met Gln Lys Leu Gly
            215             220             225

ATC AAG GAT AAG AAC GAA GCA GCG AGG ATC GTT GCG CTC GTT AAG AAT             776
Ile Lys Asp Lys Asn Glu Ala Ala Arg Ile Val Ala Leu Val Lys Asn
        230             235             240

CAA ACT ACT GCC GCT GCC GCT ACT GCT GGA TCC GCC TGATCAATGC                  822
Gln Thr Thr Ala Ala Ala Ala Thr Ala Gly Ser Ala
            245             250             255

AACGACACAT CATGATCTGC TGCTGCACTT AATTACTATG TTCGTATACA AATAAATACA            882

CCCGGCGTAC GCGGTGTTCC TTATATGGTC TAAAATGTAG CCAGTAAATT TTAAACTACT            942

TTCTCGTGCC GAATTCACTG GCCGGCATGC TATATA                                     978
```

( 2 ) INFORMATION FOR SEQ ID NO:11:

( i ) SEQUENCE CHARACTERISTICS:
        ( A ) LENGTH: 254 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Lys Arg Ile Val Pro Lys Phe Thr Glu Ile Phe Pro Val Glu Asp
  1             5              10              15

Ala Asn Tyr Pro Tyr Ser Ala Phe Ile Ala Ser Val Arg Lys Asp Val
            20              25              30

Ile Lys His Cys Thr Asp His Lys Gly Ile Phe Gln Pro Val Leu Pro
        35              40              45

Pro Glu Lys Lys Val Pro Glu Leu Trp Phe Tyr Thr Glu Leu Lys Thr
    50              55              60

Arg Thr Ser Ser Ile Thr Leu Ala Ile Arg Met Asp Asn Leu Tyr Leu
65              70              75              80

Val Gly Phe Arg Thr Pro Gly Gly Val Trp Trp Glu Phe Gly Lys Asp
            85              90              95

Gly Asp Thr His Leu Leu Gly Asp Asn Pro Arg Trp Leu Gly Phe Gly
            100             105             110

Gly Arg Tyr Gln Asp Leu Ile Gly Asn Lys Gly Leu Glu Thr Val Thr
        115             120             125

Met Gly Arg Ala Glu Met Thr Arg Ala Val Asn Asp Leu Ala Lys Lys
130             135             140

Lys Lys Ala Ala Asp Pro Gln Ala Asp Thr Lys Ser Lys Leu Val Lys
145             150             155             160

Leu Val Val Met Val Cys Glu Gly Leu Arg Phe Asn Thr Val Ser Arg
```

|   |   |   | 165 |   |   |   |   | 170 |   |   |   |   | 175 |   |   |
|---|---|---|-----|---|---|---|---|-----|---|---|---|---|-----|---|---|

Thr Val Asp Ala Gly Phe Asn Ser Gln His Gly Val Thr Leu Thr Val
            180             185                 190

Thr Gln Gly Lys Gln Val Gln Lys Trp Asp Arg Ile Ser Lys Ala Ala
        195             200                 205

Phe Glu Trp Ala Asp His Pro Thr Ala Val Ile Pro Asp Met Gln Lys
        210             215             220

Leu Gly Ile Lys Asp Lys Asn Glu Ala Ala Arg Ile Val Ala Leu Val
225             230             235                 240

Lys Asn Gln Thr Thr Ala Ala Ala Ala Thr Ala Gly Ser Ala
            245             250

( 2 ) INFORMATION FOR SEQ ID NO:12:

( i ) SEQUENCE CHARACTERISTICS:
        ( A ) LENGTH: 987 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..824

( x i ) SEQUENCE DESCRIPTION: SEQ ID NO:12:

```
TCCCTCTAGA TGCGGCCTAA TTAATTAAGC TTAAAAGGAG GAAAAAAATT ATG AAA           56
                                                      Met Lys
                                                        1

AGA ATA GTG CCA AAG TTC ACT GAA ATC TTC CCC GTG GAG GAC GCG AAC         104
Arg Ile Val Pro Lys Phe Thr Glu Ile Phe Pro Val Glu Asp Ala Asn
          5                  10                  15

TAC CCT TAC AGC GCC TTC ATC GCG TCG GTC CGG AAA GAC GTG ATC AAA         152
Tyr Pro Tyr Ser Ala Phe Ile Ala Ser Val Arg Lys Asp Val Ile Lys
         20                  25                  30

CAC TGC ACC GAC CAT AAA GGG ATC TTC CAG CCC GTG CTG CCA CCG GAG         200
His Cys Thr Asp His Lys Gly Ile Phe Gln Pro Val Leu Pro Pro Glu
 35                  40                  45                  50

AAG AAG GTC CCG GAG CTA TGG TTC TAC ACA GAG CTC AAA ACT AGG ACC         248
Lys Lys Val Pro Glu Leu Trp Phe Tyr Thr Glu Leu Lys Thr Arg Thr
                 55                  60                  65

AGC TCC ATC ACG CTC GCC ATA CGC ATG GAC AAC CTG TAC CTC GTG GGC         296
Ser Ser Ile Thr Leu Ala Ile Arg Met Asp Asn Leu Tyr Leu Val Gly
             70                  75                  80

TTC AGG ACC CCG GGC GGG GTG TGG TGG GAG TTC GGC AAG GAC GGC GAC         344
Phe Arg Thr Pro Gly Gly Val Trp Trp Glu Phe Gly Lys Asp Gly Asp
         85                  90                  95

ACC CAC CTC CTC GGC GAC AAC CCC AGG TGG CTC GGC TTC GGC GGC AGG         392
Thr His Leu Leu Gly Asp Asn Pro Arg Trp Leu Gly Phe Gly Gly Arg
100                 105                 110

TAC CAG GAC CTC ATC GGC AAC AAG GGT CTG GAG ACC GTC ACC ATG GGC         440
Tyr Gln Asp Leu Ile Gly Asn Lys Gly Leu Glu Thr Val Thr Met Gly
115                 120                 125                 130

CGC GCC GAA ATG ACC AGG GCC GTC AAC GAC CTG GCG AAG AAG AAG AAG         488
Arg Ala Glu Met Thr Arg Ala Val Asn Asp Leu Ala Lys Lys Lys Lys
                135                 140                 145

GCG GCC GCC GCT GCA GAC CCA CAG GCC GAC ACG AAG AGC AAG CTG GTG         536
Ala Ala Ala Ala Ala Asp Pro Gln Ala Asp Thr Lys Ser Lys Leu Val
            150                 155                 160

AAG CTG GTG GTC ATG GTG TGC GAG GGG CTG CGG TTC AAC ACC GTG TCC         584
Lys Leu Val Val Met Val Cys Glu Gly Leu Arg Phe Asn Thr Val Ser
        165                 170                 175
```

-continued

```
CGC ACG GTG GAC GCG GGG TTC AAC AGC CAG CAC GGG GTG ACC TTG ACC      632
Arg Thr Val Asp Ala Gly Phe Asn Ser Gln His Gly Val Thr Leu Thr
    180             185                 190

GTG ACG CAG GGG AAG CAG GTG CAG AAG TGG GAC AGG ATC TCC AAG GCG      680
Val Thr Gln Gly Lys Gln Val Gln Lys Trp Asp Arg Ile Ser Lys Ala
195             200                 205                 210

GCC TTC GAG TGG GCT GAC CAC CCC ACC GCT GTG ATC CCC GAC ATG CAG      728
Ala Phe Glu Trp Ala Asp His Pro Thr Ala Val Ile Pro Asp Met Gln
                215                 220                 225

AAG CTT GGC ATC AAG GAT AAG AAC GAA GCA GCG AGG ATC GTT GCG CTC      776
Lys Leu Gly Ile Lys Asp Lys Asn Glu Ala Ala Arg Ile Val Ala Leu
                230                 235                 240

GTT AAG AAT CAA ACT ACT GCC GCT GCC GCT ACT GCT GGA TCC GCC TGATCAATG 831
Val Lys Asn Gln Thr Thr Ala Ala Ala Ala Thr Ala Gly Ser Ala
            245                 250                 255

AACGACACAT CATGATCTGC TGCTGCACTT AATTACTATG TTCGTATACA AATAAATACA     891

CCCGGCGTAC GCGGTGTTCC TTATATGGTC TAAAATGTAG CCAGTAAATT TTAAACTACT     951

TTCTCGTGCC GAATTCACTG GCCGGCATGC TATATA                               987
```

( 2 ) INFORMATION FOR SEQ ID NO:13:

( i ) SEQUENCE CHARACTERISTICS:
        ( A ) LENGTH: 257 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met Lys Arg Ile Val Pro Lys Phe Thr Glu Ile Phe Pro Val Glu Asp
 1               5                  10                  15

Ala Asn Tyr Pro Tyr Ser Ala Phe Ile Ala Ser Val Arg Lys Asp Val
                20                  25                  30

Ile Lys His Cys Thr Asp His Lys Gly Ile Phe Gln Pro Val Leu Pro
            35                  40                  45

Pro Glu Lys Lys Val Pro Glu Leu Trp Phe Tyr Thr Glu Leu Lys Thr
        50                  55                  60

Arg Thr Ser Ser Ile Thr Leu Ala Ile Arg Met Asp Asn Leu Tyr Leu
65                  70                  75                  80

Val Gly Phe Arg Thr Pro Gly Gly Val Trp Trp Glu Phe Gly Lys Asp
                85                  90                  95

Gly Asp Thr His Leu Leu Gly Asp Asn Pro Arg Trp Leu Gly Phe Gly
               100                 105                 110

Gly Arg Tyr Gln Asp Leu Ile Gly Asn Lys Gly Leu Glu Thr Val Thr
           115                 120                 125

Met Gly Arg Ala Glu Met Thr Arg Ala Val Asn Asp Leu Ala Lys Lys
       130                 135                 140

Lys Lys Ala Ala Ala Ala Ala Asp Pro Gln Ala Asp Thr Lys Ser Lys
145                 150                 155                 160

Leu Val Lys Leu Val Val Met Val Cys Glu Gly Leu Arg Phe Asn Thr
                165                 170                 175

Val Ser Arg Thr Val Asp Ala Gly Phe Asn Ser Gln His Gly Val Thr
           180                 185                 190

Leu Thr Val Thr Gln Gly Lys Gln Val Gln Lys Trp Asp Arg Ile Ser
       195                 200                 205

Lys Ala Ala Phe Glu Trp Ala Asp His Pro Thr Ala Val Ile Pro Asp
210                 215                 220
```

```
Met  Gln  Lys  Leu  Gly  Ile  Lys  Asp  Lys  Asn  Glu  Ala  Ala  Arg  Ile  Val
225                 230                 235                           240

Ala  Leu  Val  Lys  Asn  Gln  Thr  Thr  Ala  Ala  Ala  Ala  Thr  Ala  Gly  Ser
                    245                 250                      255

Ala
```

( 2 ) INFORMATION FOR SEQ ID NO:14:

( i ) SEQUENCE CHARACTERISTICS:
        ( A ) LENGTH: 1161 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..998

( x i ) SEQUENCE DESCRIPTION: SEQ ID NO:14:

```
TCCCTCTAGA  TGCGGCCTAA  TTAATTAAGC  TTAAAAGGAG  GAAAAAATT  ATG  AAA         56
                                                           Met  Lys
                                                            1

AGA  ATA  GTG  CCA  AAG  TTC  ACT  GAA  ATC  TTC  CCC  GTG  GAG  GAC  GCG  AAC    104
Arg  Ile  Val  Pro  Lys  Phe  Thr  Glu  Ile  Phe  Pro  Val  Glu  Asp  Ala  Asn
               5                   10                       15

TAC  CCT  TAC  AGC  GCC  TTC  ATC  GCG  TCG  GTC  CGG  AAA  GAC  GTG  ATC  AAA    152
Tyr  Pro  Tyr  Ser  Ala  Phe  Ile  Ala  Ser  Val  Arg  Lys  Asp  Val  Ile  Lys
          20                        25                      30

CAC  TGC  ACC  GAC  CAT  AAA  GGG  ATC  TTC  CAG  CCC  GTG  CTG  CCA  CCG  GAG    200
His  Cys  Thr  Asp  His  Lys  Gly  Ile  Phe  Gln  Pro  Val  Leu  Pro  Pro  Glu
35                       40                       45                       50

AAG  AAG  GTC  CCG  GAG  CTA  TGG  TTC  TAC  ACA  GAG  CTC  AAA  ACT  AGG  ACC    248
Lys  Lys  Val  Pro  Glu  Leu  Trp  Phe  Tyr  Thr  Glu  Leu  Lys  Thr  Arg  Thr
                         55                  60                       65

AGC  TCC  ATC  ACG  CTC  GCC  ATA  CGC  ATG  GAC  AAC  CTG  TAC  CTC  GTG  GGC    296
Ser  Ser  Ile  Thr  Leu  Ala  Ile  Arg  Met  Asp  Asn  Leu  Tyr  Leu  Val  Gly
               70                        75                       80

TTC  AGG  ACC  CCG  GGC  GGG  GTG  TGG  TGG  GAG  TTC  GGC  AAG  GAC  GGC  GAC    344
Phe  Arg  Thr  Pro  Gly  Gly  Val  Trp  Trp  Glu  Phe  Gly  Lys  Asp  Gly  Asp
          85                        90                       95

ACC  CAC  CTC  CTC  GGC  GAC  AAC  CCC  AGG  TGG  CTC  GGC  TTC  GGC  GGC  AGG    392
Thr  His  Leu  Leu  Gly  Asp  Asn  Pro  Arg  Trp  Leu  Gly  Phe  Gly  Gly  Arg
     100                      105                      110

TAC  CAG  GAC  CTC  ATC  GGC  AAC  AAG  GGT  CTG  GAG  ACC  GTC  ACC  ATG  GGC    440
Tyr  Gln  Asp  Leu  Ile  Gly  Asn  Lys  Gly  Leu  Glu  Thr  Val  Thr  Met  Gly
115                      120                      125                      130

CGC  GCC  GAA  ATG  ACC  AGG  GCC  GTC  AAC  GAC  CTG  GCG  AAG  AAG  AAG  AAG    488
Arg  Ala  Glu  Met  Thr  Arg  Ala  Val  Asn  Asp  Leu  Ala  Lys  Lys  Lys  Lys
                    135                      140                      145

GCG  GCT  GAC  CCA  CAG  GCC  GAC  ACG  AAG  AGC  AAG  CTG  GTG  AAG  CTG  GTG    536
Ala  Ala  Asp  Pro  Gln  Ala  Asp  Thr  Lys  Ser  Lys  Leu  Val  Lys  Leu  Val
               150                      155                      160

GTC  ATG  GTG  TGC  GAG  GGG  CTG  CGG  TTC  AAC  ACC  GTG  TCC  CGC  ACG  GTG    584
Val  Met  Val  Cys  Glu  Gly  Leu  Arg  Phe  Asn  Thr  Val  Ser  Arg  Thr  Val
          165                      170                      175

GAC  GCG  GGG  TTC  AAC  AGC  CAG  CAC  GGG  GTG  ACC  TTG  ACC  GTG  ACG  CAG    632
Asp  Ala  Gly  Phe  Asn  Ser  Gln  His  Gly  Val  Thr  Leu  Thr  Val  Thr  Gln
     180                      185                      190

GGG  AAG  CAG  GTG  CAG  AAG  TGG  GAC  AGG  ATC  TCC  AAG  GCG  GCC  TTC  GAG    680
Gly  Lys  Gln  Val  Gln  Lys  Trp  Asp  Arg  Ile  Ser  Lys  Ala  Ala  Phe  Glu
195                      200                      205                      210

TGG  GCT  GAC  CAC  CCC  ACC  GCT  GTG  ATC  CCC  GAC  ATG  CAG  AAG  CTT  GGC    728
```

| | | | | | | | | | | | | | | |
|---|---|---|---|---|---|---|---|---|---|---|---|---|---|---|
| Trp | Ala | Asp | His | Pro | Thr | Ala | Val | Ile | Pro | Asp | Met | Gln | Lys | Leu | Gly |
| | | | | 215 | | | | | 220 | | | | | 225 | |

```
ATC AAG GAT AAG AAC GAA GCA GCG AGG ATC GTT GCG CTC GTT AAG AAT     776
Ile Lys Asp Lys Asn Glu Ala Ala Arg Ile Val Ala Leu Val Lys Asn
            230                 235                 240

CAA ACT ACT GCC GCT GCC GCT ACT GCT GGA TCC GCT GAT AAC AAT TTC     824
Gln Thr Thr Ala Ala Ala Ala Thr Ala Gly Ser Ala Asp Asn Asn Phe
            245                 250                 255

AAC AAA GAA CAA CAA AAT GCT TTC TAT GAA ATC TTG AAT ATG CCT AAC     872
Asn Lys Glu Gln Gln Asn Ala Phe Tyr Glu Ile Leu Asn Met Pro Asn
            260                 265                 270

TTA AAC GAA GAA CAA CGC AAT GGT TTC ATC CAA AGC TTA AAA GAT GAC     920
Leu Asn Glu Glu Gln Arg Asn Gly Phe Ile Gln Ser Leu Lys Asp Asp
275                 280                 285                 290

CCA AGC CAA AGT GCT AAC CTA TTG TCA GAA GCT AAA AAG TTA AAT GAA     968
Pro Ser Gln Ser Ala Asn Leu Leu Ser Glu Ala Lys Lys Leu Asn Glu
                295                 300                 305

TCT CAA GCA CCG AAA GAT CGA TCC GCC TGATCAATGC AACGACACAT          1015
Ser Gln Ala Pro Lys Asp Arg Ser Ala
            310                 315

CATGATCTGC TGCTGCACTT AATTACTATG TTCGTATACA AATAAATACA CCCGGCGTAC  1075

GCGGTGTTCC TTATATGGTC TAAAATGTAG CCAGTAAATT TTAAACTACT TTCTCGTGCC  1135

GAATTCACTG GCCGGCATGC TATATA                                      1161
```

( 2 ) INFORMATION FOR SEQ ID NO:15:

( i ) SEQUENCE CHARACTERISTICS:
        ( A ) LENGTH: 315 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met Lys Arg Ile Val Pro Lys Phe Thr Glu Ile Phe Pro Val Glu Asp
 1               5                  10                  15

Ala Asn Tyr Pro Tyr Ser Ala Phe Ile Ala Ser Val Arg Lys Asp Val
                20                  25                  30

Ile Lys His Cys Thr Asp His Lys Gly Ile Phe Gln Pro Val Leu Pro
                35                  40                  45

Pro Glu Lys Lys Val Pro Glu Leu Trp Phe Tyr Thr Glu Leu Lys Thr
        50                  55                  60

Arg Thr Ser Ser Ile Thr Leu Ala Ile Arg Met Asp Asn Leu Tyr Leu
65                  70                  75                  80

Val Gly Phe Arg Thr Pro Gly Gly Val Trp Trp Glu Phe Gly Lys Asp
                85                  90                  95

Gly Asp Thr His Leu Leu Gly Asp Asn Pro Arg Trp Leu Gly Phe Gly
                100                 105                 110

Gly Arg Tyr Gln Asp Leu Ile Gly Asn Lys Gly Leu Glu Thr Val Thr
                115                 120                 125

Met Gly Arg Ala Glu Met Thr Arg Ala Val Asn Asp Leu Ala Lys Lys
        130                 135                 140

Lys Lys Ala Ala Asp Pro Gln Ala Asp Thr Lys Ser Lys Leu Val Lys
145                 150                 155                 160

Leu Val Val Met Val Cys Glu Gly Leu Arg Phe Asn Thr Val Ser Arg
                165                 170                 175

Thr Val Asp Ala Gly Phe Asn Ser Gln His Gly Val Thr Leu Thr Val
                180                 185                 190
```

```
Thr  Gln  Gly  Lys  Gln  Val  Gln  Lys  Trp  Asp  Arg  Ile  Ser  Lys  Ala  Ala
          195                      200                     205

Phe  Glu  Trp  Ala  Asp  His  Pro  Thr  Ala  Val  Ile  Pro  Asp  Met  Gln  Lys
          210                      215                     220

Leu  Gly  Ile  Lys  Asp  Lys  Asn  Glu  Ala  Ala  Arg  Ile  Val  Ala  Leu  Val
225                      230                     235                          240

Lys  Asn  Gln  Thr  Thr  Ala  Ala  Ala  Ala  Thr  Ala  Gly  Ser  Ala  Asp  Asn
                    245                     250                     255

Asn  Phe  Asn  Lys  Glu  Gln  Gln  Asn  Ala  Phe  Tyr  Glu  Ile  Leu  Asn  Met
                260                      265                     270

Pro  Asn  Leu  Asn  Glu  Glu  Gln  Arg  Asn  Gly  Phe  Ile  Gln  Ser  Leu  Lys
               275                      280                     285

Asp  Asp  Pro  Ser  Gln  Ser  Ala  Asn  Leu  Leu  Ser  Glu  Ala  Lys  Lys  Leu
          290                      295                     300

Asn  Glu  Ser  Gln  Ala  Pro  Lys  Asp  Arg  Ser  Ala
305                      310                     315
```

(2) INFORMATION FOR SEQ ID NO:16:

(i) SEQUENCE CHARACTERISTICS:
        (A) LENGTH: 1422 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 51..1256

(xi) SEQUENCE DESCRIPTION: SEQ ID NO:16:

```
TCCCTCTAGA  TGCGGCCTAA  TTAATTAAGC  TTAAAAGGAG  GAAAAAAATT  ATG  AAA        56
                                                            Met  Lys
                                                              1

AGA  ATA  GTG  CCA  AAG  TTC  ACT  GAA  ATC  TTC  CCC  GTG  GAG  GAC  GCG  AAC       104
Arg  Ile  Val  Pro  Lys  Phe  Thr  Glu  Ile  Phe  Pro  Val  Glu  Asp  Ala  Asn
           5                        10                       15

TAC  CCT  TAC  AGC  GCC  TTC  ATC  GCG  TCG  GTC  CGG  AAA  GAC  GTG  ATC  AAA       152
Tyr  Pro  Tyr  Ser  Ala  Phe  Ile  Ala  Ser  Val  Arg  Lys  Asp  Val  Ile  Lys
      20                        25                      30

CAC  TGC  ACC  GAC  CAT  AAA  GGG  ATC  TTC  CAG  CCC  GTG  CTG  CCA  CCG  GAG       200
His  Cys  Thr  Asp  His  Lys  Gly  Ile  Phe  Gln  Pro  Val  Leu  Pro  Pro  Glu
 35                      40                       45                          50

AAG  AAG  GTC  CCG  GAG  CTA  TGG  TTC  TAC  ACA  GAG  CTC  AAA  ACT  AGG  ACC       248
Lys  Lys  Val  Pro  Glu  Leu  Trp  Phe  Tyr  Thr  Glu  Leu  Lys  Thr  Arg  Thr
                     55                      60                       65

AGC  TCC  ATC  ACG  CTC  GCC  ATA  CGC  ATG  GAC  AAC  CTG  TAC  CTC  GTG  GGC       296
Ser  Ser  Ile  Thr  Leu  Ala  Ile  Arg  Met  Asp  Asn  Leu  Tyr  Leu  Val  Gly
                70                      75                       80

TTC  AGG  ACC  CCG  GGC  GGG  GTG  TGG  TGG  GAG  TTC  GGC  AAG  GAC  GGC  GAC       344
Phe  Arg  Thr  Pro  Gly  Gly  Val  Trp  Trp  Glu  Phe  Gly  Lys  Asp  Gly  Asp
           85                      90                        95

ACC  CAC  CTC  CTC  GGC  GAC  AAC  CCC  AGG  TGG  CTC  GGC  TTC  GGC  GGC  AGG       392
Thr  His  Leu  Leu  Gly  Asp  Asn  Pro  Arg  Trp  Leu  Gly  Phe  Gly  Gly  Arg
     100                      105                      110

TAC  CAG  GAC  CTC  ATC  GGC  AAC  AAG  GGT  CTG  GAG  ACC  GTC  ACC  ATG  GGC       440
Tyr  Gln  Asp  Leu  Ile  Gly  Asn  Lys  Gly  Leu  Glu  Thr  Val  Thr  Met  Gly
115                      120                      125                         130

CGC  GCC  GAA  ATG  ACC  AGG  GCC  GTC  AAC  GAC  CTG  GCG  AAG  AAG  AAG  AAG       488
Arg  Ala  Glu  Met  Thr  Arg  Ala  Val  Asn  Asp  Leu  Ala  Lys  Lys  Lys  Lys
                    135                      140                     145
```

| | | | | | | | | | | | | | | | | |
|---|---|---|---|---|---|---|---|---|---|---|---|---|---|---|---|---|
| GCG | GCT | GAC | CCA | CAG | GCC | GAC | ACG | AAG | AGC | AAG | CTG | GTG | AAG | CTG | GTG | 536 |
| Ala | Ala | Asp | Pro 150 | Gln | Ala | Asp | Thr | Lys 155 | Ser | Lys | Leu | Val | Lys 160 | Leu | Val | |
| GTC | ATG | GTG | TGC | GAG | GGG | CTG | CGG | TTC | AAC | ACC | GTG | TCC | CGC | ACG | GTG | 584 |
| Val | Met | Val 165 | Cys | Glu | Gly | Leu | Arg 170 | Phe | Asn | Thr | Val | Ser 175 | Arg | Thr | Val | |
| GAC | GCG | GGG | TTC | AAC | AGC | CAG | CAC | GGG | GTG | ACC | TTG | ACC | GTG | ACG | CAG | 632 |
| Asp | Ala 180 | Gly | Phe | Asn | Ser | Gln | His 185 | Gly | Val | Thr | Leu | Thr 190 | Val | Thr | Gln | |
| GGG | AAG | CAG | GTG | CAG | AAG | TGG | GAC | AGG | ATC | TCC | AAG | GCG | GCC | TTC | GAG | 680 |
| Gly 195 | Lys | Gln | Val | Gln | Lys 200 | Trp | Asp | Arg | Ile | Ser 205 | Lys | Ala | Ala | Phe | Glu 210 | |
| TGG | GCT | GAC | CAC | CCC | ACC | GCT | GTG | ATC | CCC | GAC | ATG | CAG | AAG | CTT | GGC | 728 |
| Trp | Ala | Asp | His | Pro 215 | Thr | Ala | Val | Ile | Pro 220 | Asp | Met | Gln | Lys | Leu 225 | Gly | |
| ATC | AAG | GAT | AAG | AAC | GAA | GCA | GCG | AGG | ATC | GTT | GCG | CTC | GTT | AAG | AAT | 776 |
| Ile | Lys | Asp | Lys 230 | Asn | Glu | Ala | Ala | Arg 235 | Ile | Val | Ala | Leu | Val 240 | Lys | Asn | |
| CAA | ACT | ACT | GCC | GCT | GCC | GCT | ACT | GCT | GGA | TCC | AAA | CCA | GAA | GTG | ATC | 824 |
| Gln | Thr | Thr 245 | Ala | Ala | Ala | Ala | Thr 250 | Ala | Gly | Ser | Lys | Pro 255 | Glu | Val | Ile | |
| GAT | GCG | TCT | GAA | TTA | ACA | CCA | GCC | GTG | ACA | ACT | TAC | AAA | CTT | GTT | ATT | 872 |
| Asp | Ala | Ser | Glu 260 | Leu | Thr | Pro | Ala | Val 265 | Thr | Thr | Tyr | Lys | Leu 270 | Val | Ile | |
| AAT | GGT | AAA | ACA | TTG | AAA | GGC | GAA | ACA | ACT | ACT | GAA | GCT | GTT | GAT | GCT | 920 |
| Asn | Gly | Lys | Thr 275 | Leu | Lys | Gly | Glu | Thr 280 | Thr | Thr | Glu | Ala | Val 285 | Asp | Ala 290 | |
| GCT | ACT | GCA | GAA | AAA | GTC | TTC | AAA | CAA | TAC | GCT | AAC | GAC | AAC | GGT | GTT | 968 |
| Ala | Thr | Ala | Glu | Lys 295 | Val | Phe | Lys | Gln | Tyr 300 | Ala | Asn | Asp | Asn | Gly 305 | Val | |
| GAC | GGT | GAA | TGG | ACT | TAC | GAC | GAT | GCG | ACT | AAG | ACC | TTT | ACA | GTT | ACT | 1016 |
| Asp | Gly | Glu | Trp 310 | Thr | Tyr | Asp | Asp | Ala 315 | Thr | Lys | Thr | Phe | Thr 320 | Val | Thr | |
| GAA | AAA | CCA | GAA | GTG | ATC | GAT | GCG | TCT | GAA | TTA | ACA | CCA | GCC | GTG | ACA | 1064 |
| Glu | Lys | Pro 325 | Glu | Val | Ile | Asp | Ala 330 | Ser | Glu | Leu | Thr | Pro 335 | Ala | Val | Thr | |
| AGA | TCC | GCT | GAT | AAC | AAT | TTC | AAC | AAA | GAA | CAA | CAA | AAT | GCT | TTC | TAT | 1112 |
| Arg | Ser 340 | Ala | Asp | Asn | Asn | Phe 345 | Asn | Lys | Glu | Gln | Gln 350 | Asn | Ala | Phe | Tyr | |
| GAA | ATC | TTG | AAT | ATG | CCT | AAC | TTA | AAC | GAA | GAA | CAA | CGC | AAT | GGT | TTC | 1160 |
| Glu | Ile | Leu | Asn 355 | Met | Pro | Asn | Leu | Asn 360 | Glu | Glu | Gln | Arg | Asn 365 | Gly | Phe 370 | |
| ATC | CAA | AGC | TTA | AAA | GAT | GAC | CCA | AGC | CAA | AGT | GCT | AAC | CTA | TTG | TCA | 1208 |
| Ile | Gln | Ser | Leu | Lys 375 | Asp | Asp | Pro | Ser | Gln 380 | Ser | Ala | Asn | Leu | Leu 385 | Ser | |
| GAA | GCT | AAA | AAG | TTA | AAT | GAA | TCT | CAA | GCA | CCG | AAA | GAT | CGA | TCC | GCC | 1256 |
| Glu | Ala | Lys | Lys | Leu 390 | Asn | Glu | Ser | Gln | Ala 395 | Pro | Lys | Asp | Arg | Ser 400 | Ala | |

```
TGATCAATGC AACGACACAT CATGATCTGC TGCTGCACTT AATTACTATG TTCGTATACA     1316
AATAAATACA CCCGGCGTAC GCGGTGTTCC TTATATGGTC TAAAATGTAG CCAGTAAATT     1376
TTAAACTACT TTCTCGTGCC GAATTCACTG GCCGGCATGC TATATA                   1422
```

( 2 ) INFORMATION FOR SEQ ID NO:17:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met Lys Arg Ile Val Pro Lys Phe Thr Glu Ile Phe Pro Val Glu Asp
 1               5                  10                 15

Ala Asn Tyr Pro Tyr Ser Ala Phe Ile Ala Ser Val Arg Lys Asp Val
             20                  25                 30

Ile Lys His Cys Thr Asp His Lys Gly Ile Phe Gln Pro Val Leu Pro
         35                  40                 45

Pro Glu Lys Lys Val Pro Glu Leu Trp Phe Tyr Thr Glu Leu Lys Thr
     50                  55                 60

Arg Thr Ser Ser Ile Thr Leu Ala Ile Arg Met Asp Asn Leu Tyr Leu
 65              70                 75                         80

Val Gly Phe Arg Thr Pro Gly Gly Val Trp Trp Glu Phe Gly Lys Asp
             85                  90                 95

Gly Asp Thr His Leu Leu Gly Asp Asn Pro Arg Trp Leu Gly Phe Gly
            100                 105                110

Gly Arg Tyr Gln Asp Leu Ile Gly Asn Lys Gly Leu Glu Thr Val Thr
            115                 120                125

Met Gly Arg Ala Glu Met Thr Arg Ala Val Asn Asp Leu Ala Lys Lys
        130             135                 140

Lys Lys Ala Ala Asp Pro Gln Ala Asp Thr Lys Ser Lys Leu Val Lys
145                 150                 155                160

Leu Val Val Met Val Cys Glu Gly Leu Arg Phe Asn Thr Val Ser Arg
                165                 170                 175

Thr Val Asp Ala Gly Phe Asn Ser Gln His Gly Val Thr Leu Thr Val
            180                 185                 190

Thr Gln Gly Lys Gln Val Gln Lys Trp Asp Arg Ile Ser Lys Ala Ala
        195                 200                 205

Phe Glu Trp Ala Asp His Pro Thr Ala Val Ile Pro Asp Met Gln Lys
    210                 215                 220

Leu Gly Ile Lys Asp Lys Asn Glu Ala Ala Arg Ile Val Ala Leu Val
225                 230                 235                 240

Lys Asn Gln Thr Thr Ala Ala Ala Ala Thr Ala Gly Ser Lys Pro Glu
            245                 250                 255

Val Ile Asp Ala Ser Glu Leu Thr Pro Ala Val Thr Thr Tyr Lys Leu
            260                 265                 270

Val Ile Asn Gly Lys Thr Leu Lys Gly Glu Thr Thr Thr Glu Ala Val
            275                 280                 285

Asp Ala Ala Thr Ala Glu Lys Val Phe Lys Gln Tyr Ala Asn Asp Asn
290                 295                 300

Gly Val Asp Gly Glu Trp Thr Tyr Asp Asp Ala Thr Lys Thr Phe Thr
305                 310                 315                 320

Val Thr Glu Lys Pro Glu Val Ile Asp Ala Ser Glu Leu Thr Pro Ala
            325                 330                 335

Val Thr Arg Ser Ala Asp Asn Asn Phe Asn Lys Glu Gln Gln Asn Ala
            340                 345                 350

Phe Tyr Glu Ile Leu Asn Met Pro Asn Leu Asn Glu Glu Gln Arg Asn
        355                 360                 365

Gly Phe Ile Gln Ser Leu Lys Asp Asp Pro Ser Gln Ser Ala Asn Leu
    370                 375                 380

Leu Ser Glu Ala Lys Lys Leu Asn Glu Ser Gln Ala Pro Lys Asp Arg
385                 390                 395                 400

Ser Ala
```

5,635,384

67 68

-continued ( 2 ) INFORMATION FOR SEQ ID NO:18:

( i ) SEQUENCE CHARACTERISTICS:
        ( A ) LENGTH: 1683 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..1520

( x i ) SEQUENCE DESCRIPTION: SEQ ID NO:18:

```
TCCCTCTAGA TGCGGCCTAA TTAATTAAGC TTAAAAGGAG GAAAAAAATT ATG AAA            56
                                                        Met Lys
                                                         1

AGA ATA GTG CCA AAG TTC ACT GAA ATC TTC CCC GTG GAG GAC GCG AAC         104
Arg Ile Val Pro Lys Phe Thr Glu Ile Phe Pro Val Glu Asp Ala Asn
         5              10              15

TAC CCT TAC AGC GCC TTC ATC GCG TCG GTC CGG AAA GAC GTG ATC AAA         152
Tyr Pro Tyr Ser Ala Phe Ile Ala Ser Val Arg Lys Asp Val Ile Lys
     20              25              30

CAC TGC ACC GAC CAT AAA GGG ATC TTC CAG CCC GTG CTG CCA CCG GAG         200
His Cys Thr Asp His Lys Gly Ile Phe Gln Pro Val Leu Pro Pro Glu
 35              40              45              50

AAG AAG GTC CCG GAG CTA TGG TTC TAC ACA GAG CTC AAA ACT AGG ACC         248
Lys Lys Val Pro Glu Leu Trp Phe Tyr Thr Glu Leu Lys Thr Arg Thr
                 55              60              65

AGC TCC ATC ACG CTC GCC ATA CGC ATG GAC AAC CTG TAC CTC GTG GGC         296
Ser Ser Ile Thr Leu Ala Ile Arg Met Asp Asn Leu Tyr Leu Val Gly
             70              75              80

TTC AGG ACC CCG GGC GGG GTG TGG TGG GAG TTC GGC AAG GAC GGC GAC         344
Phe Arg Thr Pro Gly Gly Val Trp Trp Glu Phe Gly Lys Asp Gly Asp
         85              90              95

ACC CAC CTC CTC GGC GAC AAC CCC AGG TGG CTC GGC TTC GGC GGC AGG         392
Thr His Leu Leu Gly Asp Asn Pro Arg Trp Leu Gly Phe Gly Gly Arg
100             105             110

TAC CAG GAC CTC ATC GGC AAC AAG GGT CTG GAG ACC GTC ACC ATG GGC         440
Tyr Gln Asp Leu Ile Gly Asn Lys Gly Leu Glu Thr Val Thr Met Gly
115             120             125             130

CGC GCC GAA ATG ACC AGG GCC GTC AAC GAC CTG GCG AAG AAG AAG AAG         488
Arg Ala Glu Met Thr Arg Ala Val Asn Asp Leu Ala Lys Lys Lys Lys
                135             140             145

GCG GCT GAC CCA CAG GCC GAC ACG AAG AGC AAG CTG GTG AAG CTG GTG         536
Ala Ala Asp Pro Gln Ala Asp Thr Lys Ser Lys Leu Val Lys Leu Val
            150             155             160

GTC ATG GTG TGC GAG GGG CTG CGG TTC AAC ACC GTG TCC CGC ACG GTG         584
Val Met Val Cys Glu Gly Leu Arg Phe Asn Thr Val Ser Arg Thr Val
        165             170             175

GAC GCG GGG TTC AAC AGC CAG CAC GGG GTG ACC TTG ACC GTG ACG CAG         632
Asp Ala Gly Phe Asn Ser Gln His Gly Val Thr Leu Thr Val Thr Gln
    180             185             190

GGG AAG CAG GTG CAG AAG TGG GAC AGG ATC TCC AAG GCG GCC TTC GAG         680
Gly Lys Gln Val Gln Lys Trp Asp Arg Ile Ser Lys Ala Ala Phe Glu
195             200             205             210

TGG GCT GAC CAC CCC ACC GCT GTG ATC CCC GAC ATG CAG AAG CTT GGC         728
Trp Ala Asp His Pro Thr Ala Val Ile Pro Asp Met Gln Lys Leu Gly
                215             220             225

ATC AAG GAT AAG AAC GAA GCA GCG AGG ATC GTT GCG CTC GTT AAG AAT         776
Ile Lys Asp Lys Asn Glu Ala Ala Arg Ile Val Ala Leu Val Lys Asn
            230             235             240

CAA ACT ACT GCC GCT GCC GCT ACT GCT GGA TCC AAA CCA GAA GTG ATC         824
Gln Thr Thr Ala Ala Ala Ala Thr Ala Gly Ser Lys Pro Glu Val Ile
```

-continued

| | | | 245 | | | | 250 | | | | 255 | | | | | |
|---|---|---|---|---|---|---|---|---|---|---|---|---|---|---|---|---|
| GAT | GCG | TCT | GAA | TTA | ACA | CCA | GCC | GTG | ACA | ACT | TAC | AAA | CTT | GTT | ATT | 872 |
| Asp | Ala | Ser | Glu | Leu | Thr | Pro | Ala | Val | Thr | Thr | Tyr | Lys | Leu | Val | Ile | |
| 260 | | | | | 265 | | | | | | 270 | | | | | |
| AAT | GGT | AAA | ACA | TTG | AAA | GGC | GAA | ACA | ACT | ACT | GAA | GCT | GTT | GAT | GCT | 920 |
| Asn | Gly | Lys | Thr | Leu | Lys | Gly | Glu | Thr | Thr | Thr | Glu | Ala | Val | Asp | Ala | |
| 275 | | | | | 280 | | | | | 285 | | | | | 290 | |
| GCT | ACT | GCA | GAA | AAA | GTC | TTC | AAA | CAA | TAC | GCT | AAC | GAC | AAC | GGT | GTT | 968 |
| Ala | Thr | Ala | Glu | Lys | Val | Phe | Lys | Gln | Tyr | Ala | Asn | Asp | Asn | Gly | Val | |
| | | | | 295 | | | | | 300 | | | | | 305 | | |
| GAC | GGT | GAA | TGG | ACT | TAC | GAC | GAT | GCG | ACT | AAG | ACC | TTT | ACA | GTT | ACT | 1016 |
| Asp | Gly | Glu | Trp | Thr | Tyr | Asp | Asp | Ala | Thr | Lys | Thr | Phe | Thr | Val | Thr | |
| | | | 310 | | | | | 315 | | | | | 320 | | | |
| GAA | AAA | CCA | GAA | GTG | ATC | GAT | GCG | TCT | GAA | TTA | ACA | CCA | GCC | GTG | ACA | 1064 |
| Glu | Lys | Pro | Glu | Val | Ile | Asp | Ala | Ser | Glu | Leu | Thr | Pro | Ala | Val | Thr | |
| | | 325 | | | | | 330 | | | | | 335 | | | | |
| AGA | TCC | AAA | CCA | GAA | GTG | ATC | GAT | GCG | TCT | GAA | TTA | ACA | CCA | GCC | GTG | 1112 |
| Arg | Ser | Lys | Pro | Glu | Val | Ile | Asp | Ala | Ser | Glu | Leu | Thr | Pro | Ala | Val | |
| | 340 | | | | | 345 | | | | | 350 | | | | | |
| ACA | ACT | TAC | AAA | CTT | GTT | ATT | AAT | GGT | AAA | ACA | TTG | AAA | GGC | GAA | ACA | 1160 |
| Thr | Thr | Tyr | Lys | Leu | Val | Ile | Asn | Gly | Lys | Thr | Leu | Lys | Gly | Glu | Thr | |
| 355 | | | | | 360 | | | | | 365 | | | | | 370 | |
| ACT | ACT | GAA | GCT | GTT | GAT | GCT | GCT | ACT | GCA | GAA | AAA | GTC | TTC | AAA | CAA | 1208 |
| Thr | Thr | Glu | Ala | Val | Asp | Ala | Ala | Thr | Ala | Glu | Lys | Val | Phe | Lys | Gln | |
| | | | | 375 | | | | | 380 | | | | | 385 | | |
| TAC | GCT | AAC | GAC | AAC | GGT | GTT | GAC | GGT | GAA | TGG | ACT | TAC | GAC | GAT | GCG | 1256 |
| Tyr | Ala | Asn | Asp | Asn | Gly | Val | Asp | Gly | Glu | Trp | Thr | Tyr | Asp | Asp | Ala | |
| | | | 390 | | | | | 395 | | | | | 400 | | | |
| ACT | AAG | ACC | TTT | ACA | GTT | ACT | GAA | AAA | CCA | GAA | GTG | ATC | GAT | GCG | TCT | 1304 |
| Thr | Lys | Thr | Phe | Thr | Val | Thr | Glu | Lys | Pro | Glu | Val | Ile | Asp | Ala | Ser | |
| | | 405 | | | | | 410 | | | | | 415 | | | | |
| GAA | TTA | ACA | CCA | GCC | GTG | ACA | AGA | TCC | GCT | GAT | AAC | AAT | TTC | AAC | AAA | 1352 |
| Glu | Leu | Thr | Pro | Ala | Val | Thr | Arg | Ser | Ala | Asp | Asn | Asn | Phe | Asn | Lys | |
| | 420 | | | | | 425 | | | | | 430 | | | | | |
| GAA | CAA | CAA | AAT | GCT | TTC | TAT | GAA | ATC | TTG | AAT | ATG | CCT | AAC | TTA | AAC | 1400 |
| Glu | Gln | Gln | Asn | Ala | Phe | Tyr | Glu | Ile | Leu | Asn | Met | Pro | Asn | Leu | Asn | |
| 435 | | | | | 440 | | | | | 445 | | | | | 450 | |
| GAA | GAA | CAA | CGC | AAT | GGT | TTC | ATC | CAA | AGC | TTA | AAA | GAT | GAC | CCA | AGC | 1448 |
| Glu | Glu | Gln | Arg | Asn | Gly | Phe | Ile | Gln | Ser | Leu | Lys | Asp | Asp | Pro | Ser | |
| | | | | 455 | | | | | 460 | | | | | 465 | | |
| CAA | AGT | GCT | AAC | CTA | TTG | TCA | GAA | GCT | AAA | AAG | TTA | AAT | GAA | TCT | CAA | 1496 |
| Gln | Ser | Ala | Asn | Leu | Leu | Ser | Glu | Ala | Lys | Lys | Leu | Asn | Glu | Ser | Gln | |
| | | | 470 | | | | | 475 | | | | | 480 | | | |
| GCA | CCG | AAA | GAT | CGA | TCC | GCC | TGATCAATGC | AACGACACAT | CATGATCTGC | | | | | | | 1547 |
| Ala | Pro | Lys | Asp | Arg | Ser | Ala | | | | | | | | | | |
| | | 485 | | | | 490 | | | | | | | | | | |

TGCTGCACTT AATTACTATG TTCGTATACA AATAAATACA CCCGGCGTAC GCGGTGTTCC 1607

TTATATGGTC TAAAATGTAG CCAGTAAATT TTAAACTACT TTCTCGTGCC GAATTCACTG 1667

GCCGGCATGC TATATA 1683

( 2 ) INFORMATION FOR SEQ ID NO:19:

( i ) SEQUENCE CHARACTERISTICS:
( A ) LENGTH: 489 amino acids
( B ) TYPE: amino acid
( D ) TOPOLOGY: linear ( i i ) MOLECULE TYPE: protein ( x i ) SEQUENCE DESCRIPTION: SEQ ID NO:19:

| | | | | | | | | | | | | | | |
|---|---|---|---|---|---|---|---|---|---|---|---|---|---|---|
| Met 1 | Lys | Arg | Ile | Val 5 | Pro | Lys | Phe | Thr | Glu 10 | Ile | Phe | Pro | Val | Glu Asp 15 |
| Ala | Asn | Tyr | Pro 20 | Tyr | Ser | Ala | Phe | Ile 25 | Ala | Ser | Val | Arg | Lys 30 | Asp Val |
| Ile | Lys | His 35 | Cys | Thr | Asp | His | Lys 40 | Gly | Ile | Phe | Gln | Pro 45 | Val | Leu Pro |
| Pro | Glu 50 | Lys | Lys | Val | Pro | Glu 55 | Leu | Trp | Phe | Tyr | Thr 60 | Glu | Leu | Lys Thr |
| Arg 65 | Thr | Ser | Ser | Ile | Thr 70 | Leu | Ala | Ile | Arg | Met 75 | Asp | Asn | Leu | Tyr Leu 80 |
| Val | Gly | Phe | Arg | Thr 85 | Pro | Gly | Gly | Val | Trp 90 | Trp | Glu | Phe | Gly | Lys Asp 95 |
| Gly | Asp | Thr | His 100 | Leu | Leu | Gly | Asp | Asn 105 | Pro | Arg | Trp | Leu 110 | Gly | Phe Gly |
| Gly | Arg | Tyr 115 | Gln | Asp | Leu | Ile | Gly 120 | Asn | Lys | Gly | Leu | Glu 125 | Thr | Val Thr |
| Met | Gly 130 | Arg | Ala | Glu | Met | Thr 135 | Arg | Ala | Val | Asn | Asp 140 | Leu | Ala | Lys Lys |
| Lys 145 | Lys | Ala | Ala | Asp | Pro 150 | Gln | Ala | Asp | Thr | Lys 155 | Ser | Lys | Leu | Val Lys 160 |
| Leu | Val | Val | Met | Val 165 | Cys | Glu | Gly | Leu | Arg 170 | Phe | Asn | Thr | Val | Ser Arg 175 |
| Thr | Val | Asp | Ala 180 | Gly | Phe | Asn | Ser | Gln 185 | His | Gly | Val | Thr | Leu 190 | Thr Val |
| Thr | Gln | Gly 195 | Lys | Gln | Val | Gln | Lys 200 | Trp | Asp | Arg | Ile | Ser 205 | Lys | Ala Ala |
| Phe | Glu 210 | Trp | Ala | Asp | His | Pro 215 | Thr | Ala | Val | Ile | Pro 220 | Asp | Met | Gln Lys |
| Leu 225 | Gly | Ile | Lys | Asp | Lys 230 | Asn | Glu | Ala | Ala | Arg 235 | Ile | Val | Ala | Leu Val 240 |
| Lys | Asn | Gln | Thr | Thr 245 | Ala | Ala | Ala | Ala | Thr 250 | Ala | Gly | Ser | Lys | Pro Glu 255 |
| Val | Ile | Asp | Ala 260 | Ser | Glu | Leu | Thr | Pro 265 | Ala | Val | Thr | Thr | Tyr 270 | Lys Leu |
| Val | Ile | Asn 275 | Gly | Lys | Thr | Leu | Lys 280 | Gly | Glu | Thr | Thr | Thr 285 | Glu | Ala Val |
| Asp | Ala 290 | Ala | Thr | Ala | Glu | Lys 295 | Val | Phe | Lys | Gln | Tyr 300 | Ala | Asn | Asp Asn |
| Gly 305 | Val | Asp | Gly | Glu | Trp 310 | Thr | Tyr | Asp | Asp | Ala 315 | Thr | Lys | Thr | Phe Thr 320 |
| Val | Thr | Glu | Lys | Pro 325 | Glu | Val | Ile | Asp | Ala 330 | Ser | Glu | Leu | Thr | Pro Ala 335 |
| Val | Thr | Arg | Ser 340 | Lys | Pro | Glu | Val | Ile 345 | Asp | Ala | Ser | Glu | Leu 350 | Thr Pro |
| Ala | Val | Thr 355 | Thr | Tyr | Lys | Leu | Val 360 | Ile | Asn | Gly | Lys | Thr 365 | Leu | Lys Gly |
| Glu | Thr 370 | Thr | Thr | Glu | Ala | Val 375 | Asp | Ala | Ala | Thr | Ala 380 | Glu | Lys | Val Phe |
| Lys 385 | Gln | Tyr | Ala | Asn | Asp 390 | Asn | Gly | Val | Asp | Gly 395 | Glu | Trp | Thr | Tyr Asp 400 |
| Asp | Ala | Thr | Lys | Thr 405 | Phe | Thr | Val | Thr | Glu 410 | Lys | Pro | Glu | Val | Ile Asp 415 |
| Ala | Ser | Glu | Leu 420 | Thr | Pro | Ala | Val | Thr 425 | Arg | Ser | Ala | Asp | Asn 430 | Asn Phe |

```
Asn Lys Glu Gln Gln Asn Ala Phe Tyr Glu Ile Leu Asn Met Pro Asn
        435                 440                 445

Leu Asn Glu Glu Gln Arg Asn Gly Phe Ile Gln Ser Leu Lys Asp Asp
        450                 455                 460

Pro Ser Gln Ser Ala Asn Leu Leu Ser Glu Ala Lys Lys Leu Asn Glu
465                 470                 475                 480

Ser Gln Ala Pro Lys Asp Arg Ser Ala
                485
```

( 2 ) INFORMATION FOR SEQ ID NO:20:

( i ) SEQUENCE CHARACTERISTICS:
        ( A ) LENGTH: 847 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..845

( x i ) SEQUENCE DESCRIPTION: SEQ ID NO:20:

```
TCCCTCTAGA TGCGGCCTAA TTAATTAAGC TTAAAAGGAG GAAAAAAATT ATG AAA          56
                                                     Met Lys
                                                       1

AGA ATA GTG CCA AAG TTC ACT GAA ATC TTC CCC GTG GAG GAC GCG AAC       104
Arg Ile Val Pro Lys Phe Thr Glu Ile Phe Pro Val Glu Asp Ala Asn
          5                  10                  15

TAC CCT TAC AGC GCC TTC ATC GCG TCG GTC CGG AAA GAC GTG ATC AAA       152
Tyr Pro Tyr Ser Ala Phe Ile Ala Ser Val Arg Lys Asp Val Ile Lys
 20                  25                  30

CAC TGC ACC GAC CAT AAA GGG ATC TTC CAG CCC GTG CTG CCA CCG GAG       200
His Cys Thr Asp His Lys Gly Ile Phe Gln Pro Val Leu Pro Pro Glu
 35                  40                  45                  50

AAG AAG GTC CCG GAG CTA TGG TTC TAC ACA GAG CTC AAA ACT AGG ACC       248
Lys Lys Val Pro Glu Leu Trp Phe Tyr Thr Glu Leu Lys Thr Arg Thr
                 55                  60                  65

AGC TCC ATC ACG CTC GCC ATA CGC ATG GAC AAC CTG TAC CTC GTG GGC       296
Ser Ser Ile Thr Leu Ala Ile Arg Met Asp Asn Leu Tyr Leu Val Gly
         70                  75                  80

TTC AGG ACC CCG GGC GGG GTG TGG TGG GAG TTC GGC AAG GAC GGC GAC       344
Phe Arg Thr Pro Gly Gly Val Trp Trp Glu Phe Gly Lys Asp Gly Asp
         85                  90                  95

ACC CAC CTC CTC GGC GAC AAC CCC AGG TGG CTC GGC TTC GGC GGC AGG       392
Thr His Leu Leu Gly Asp Asn Pro Arg Trp Leu Gly Phe Gly Gly Arg
100                 105                 110

TAC CAG GAC CTC ATC GGC AAC AAG GGT CTG GAG ACC GTC ACC ATG GGC       440
Tyr Gln Asp Leu Ile Gly Asn Lys Gly Leu Glu Thr Val Thr Met Gly
115                 120                 125                 130

CGC GCC GAA ATG ACC AGG GCC GTC AAC GAC CTG GCG AAG AAG AAG AAG       488
Arg Ala Glu Met Thr Arg Ala Val Asn Asp Leu Ala Lys Lys Lys Lys
                135                 140                 145

GCG GCT GAC CCA CAG GCC GAC ACG AAG AGC AAG CTG GTG AAG CTG GTG       536
Ala Ala Asp Pro Gln Ala Asp Thr Lys Ser Lys Leu Val Lys Leu Val
                150                 155                 160

GTC ATG GTG TGC GAG GGG CTG CGG TTC AAC ACC GTG TCC CGC ACG GTG       584
Val Met Val Cys Glu Gly Leu Arg Phe Asn Thr Val Ser Arg Thr Val
        165                 170                 175

GAC GCG GGG TTC AAC AGC CAG CAC GGG GTG ACC TTG ACC GTG ACG CAG       632
Asp Ala Gly Phe Asn Ser Gln His Gly Val Thr Leu Thr Val Thr Gln
180                 185                 190
```

```
GGG  AAG  CAG  GTG  CAG  AAG  TGG  GAC  AGG  ATC  TCC  AAG  GCG  GCC  TTC  GAG      680
Gly  Lys  Gln  Val  Gln  Lys  Trp  Asp  Arg  Ile  Ser  Lys  Ala  Ala  Phe  Glu
195                      200                      205                      210

TGG  GCT  GAC  CAC  CCC  ACC  GCT  GTG  ATC  CCC  GAC  ATG  CAG  AAG  CTT  GGC      728
Trp  Ala  Asp  His  Pro  Thr  Ala  Val  Ile  Pro  Asp  Met  Gln  Lys  Leu  Gly
                    215                      220                      225

ATC  AAG  GAT  AAG  AAC  GAA  GCA  GCG  AGG  ATC  GTT  GCG  CTC  GTT  AAG  AAT      776
Ile  Lys  Asp  Lys  Asn  Glu  Ala  Ala  Arg  Ile  Val  Ala  Leu  Val  Lys  Asn
               230                      235                      240

CAA  ACT  ACT  GCC  GCT  GCC  GCT  ACT  GCT  GGA  TCC  GTT  AAC  GTC  GAC  GAA      824
Gln  Thr  Thr  Ala  Ala  Ala  Ala  Thr  Ala  Gly  Ser  Val  Asn  Val  Asp  Glu
          245                      250                      255

TTC  ACT  GGC  CGG  CAT  GCT  ATA  TA                                              847
Phe  Thr  Gly  Arg  His  Ala  Ile
260                      265
```

( 2 ) INFORMATION FOR SEQ ID NO:21:

( i ) SEQUENCE CHARACTERISTICS:
        ( A ) LENGTH: 265 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met  Lys  Arg  Ile  Val  Pro  Lys  Phe  Thr  Glu  Ile  Phe  Pro  Val  Glu  Asp
1                   5                    10                      15

Ala  Asn  Tyr  Pro  Tyr  Ser  Ala  Phe  Ile  Ala  Ser  Val  Arg  Lys  Asp  Val
               20                   25                      30

Ile  Lys  His  Cys  Thr  Asp  His  Lys  Gly  Ile  Phe  Gln  Pro  Val  Leu  Pro
          35                   40                      45

Pro  Glu  Lys  Lys  Val  Pro  Glu  Leu  Trp  Phe  Tyr  Thr  Glu  Leu  Lys  Thr
     50                   55                      60

Arg  Thr  Ser  Ser  Ile  Thr  Leu  Ala  Ile  Arg  Met  Asp  Asn  Leu  Tyr  Leu
65                       70                      75                        80

Val  Gly  Phe  Arg  Thr  Pro  Gly  Gly  Val  Trp  Trp  Glu  Phe  Gly  Lys  Asp
               85                   90                      95

Gly  Asp  Thr  His  Leu  Leu  Gly  Asp  Asn  Pro  Arg  Trp  Leu  Gly  Phe  Gly
               100                  105                     110

Gly  Arg  Tyr  Gln  Asp  Leu  Ile  Gly  Asn  Lys  Gly  Leu  Glu  Thr  Val  Thr
               115                  120                     125

Met  Gly  Arg  Ala  Glu  Met  Thr  Arg  Ala  Val  Asn  Asp  Leu  Ala  Lys  Lys
     130                 135                      140

Lys  Lys  Ala  Ala  Asp  Pro  Gln  Ala  Asp  Thr  Lys  Ser  Lys  Leu  Val  Lys
145                      150                      155                     160

Leu  Val  Val  Met  Val  Cys  Glu  Gly  Leu  Arg  Phe  Asn  Thr  Val  Ser  Arg
                    165                  170                     175

Thr  Val  Asp  Ala  Gly  Phe  Asn  Ser  Gln  His  Gly  Val  Thr  Leu  Thr  Val
               180                  185                     190

Thr  Gln  Gly  Lys  Gln  Val  Gln  Lys  Trp  Asp  Arg  Ile  Ser  Lys  Ala  Ala
          195                  200                      205

Phe  Glu  Trp  Ala  Asp  His  Pro  Thr  Ala  Val  Ile  Pro  Asp  Met  Gln  Lys
     210                 215                      220

Leu  Gly  Ile  Lys  Asp  Lys  Asn  Glu  Ala  Ala  Arg  Ile  Val  Ala  Leu  Val
225                      230                      235                     240

Lys  Asn  Gln  Thr  Thr  Ala  Ala  Ala  Ala  Thr  Ala  Gly  Ser  Val  Asn  Val
                    245                  250                     255
```

```
Asp Glu Phe Thr Gly Arg His Ala Ile
        260                 265

( 2 ) INFORMATION FOR SEQ ID NO:22:

( i ) SEQUENCE CHARACTERISTICS:
          ( A ) LENGTH: 1695 base pairs
          ( B ) TYPE: nucleic acid
          ( C ) STRANDEDNESS: single
          ( D ) TOPOLOGY: linear ( i x ) FEATURE:
          ( A ) NAME/KEY: CDS
          ( B ) LOCATION: 51..1532

( x i ) SEQUENCE DESCRIPTION: SEQ ID NO:22:

TCCCTCTAGA TGCGGCCTAA TTAATTAAGC TTAAAAGGAG GAAAAAAATT ATG AAA          56
                                                         Met Lys
                                                          1

AGA ATA GTG CCA AAG TTC ACT GAA ATC TTC CCC GTG GAG GAC GCG AAC       104
Arg Ile Val Pro Lys Phe Thr Glu Ile Phe Pro Val Glu Asp Ala Asn
         5               10                  15

TAC CCT TAC AGC GCC TTC ATC GCG TCG GTC CGG AAA GAC GTG ATC AAA       152
Tyr Pro Tyr Ser Ala Phe Ile Ala Ser Val Arg Lys Asp Val Ile Lys
     20                  25                  30

CAC TGC ACC GAC CAT AAA GGG ATC TTC CAG CCC GTG CTG CCA CCG GAG       200
His Cys Thr Asp His Lys Gly Ile Phe Gln Pro Val Leu Pro Pro Glu
 35                  40                  45                  50

AAG AAG GTC CCG GAG CTA TGG TTC TAC ACA GAG CTC AAA ACT AGG ACC       248
Lys Lys Val Pro Glu Leu Trp Phe Tyr Thr Glu Leu Lys Thr Arg Thr
             55                  60                  65

AGC TCC ATC ACG CTC GCC ATA CGC ATG GAC AAC CTG TAC CTC GTG GGC       296
Ser Ser Ile Thr Leu Ala Ile Arg Met Asp Asn Leu Tyr Leu Val Gly
             70                  75                  80

TTC AGG ACC CCG GGC GGG GTG TGG TGG GAG TTC GGC AAG GAC GGC GAC       344
Phe Arg Thr Pro Gly Gly Val Trp Trp Glu Phe Gly Lys Asp Gly Asp
             85                  90                  95

ACC CAC CTC CTC GGC GAC AAC CCC AGG TGG CTC GGC TTC GGC GGC AGG       392
Thr His Leu Leu Gly Asp Asn Pro Arg Trp Leu Gly Phe Gly Gly Arg
    100                 105                 110

TAC CAG GAC CTC ATC GGC AAC AAG GGT CTG GAG ACC GTC ACC ATG GGC       440
Tyr Gln Asp Leu Ile Gly Asn Lys Gly Leu Glu Thr Val Thr Met Gly
115                 120                 125                 130

CGC GCC GAA ATG ACC AGG GCC GTC AAC GAC CTG GCG AAG AAG AAG AAG       488
Arg Ala Glu Met Thr Arg Ala Val Asn Asp Leu Ala Lys Lys Lys Lys
                135                 140                 145

GCG GCT GAC CCA CAG GCC GAC ACG AAG AGC AAG CTG GTG AAG CTG GTG       536
Ala Ala Asp Pro Gln Ala Asp Thr Lys Ser Lys Leu Val Lys Leu Val
            150                 155                 160

GTC ATG GTG TGC GAG GGG CTG CGG TTC AAC ACC GTG TCC CGC ACG GTG       584
Val Met Val Cys Glu Gly Leu Arg Phe Asn Thr Val Ser Arg Thr Val
        165                 170                 175

GAC GCG GGG TTC AAC AGC CAG CAC GGG GTG ACC TTG ACC GTG ACG CAG       632
Asp Ala Gly Phe Asn Ser Gln His Gly Val Thr Leu Thr Val Thr Gln
        180                 185                 190

GGG AAG CAG GTG CAG AAG TGG GAC AGG ATC TCC AAG GCG GCC TTC GAG       680
Gly Lys Gln Val Gln Lys Trp Asp Arg Ile Ser Lys Ala Ala Phe Glu
195                 200                 205                 210

TGG GCT GAC CAC CCC ACC GCT GTG ATC CCC GAC ATG CAG AAG CTT GGC       728
Trp Ala Asp His Pro Thr Ala Val Ile Pro Asp Met Gln Lys Leu Gly
                215                 220                 225

ATC AAG GAT AAG AAC GAA GCA GCG AGG ATC GTT GCG CTC GTT AAG AAT       776
Ile Lys Asp Lys Asn Glu Ala Ala Arg Ile Val Ala Leu Val Lys Asn
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 230 |     |     |     |     | 235 |     |     |     |     | 240 |     |     |      |
| CAA | ACT | ACT | GCC | GCT | GCC | GCT | ACT | GCT | GGA | TCC | GTT | AAC | GTC | GAC | AAA | 824  |
| Gln | Thr | Thr | Ala | Ala | Ala | Ala | Thr | Ala | Gly | Ser | Val | Asn | Val | Asp | Lys |      |
|     | 245 |     |     |     |     |     | 250 |     |     |     |     | 255 |     |     |     |      |
| CCA | GAA | GTG | ATC | GAT | GCG | TCT | GAA | TTA | ACA | CCA | GCC | GTG | ACA | ACT | TAC | 872  |
| Pro | Glu | Val | Ile | Asp | Ala | Ser | Glu | Leu | Thr | Pro | Ala | Val | Thr | Thr | Tyr |      |
| 260 |     |     |     |     | 265 |     |     |     |     | 270 |     |     |     |     |     |      |
| AAA | CTT | GTT | ATT | AAT | GGT | AAA | ACA | TTG | AAA | GGC | GAA | ACA | ACT | ACT | GAA | 920  |
| Lys | Leu | Val | Ile | Asn | Gly | Lys | Thr | Leu | Lys | Gly | Glu | Thr | Thr | Thr | Glu |      |
| 275 |     |     |     |     | 280 |     |     |     |     | 285 |     |     |     |     | 290 |      |
| GCT | GTT | GAT | GCT | GCT | ACT | GCA | GAA | AAA | GTC | TTC | AAA | CAA | TAC | GCT | AAC | 968  |
| Ala | Val | Asp | Ala | Ala | Thr | Ala | Glu | Lys | Val | Phe | Lys | Gln | Tyr | Ala | Asn |      |
|     |     |     |     | 295 |     |     |     |     | 300 |     |     |     |     | 305 |     |      |
| GAC | AAC | GGT | GTT | GAC | GGT | GAA | TGG | ACT | TAC | GAC | GAT | GCG | ACT | AAG | ACC | 1016 |
| Asp | Asn | Gly | Val | Asp | Gly | Glu | Trp | Thr | Tyr | Asp | Asp | Ala | Thr | Lys | Thr |      |
|     |     |     | 310 |     |     |     |     | 315 |     |     |     |     | 320 |     |     |      |
| TTT | ACA | GTT | ACT | GAA | AAA | CCA | GAA | GTG | ATC | GAT | GCG | TCT | GAA | TTA | ACA | 1064 |
| Phe | Thr | Val | Thr | Glu | Lys | Pro | Glu | Val | Ile | Asp | Ala | Ser | Glu | Leu | Thr |      |
|     | 325 |     |     |     |     | 330 |     |     |     |     | 335 |     |     |     |     |      |
| CCA | GCC | GTG | ACA | AGA | TCC | AAA | CCA | GAA | GTG | ATC | GAT | GCG | TCT | GAA | TTA | 1112 |
| Pro | Ala | Val | Thr | Arg | Ser | Lys | Pro | Glu | Val | Ile | Asp | Ala | Ser | Glu | Leu |      |
| 340 |     |     |     |     | 345 |     |     |     |     | 350 |     |     |     |     |     |      |
| ACA | CCA | GCC | GTG | ACA | ACT | TAC | AAA | CTT | GTT | ATT | AAT | GGT | AAA | ACA | TTG | 1160 |
| Thr | Pro | Ala | Val | Thr | Thr | Tyr | Lys | Leu | Val | Ile | Asn | Gly | Lys | Thr | Leu |      |
| 355 |     |     |     |     | 360 |     |     |     |     | 365 |     |     |     |     | 370 |      |
| AAA | GGC | GAA | ACA | ACT | ACT | GAA | GCT | GTT | GAT | GCT | GCT | ACT | GCA | GAA | AAA | 1208 |
| Lys | Gly | Glu | Thr | Thr | Thr | Glu | Ala | Val | Asp | Ala | Ala | Thr | Ala | Glu | Lys |      |
|     |     |     |     | 375 |     |     |     |     | 380 |     |     |     |     | 385 |     |      |
| GTC | TTC | AAA | CAA | TAC | GCT | AAC | GAC | AAC | GGT | GTT | GAC | GGT | GAA | TGG | ACT | 1256 |
| Val | Phe | Lys | Gln | Tyr | Ala | Asn | Asp | Asn | Gly | Val | Asp | Gly | Glu | Trp | Thr |      |
|     |     |     | 390 |     |     |     |     | 395 |     |     |     |     | 400 |     |     |      |
| TAC | GAC | GAT | GCG | ACT | AAG | ACC | TTT | ACA | GTT | ACT | GAA | AAA | CCA | GAA | GTG | 1304 |
| Tyr | Asp | Asp | Ala | Thr | Lys | Thr | Phe | Thr | Val | Thr | Glu | Lys | Pro | Glu | Val |      |
|     || 405 |     |     |     |     | 410 |     |     |     |     | 415 |     |     |     |      |
| ATC | GAT | GCG | TCT | GAA | TTA | ACA | CCA | GCC | GTG | ACA | AGA | TCC | GCT | GAT | AAC | 1352 |
| Ile | Asp | Ala | Ser | Glu | Leu | Thr | Pro | Ala | Val | Thr | Arg | Ser | Ala | Asp | Asn |      |
|     | 420 |     |     |     |     | 425 |     |     |     |     | 430 |     |     |     |     |      |
| AAT | TTC | AAC | AAA | GAA | CAA | CAA | AAT | GCT | TTC | TAT | GAA | ATC | TTG | AAT | ATG | 1400 |
| Asn | Phe | Asn | Lys | Glu | Gln | Gln | Asn | Ala | Phe | Tyr | Glu | Ile | Leu | Asn | Met |      |
| 435 |     |     |     |     | 440 |     |     |     |     | 445 |     |     |     |     | 450 |      |
| CCT | AAC | TTA | AAC | GAA | GAA | CAA | CGC | AAT | GGT | TTC | ATC | CAA | AGC | TTA | AAA | 1448 |
| Pro | Asn | Leu | Asn | Glu | Glu | Gln | Arg | Asn | Gly | Phe | Ile | Gln | Ser | Leu | Lys |      |
|     |     |     |     | 455 |     |     |     |     | 460 |     |     |     |     | 465 |     |      |
| GAT | GAC | CCA | AGC | CAA | AGT | GCT | AAC | CTA | TTG | TCA | GAA | GCT | AAA | AAG | TTA | 1496 |
| Asp | Asp | Pro | Ser | Gln | Ser | Ala | Asn | Leu | Leu | Ser | Glu | Ala | Lys | Lys | Leu |      |
|     |     |     | 470 |     |     |     |     | 475 |     |     |     |     | 480 |     |     |      |
| AAT | GAA | TCT | CAA | GCA | CCG | AAA | GAT | CGA | TCC | GCC | TGATCAATGC | AACGACACAT |     |     |     | 1549 |
| Asn | Glu | Ser | Gln | Ala | Pro | Lys | Asp | Arg | Ser | Ala |     |     |     |     |     |      |
|     | 485 |     |     |     |     | 490 |     |     |     |     |     |     |     |     |     |      |

CATGATCTGC TGCTGCACTT AATTACTATG TTCGTATACA AATAAATACA CCCGGCGTAC  1609

GCGGTGTTCC TTATATGGTC TAAAATGTAG CCAGTAAATT TTAAACTACT TTCTCGTGCC  1669

GAATTCACTG GCCGGCATGC TATATA  1695

( 2 ) INFORMATION FOR SEQ ID NO:23:

( i ) SEQUENCE CHARACTERISTICS:
( A ) LENGTH: 493 amino acids
( B ) TYPE: amino acid
( D ) TOPOLOGY: linear ( i i ) MOLECULE TYPE: protein ( x i ) SEQUENCE DESCRIPTION: SEQ ID NO:23:

| Met | Lys | Arg | Ile | Val | Pro | Lys | Phe | Thr | Glu | Ile | Phe | Pro | Val | Glu | Asp |
|---|---|---|---|---|---|---|---|---|---|---|---|---|---|---|---|
| 1 | | | | 5 | | | | | 10 | | | | | 15 | |
| Ala | Asn | Tyr | Pro | Tyr | Ser | Ala | Phe | Ile | Ala | Ser | Val | Arg | Lys | Asp | Val |
| | | | 20 | | | | | 25 | | | | | 30 | | |
| Ile | Lys | His | Cys | Thr | Asp | His | Lys | Gly | Ile | Phe | Gln | Pro | Val | Leu | Pro |
| | | | 35 | | | | 40 | | | | | 45 | | | |
| Pro | Glu | Lys | Lys | Val | Pro | Glu | Leu | Trp | Phe | Tyr | Thr | Glu | Leu | Lys | Thr |
| | | 50 | | | | | 55 | | | | | 60 | | | |
| Arg | Thr | Ser | Ser | Ile | Thr | Leu | Ala | Ile | Arg | Met | Asp | Asn | Leu | Tyr | Leu |
| 65 | | | | | 70 | | | | | 75 | | | | | 80 |
| Val | Gly | Phe | Arg | Thr | Pro | Gly | Gly | Val | Trp | Trp | Glu | Phe | Gly | Lys | Asp |
| | | | | 85 | | | | | 90 | | | | | 95 | |
| Gly | Asp | Thr | His | Leu | Leu | Gly | Asp | Asn | Pro | Arg | Trp | Leu | Gly | Phe | Gly |
| | | | 100 | | | | | 105 | | | | | 110 | | |
| Gly | Arg | Tyr | Gln | Asp | Leu | Ile | Gly | Asn | Lys | Gly | Leu | Glu | Thr | Val | Thr |
| | | | 115 | | | | 120 | | | | | 125 | | | |
| Met | Gly | Arg | Ala | Glu | Met | Thr | Arg | Ala | Val | Asn | Asp | Leu | Ala | Lys | Lys |
| | 130 | | | | | 135 | | | | | 140 | | | | |
| Lys | Lys | Ala | Ala | Asp | Pro | Gln | Ala | Asp | Thr | Lys | Ser | Lys | Leu | Val | Lys |
| 145 | | | | | 150 | | | | | 155 | | | | | 160 |
| Leu | Val | Val | Met | Val | Cys | Glu | Gly | Leu | Arg | Phe | Asn | Thr | Val | Ser | Arg |
| | | | | 165 | | | | | 170 | | | | | 175 | |
| Thr | Val | Asp | Ala | Gly | Phe | Asn | Ser | Gln | His | Gly | Val | Thr | Leu | Thr | Val |
| | | | 180 | | | | | 185 | | | | | 190 | | |
| Thr | Gln | Gly | Lys | Gln | Val | Gln | Lys | Trp | Asp | Arg | Ile | Ser | Lys | Ala | Ala |
| | | 195 | | | | | 200 | | | | | 205 | | | |
| Phe | Glu | Trp | Ala | Asp | His | Pro | Thr | Ala | Val | Ile | Pro | Asp | Met | Gln | Lys |
| | 210 | | | | | 215 | | | | | 220 | | | | |
| Leu | Gly | Ile | Lys | Asp | Lys | Asn | Glu | Ala | Ala | Arg | Ile | Val | Ala | Leu | Val |
| 225 | | | | | 230 | | | | | 235 | | | | | 240 |
| Lys | Asn | Gln | Thr | Thr | Ala | Ala | Ala | Ala | Thr | Ala | Gly | Ser | Val | Asn | Val |
| | | | | 245 | | | | | 250 | | | | | 255 | |
| Asp | Lys | Pro | Glu | Val | Ile | Asp | Ala | Ser | Glu | Leu | Thr | Pro | Ala | Val | Thr |
| | | | 260 | | | | | 265 | | | | | 270 | | |
| Thr | Tyr | Lys | Leu | Val | Ile | Asn | Gly | Lys | Thr | Leu | Lys | Gly | Glu | Thr | Thr |
| | | 275 | | | | | 280 | | | | | 285 | | | |
| Thr | Glu | Ala | Val | Asp | Ala | Ala | Thr | Ala | Glu | Lys | Val | Phe | Lys | Gln | Tyr |
| | 290 | | | | | 295 | | | | | 300 | | | | |
| Ala | Asn | Asp | Asn | Gly | Val | Asp | Gly | Glu | Trp | Thr | Tyr | Asp | Asp | Ala | Thr |
| 305 | | | | | 310 | | | | | 315 | | | | | 320 |
| Lys | Thr | Phe | Thr | Val | Thr | Glu | Lys | Pro | Glu | Val | Ile | Asp | Ala | Ser | Glu |
| | | | | 325 | | | | | 330 | | | | | 335 | |
| Leu | Thr | Pro | Ala | Val | Thr | Arg | Ser | Lys | Pro | Glu | Val | Ile | Asp | Ala | Ser |
| | | | 340 | | | | | 345 | | | | | 350 | | |
| Glu | Leu | Thr | Pro | Ala | Val | Thr | Thr | Tyr | Lys | Leu | Val | Ile | Asn | Gly | Lys |
| | | 355 | | | | | 360 | | | | | 365 | | | |
| Thr | Leu | Lys | Gly | Glu | Thr | Thr | Thr | Glu | Ala | Val | Asp | Ala | Ala | Thr | Ala |
| | 370 | | | | | 375 | | | | | 380 | | | | |
| Glu | Lys | Val | Phe | Lys | Gln | Tyr | Ala | Asn | Asp | Asn | Gly | Val | Asp | Gly | Glu |
| 385 | | | | | 390 | | | | | 395 | | | | | 400 |
| Trp | Thr | Tyr | Asp | Asp | Ala | Thr | Lys | Thr | Phe | Thr | Val | Thr | Glu | Lys | Pro |

|  |  |  | 405 |  |  |  |  | 410 |  |  |  |  | 415 |  |  |
|--|--|--|--|--|--|--|--|--|--|--|--|--|--|--|--|
| Glu | Val | Ile | Asp | Ala | Ser | Glu | Leu | Thr | Pro | Ala | Val | Thr | Arg | Ser | Ala |
|  |  |  | 420 |  |  |  |  | 425 |  |  |  |  | 430 |  |  |
| Asp | Asn | Asn | Phe | Asn | Lys | Glu | Gln | Gln | Asn | Ala | Phe | Tyr | Glu | Ile | Leu |
|  |  | 435 |  |  |  |  | 440 |  |  |  |  | 445 |  |  |  |
| Asn | Met | Pro | Asn | Leu | Asn | Glu | Glu | Gln | Arg | Asn | Gly | Phe | Ile | Gln | Ser |
|  | 450 |  |  |  |  | 455 |  |  |  |  | 460 |  |  |  |  |
| Leu | Lys | Asp | Asp | Pro | Ser | Gln | Ser | Ala | Asn | Leu | Leu | Ser | Glu | Ala | Lys |
| 465 |  |  |  |  | 470 |  |  |  |  | 475 |  |  |  |  | 480 |
| Lys | Leu | Asn | Glu | Ser | Gln | Ala | Pro | Lys | Asp | Arg | Ser | Ala |  |  |  |
|  |  |  |  | 485 |  |  |  |  | 490 |  |  |  |  |  |  |

(2) INFORMATION FOR SEQ ID NO:24:

(i) SEQUENCE CHARACTERISTICS:
(A) LENGTH: 1722 base pairs
(B) TYPE: nucleic acid
(C) STRANDEDNESS: single
(D) TOPOLOGY: linear (ix) FEATURE:
(A) NAME/KEY: CDS
(B) LOCATION: 51..1559

(xi) SEQUENCE DESCRIPTION: SEQ ID NO:24:

```
TCCCTCTAGA TGCGGCCTAA TTAATTAAGC TTAAAAGGAG GAAAAAAATT ATG AAA      56
                                                         Met Lys
                                                           1
```

| AGA | ATA | GTG | CCA | AAG | TTC | ACT | GAA | ATC | TTC | CCC | GTG | GAG | GAC | GCG | AAC | 104 |
|--|--|--|--|--|--|--|--|--|--|--|--|--|--|--|--|--|
| Arg | Ile | Val | Pro | Lys | Phe | Thr | Glu | Ile | Phe | Pro | Val | Glu | Asp | Ala | Asn |  |
|  |  | 5 |  |  |  |  | 10 |  |  |  |  | 15 |  |  |  |  |

| TAC | CCT | TAC | AGC | GCC | TTC | ATC | GCG | TCG | GTC | CGG | AAA | GAC | GTG | ATC | AAA | 152 |
|--|--|--|--|--|--|--|--|--|--|--|--|--|--|--|--|--|
| Tyr | Pro | Tyr | Ser | Ala | Phe | Ile | Ala | Ser | Val | Arg | Lys | Asp | Val | Ile | Lys |  |
|  | 20 |  |  |  |  | 25 |  |  |  |  | 30 |  |  |  |  |  |

| CAC | TGC | ACC | GAC | CAT | AAA | GGG | ATC | TTC | CAG | CCC | GTG | CTG | CCA | CCG | GAG | 200 |
|--|--|--|--|--|--|--|--|--|--|--|--|--|--|--|--|--|
| His | Cys | Thr | Asp | His | Lys | Gly | Ile | Phe | Gln | Pro | Val | Leu | Pro | Pro | Glu |  |
| 35 |  |  |  |  | 40 |  |  |  |  | 45 |  |  |  |  | 50 |  |

| AAG | AAG | GTC | CCG | GAG | CTA | TGG | TTC | TAC | ACA | GAG | CTC | AAA | ACT | AGG | ACC | 248 |
|--|--|--|--|--|--|--|--|--|--|--|--|--|--|--|--|--|
| Lys | Lys | Val | Pro | Glu | Leu | Trp | Phe | Tyr | Thr | Glu | Leu | Lys | Thr | Arg | Thr |  |
|  |  |  |  | 55 |  |  |  |  | 60 |  |  |  |  | 65 |  |  |

| AGC | TCC | ATC | ACG | CTC | GCC | ATA | CGC | ATG | GAC | AAC | CTG | TAC | CTC | GTG | GGC | 296 |
|--|--|--|--|--|--|--|--|--|--|--|--|--|--|--|--|--|
| Ser | Ser | Ile | Thr | Leu | Ala | Ile | Arg | Met | Asp | Asn | Leu | Tyr | Leu | Val | Gly |  |
|  |  |  | 70 |  |  |  |  | 75 |  |  |  |  | 80 |  |  |  |

| TTC | AGG | ACC | CCG | GGC | GGG | GTG | TGG | TGG | GAG | TTC | GGC | AAG | GAC | GGC | GAC | 344 |
|--|--|--|--|--|--|--|--|--|--|--|--|--|--|--|--|--|
| Phe | Arg | Thr | Pro | Gly | Gly | Val | Trp | Trp | Glu | Phe | Gly | Lys | Asp | Gly | Asp |  |
|  |  | 85 |  |  |  |  | 90 |  |  |  |  | 95 |  |  |  |  |

| ACC | CAC | CTC | CTC | GGC | GAC | AAC | CCC | AGG | TGG | CTC | GGC | TTC | GGC | GGC | AGG | 392 |
|--|--|--|--|--|--|--|--|--|--|--|--|--|--|--|--|--|
| Thr | His | Leu | Leu | Gly | Asp | Asn | Pro | Arg | Trp | Leu | Gly | Phe | Gly | Gly | Arg |  |
| 100 |  |  |  |  | 105 |  |  |  |  | 110 |  |  |  |  |  |  |

| TAC | CAG | GAC | CTC | ATC | GGC | AAC | AAG | GGT | CTG | GAG | ACC | GTC | ACC | ATG | GGC | 440 |
|--|--|--|--|--|--|--|--|--|--|--|--|--|--|--|--|--|
| Tyr | Gln | Asp | Leu | Ile | Gly | Asn | Lys | Gly | Leu | Glu | Thr | Val | Thr | Met | Gly |  |
| 115 |  |  |  | 120 |  |  |  |  | 125 |  |  |  |  | 130 |  |  |

| CGC | GCC | GAA | ATG | ACC | AGG | GCC | GTC | AAC | GAC | CTG | GCG | AAG | AAG | AAG | AAG | 488 |
|--|--|--|--|--|--|--|--|--|--|--|--|--|--|--|--|--|
| Arg | Ala | Glu | Met | Thr | Arg | Ala | Val | Asn | Asp | Leu | Ala | Lys | Lys | Lys | Lys |  |
|  |  |  | 135 |  |  |  |  | 140 |  |  |  |  | 145 |  |  |  |

| GCG | GCT | GAC | CCA | CAG | GCC | GAC | ACG | AAG | AGC | AAG | CTG | GTG | AAG | CTG | GTG | 536 |
|--|--|--|--|--|--|--|--|--|--|--|--|--|--|--|--|--|
| Ala | Ala | Asp | Pro | Gln | Ala | Asp | Thr | Lys | Ser | Lys | Leu | Val | Lys | Leu | Val |  |
|  |  | 150 |  |  |  |  | 155 |  |  |  |  | 160 |  |  |  |  |

| GTC | ATG | GTG | TGC | GAG | GGG | CTG | CGG | TTC | AAC | ACC | GTG | TCC | CGC | ACG | GTG | 584 |
|--|--|--|--|--|--|--|--|--|--|--|--|--|--|--|--|--|
| Val | Met | Val | Cys | Glu | Gly | Leu | Arg | Phe | Asn | Thr | Val | Ser | Arg | Thr | Val |  |
|  | 165 |  |  |  |  | 170 |  |  |  |  | 175 |  |  |  |  |  |

| | | | | | | | | | | | | | | | | |
|---|---|---|---|---|---|---|---|---|---|---|---|---|---|---|---|---|
| GAC | GCG | GGG | TTC | AAC | AGC | CAG | CAC | GGG | GTG | ACC | TTG | ACC | GTG | ACG | CAG | 632 |
| Asp | Ala | Gly | Phe | Asn | Ser | Gln | His | Gly | Val | Thr | Leu | Thr | Val | Thr | Gln | |
| | 180 | | | | 185 | | | | | 190 | | | | | | |
| GGG | AAG | CAG | GTG | CAG | AAG | TGG | GAC | AGG | ATC | TCC | AAG | GCG | GCC | TTC | GAG | 680 |
| Gly | Lys | Gln | Val | Gln | Lys | Trp | Asp | Arg | Ile | Ser | Lys | Ala | Ala | Phe | Glu | |
| 195 | | | | | 200 | | | | | 205 | | | | | 210 | |
| TGG | GCT | GAC | CAC | CCC | ACC | GCT | GTG | ATC | CCC | GAC | ATG | CAG | AAG | CTT | GGC | 728 |
| Trp | Ala | Asp | His | Pro | Thr | Ala | Val | Ile | Pro | Asp | Met | Gln | Lys | Leu | Gly | |
| | | | | 215 | | | | | 220 | | | | | 225 | | |
| ATC | AAG | GAT | AAG | AAC | GAA | GCA | GCG | AGG | ATC | GTT | GCG | CTC | GTT | AAG | AAT | 776 |
| Ile | Lys | Asp | Lys | Asn | Glu | Ala | Ala | Arg | Ile | Val | Ala | Leu | Val | Lys | Asn | |
| | | | 230 | | | | | 235 | | | | | 240 | | | |
| CAA | ACT | ACT | GCC | GCT | GCC | GCT | ACT | GCT | GGA | TCC | TCT | TGC | GCT | CGT | GTC | 824 |
| Gln | Thr | Thr | Ala | Ala | Ala | Ala | Thr | Ala | Gly | Ser | Ser | Cys | Ala | Arg | Val | |
| | | 245 | | | | | 250 | | | | | 255 | | | | |
| CGT | CGT | TCG | AGC | TGC | GGT | GTC | GAC | AAA | CCA | GAA | GTG | ATC | GAT | GCG | TCT | 872 |
| Arg | Arg | Ser | Ser | Cys | Gly | Val | Asp | Lys | Pro | Glu | Val | Ile | Asp | Ala | Ser | |
| | 260 | | | | | 265 | | | | | 270 | | | | | |
| GAA | TTA | ACA | CCA | GCC | GTG | ACA | ACT | TAC | AAA | CTT | GTT | ATT | AAT | GGT | AAA | 920 |
| Glu | Leu | Thr | Pro | Ala | Val | Thr | Thr | Tyr | Lys | Leu | Val | Ile | Asn | Gly | Lys | |
| 275 | | | | | 280 | | | | | 285 | | | | | 290 | |
| ACA | TTG | AAA | GGC | GAA | ACA | ACT | ACT | GAA | GCT | GTT | GAT | GCT | GCT | ACT | GCA | 968 |
| Thr | Leu | Lys | Gly | Glu | Thr | Thr | Thr | Glu | Ala | Val | Asp | Ala | Ala | Thr | Ala | |
| | | | | 295 | | | | | 300 | | | | | 305 | | |
| GAA | AAA | GTC | TTC | AAA | CAA | TAC | GCT | AAC | GAC | AAC | GGT | GTT | GAC | GGT | GAA | 1016 |
| Glu | Lys | Val | Phe | Lys | Gln | Tyr | Ala | Asn | Asp | Asn | Gly | Val | Asp | Gly | Glu | |
| | | | 310 | | | | | 315 | | | | | 320 | | | |
| TGG | ACT | TAC | GAC | GAT | GCG | ACT | AAG | ACC | TTT | ACA | GTT | ACT | GAA | AAA | CCA | 1064 |
| Trp | Thr | Tyr | Asp | Asp | Ala | Thr | Lys | Thr | Phe | Thr | Val | Thr | Glu | Lys | Pro | |
| | | 325 | | | | | 330 | | | | | 335 | | | | |
| GAA | GTG | ATC | GAT | GCG | TCT | GAA | TTA | ACA | CCA | GCC | GTG | ACA | AGA | TCC | AAA | 1112 |
| Glu | Val | Ile | Asp | Ala | Ser | Glu | Leu | Thr | Pro | Ala | Val | Thr | Arg | Ser | Lys | |
| | 340 | | | | | 345 | | | | | 350 | | | | | |
| CCA | GAA | GTG | ATC | GAT | GCG | TCT | GAA | TTA | ACA | CCA | GCC | GTG | ACA | ACT | TAC | 1160 |
| Pro | Glu | Val | Ile | Asp | Ala | Ser | Glu | Leu | Thr | Pro | Ala | Val | Thr | Thr | Tyr | |
| 355 | | | | | 360 | | | | | 365 | | | | | 370 | |
| AAA | CTT | GTT | ATT | AAT | GGT | AAA | ACA | TTG | AAA | GGC | GAA | ACA | ACT | ACT | GAA | 1208 |
| Lys | Leu | Val | Ile | Asn | Gly | Lys | Thr | Leu | Lys | Gly | Glu | Thr | Thr | Thr | Glu | |
| | | | | 375 | | | | | 380 | | | | | 385 | | |
| GCT | GTT | GAT | GCT | GCT | ACT | GCA | GAA | AAA | GTC | TTC | AAA | CAA | TAC | GCT | AAC | 1256 |
| Ala | Val | Asp | Ala | Ala | Thr | Ala | Glu | Lys | Val | Phe | Lys | Gln | Tyr | Ala | Asn | |
| | | | 390 | | | | | 395 | | | | | 400 | | | |
| GAC | AAC | GGT | GTT | GAC | GGT | GAA | TGG | ACT | TAC | GAC | GAT | GCG | ACT | AAG | ACC | 1304 |
| Asp | Asn | Gly | Val | Asp | Gly | Glu | Trp | Thr | Tyr | Asp | Asp | Ala | Thr | Lys | Thr | |
| | | 405 | | | | | 410 | | | | | 415 | | | | |
| TTT | ACA | GTT | ACT | GAA | AAA | CCA | GAA | GTG | ATC | GAT | GCG | TCT | GAA | TTA | ACA | 1352 |
| Phe | Thr | Val | Thr | Glu | Lys | Pro | Glu | Val | Ile | Asp | Ala | Ser | Glu | Leu | Thr | |
| | 420 | | | | | 425 | | | | | 430 | | | | | |
| CCA | GCC | GTG | ACA | AGA | TCC | GCT | GAT | AAC | AAT | TTC | AAC | AAA | GAA | CAA | CAA | 1400 |
| Pro | Ala | Val | Thr | Arg | Ser | Ala | Asp | Asn | Asn | Phe | Asn | Lys | Glu | Gln | Gln | |
| 435 | | | | | 440 | | | | | 445 | | | | | 450 | |
| AAT | GCT | TTC | TAT | GAA | ATC | TTG | AAT | ATG | CCT | AAC | TTA | AAC | GAA | GAA | CAA | 1448 |
| Asn | Ala | Phe | Tyr | Glu | Ile | Leu | Asn | Met | Pro | Asn | Leu | Asn | Glu | Glu | Gln | |
| | | | | 455 | | | | | 460 | | | | | 465 | | |
| CGC | AAT | GGT | TTC | ATC | CAA | AGC | TTA | AAA | GAT | GAC | CCA | AGC | CAA | AGT | GCT | 1496 |
| Arg | Asn | Gly | Phe | Ile | Gln | Ser | Leu | Lys | Asp | Asp | Pro | Ser | Gln | Ser | Ala | |
| | | | 470 | | | | | 475 | | | | | 480 | | | |
| AAC | CTA | TTG | TCA | GAA | GCT | AAA | AAG | TTA | AAT | GAA | TCT | CAA | GCA | CCG | AAA | 1544 |
| Asn | Leu | Leu | Ser | Glu | Ala | Lys | Lys | Leu | Asn | Glu | Ser | Gln | Ala | Pro | Lys | |
| | | 485 | | | | | 490 | | | | | 495 | | | | |

-continued

```
GAT CGA TCC GCC TGATCAATGC AACGACACAT CATGATCTGC TGCTGCACTT      1596
Asp Arg Ser Ala
    500

AATTACTATG TTCGTATACA AATAAATACA CCCGGCGTAC GCGGTGTTCC TTATATGGTC  1656

TAAAATGTAG CCAGTAAATT TTAAACTACT TTCTCGTGCC GAATTCACTG GCCGGCATGC  1716

TATATA                                                              1722
```

( 2 ) INFORMATION FOR SEQ ID NO:25:

( i ) SEQUENCE CHARACTERISTICS:
        ( A ) LENGTH: 502 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Met Lys Arg Ile Val Pro Lys Phe Thr Glu Ile Phe Pro Val Glu Asp
 1               5                  10                  15

Ala Asn Tyr Pro Tyr Ser Ala Phe Ile Ala Ser Val Arg Lys Asp Val
                20                  25                  30

Ile Lys His Cys Thr Asp His Lys Gly Ile Phe Gln Pro Val Leu Pro
            35                  40                  45

Pro Glu Lys Lys Val Pro Glu Leu Trp Phe Tyr Thr Glu Leu Lys Thr
        50                  55                  60

Arg Thr Ser Ser Ile Thr Leu Ala Ile Arg Met Asp Asn Leu Tyr Leu
 65                  70                  75                  80

Val Gly Phe Arg Thr Pro Gly Gly Val Trp Trp Glu Phe Gly Lys Asp
                85                  90                  95

Gly Asp Thr His Leu Leu Gly Asp Asn Pro Arg Trp Leu Gly Phe Gly
            100                 105                 110

Gly Arg Tyr Gln Asp Leu Ile Gly Asn Lys Gly Leu Glu Thr Val Thr
        115                 120                 125

Met Gly Arg Ala Glu Met Thr Arg Ala Val Asn Asp Leu Ala Lys Lys
    130                 135                 140

Lys Lys Ala Ala Asp Pro Gln Ala Asp Thr Lys Ser Lys Leu Val Lys
145                 150                 155                 160

Leu Val Val Met Val Cys Glu Gly Leu Arg Phe Asn Thr Val Ser Arg
                165                 170                 175

Thr Val Asp Ala Gly Phe Asn Ser Gln His Gly Val Thr Leu Thr Val
            180                 185                 190

Thr Gln Gly Lys Gln Val Gln Lys Trp Asp Arg Ile Ser Lys Ala Ala
        195                 200                 205

Phe Glu Trp Ala Asp His Pro Thr Ala Val Ile Pro Asp Met Gln Lys
    210                 215                 220

Leu Gly Ile Lys Asp Lys Asn Glu Ala Ala Arg Ile Val Ala Leu Val
225                 230                 235                 240

Lys Asn Gln Thr Thr Ala Ala Ala Thr Ala Gly Ser Ser Cys Ala
                245                 250                 255

Arg Val Arg Arg Ser Ser Cys Gly Val Asp Lys Pro Glu Val Ile Asp
            260                 265                 270

Ala Ser Glu Leu Thr Pro Ala Val Thr Thr Tyr Lys Leu Val Ile Asn
        275                 280                 285

Gly Lys Thr Leu Lys Gly Glu Thr Thr Thr Glu Ala Val Asp Ala Ala
    290                 295                 300

Thr Ala Glu Lys Val Phe Lys Gln Tyr Ala Asn Asp Asn Gly Val Asp
```

```
305                    310                    315                    320
Gly Glu Trp Thr Tyr Asp Asp Ala Thr Lys Thr Phe Thr Val Thr Glu
                325                    330                    335

Lys Pro Glu Val Ile Asp Ala Ser Glu Leu Thr Pro Ala Val Thr Arg
            340                    345                    350

Ser Lys Pro Glu Val Ile Asp Ala Ser Glu Leu Thr Pro Ala Val Thr
            355                    360                    365

Thr Tyr Lys Leu Val Ile Asn Gly Lys Thr Leu Lys Gly Glu Thr Thr
        370                    375                    380

Thr Glu Ala Val Asp Ala Ala Thr Ala Glu Lys Val Phe Lys Gln Tyr
385                    390                    395                    400

Ala Asn Asp Asn Gly Val Asp Gly Glu Trp Thr Tyr Asp Asp Ala Thr
                405                    410                    415

Lys Thr Phe Thr Val Thr Glu Lys Pro Glu Val Ile Asp Ala Ser Glu
            420                    425                    430

Leu Thr Pro Ala Val Thr Arg Ser Ala Asp Asn Asn Phe Asn Lys Glu
            435                    440                    445

Gln Gln Asn Ala Phe Tyr Glu Ile Leu Asn Met Pro Asn Leu Asn Glu
    450                    455                    460

Glu Gln Arg Asn Gly Phe Ile Gln Ser Leu Lys Asp Asp Pro Ser Gln
465                    470                    475                    480

Ser Ala Asn Leu Leu Ser Glu Ala Lys Lys Leu Asn Glu Ser Gln Ala
                485                    490                    495

Pro Lys Asp Arg Ser Ala
            500
```

( 2 ) INFORMATION FOR SEQ ID NO:26:

( i ) SEQUENCE CHARACTERISTICS:
        ( A ) LENGTH: 280 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:26:

```
Ala Ala Lys Met Ala Lys Asn Val Asp Lys Pro Leu Phe Thr Ala Thr
1               5                   10                      15

Phe Asn Val Gln Ala Ser Ser Ala Asp Tyr Ala Thr Phe Ile Ala Gly
            20                      25                      30

Ile Arg Asn Lys Leu Arg Asn Pro Ala His Phe Ser His Asn Glu Pro
        35                      40                      45

Val Leu Pro Pro Val Glu Pro Asn Val Pro Pro Ser Arg Trp Phe His
    50                      55                      60

Val Val Leu Lys Ala Ser Pro Thr Ser Ala Gly Leu Thr Leu Ala Ile
65                      70                      75                  80

Arg Ala Asp Asn Ile Tyr Leu Glu Gly Phe Lys Ser Ser Asp Gly Thr
                85                      90                      95

Trp Trp Glu Leu Thr Pro Gly Leu Ile Pro Gly Ala Thr Tyr Val Gly
            100                     105                     110

Phe Gly Gly Thr Tyr Arg Asp Leu Leu Gly Asp Thr Asp Lys Leu Thr
            115                     120                     125

Asn Val Ala Leu Gly Arg Gln Gln Leu Glu Asp Ala Val Thr Ala Leu
        130                     135                     140

His Gly Arg Thr Lys Ala Asp Lys Ala Ser Gly Pro Lys Gln Gln Gln
145                     150                     155                 160
```

```
Ala Arg Glu Ala Val Thr Thr Leu Leu Leu Met Val Asn Glu Ala Thr
                165             170                 175

Arg Phe Gln Thr Val Ser Gly Phe Val Ala Gly Leu Leu His Pro Lys
            180             185                 190

Ala Val Glu Lys Lys Ser Gly Lys Ile Gly Asn Glu Met Lys Ala Gln
            195             200                 205

Val Asn Gly Trp Gln Asp Leu Ser Ala Ala Leu Leu Lys Thr Asp Val
    210             215                 220

Lys Pro Pro Pro Gly Lys Ser Pro Ala Lys Phe Thr Pro Ile Glu Lys
225             230                 235                     240

Met Gly Val Arg Thr Ala Glu Gln Ala Ala Ala Thr Leu Gly Ile Leu
            245             250                 255

Leu Phe Val Glu Val Pro Gly Gly Leu Thr Val Ala Lys Ala Leu Glu
            260             265                 270

Leu Phe His Ala Ser Gly Gly Lys
            275             280
```

( 2 ) INFORMATION FOR SEQ ID NO:27:

( i ) SEQUENCE CHARACTERISTICS:
  ( A ) LENGTH: 290 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:27:

```
Met Tyr Ala Val Ala Thr Trp Leu Cys Phe Gly Ser Thr Ser Gly Trp
1               5                   10                  15

Ser Phe Thr Leu Glu Asp Asn Asn Ile Phe Pro Lys Gln Tyr Pro Ile
            20                  25                  30

Ile Asn Phe Thr Thr Ala Gly Ala Thr Val Gln Ser Tyr Thr Asn Phe
            35                  40                  45

Ile Arg Ala Val Arg Gly Arg Leu Thr Thr Gly Ala Asp Val Arg His
    50                  55                  60

Glu Ile Pro Val Leu Pro Asn Arg Val Gly Leu Pro Ile Asn Gln Arg
65                      70                  75                  80

Phe Ile Leu Val Glu Leu Ser Asn His Ala Glu Leu Ser Val Thr Leu
                85                  90                  95

Ala Leu Asp Val Thr Asn Ala Tyr Val Val Gly Tyr Arg Ala Gly Asn
            100                 105                 110

Ser Ala Tyr Phe Phe His Pro Asp Asn Gln Glu Asp Ala Glu Ala Ile
            115                 120                 125

Thr His Leu Phe Thr Asp Val Gln Asn Arg Tyr Thr Phe Ala Phe Gly
    130                 135                 140

Gly Asn Tyr Asp Arg Leu Glu Gln Leu Ala Gly Asn Leu Arg Glu Asn
145                 150                 155                 160

Ile Glu Leu Gly Asn Gly Pro Leu Glu Glu Ala Ile Ser Ala Leu Tyr
            165                 170                 175

Tyr Tyr Ser Thr Gly Gly Thr Gln Leu Pro Thr Leu Ala Arg Ser Phe
            180                 185                 190

Ile Ile Cys Ile Gln Met Ile Ser Glu Ala Ala Arg Phe Gln Tyr Ile
            195                 200                 205

Glu Gly Glu Met Arg Thr Arg Ile Arg Tyr Asn Arg Arg Ser Ala Pro
    210                 215                 220
```

```
Asp  Pro  Ser  Val  Ile  Thr  Leu  Glu  Asn  Ser  Trp  Gly  Arg  Leu  Ser  Thr
225                 230                 235                               240

Ala  Ile  Gln  Glu  Ser  Asn  Gln  Gly  Ala  Phe  Ala  Ser  Pro  Ile  Gln  Leu
               245                      250                      255

Gln  Arg  Arg  Asn  Gly  Ser  Lys  Phe  Ser  Val  Tyr  Asp  Val  Ser  Ile  Leu
               260                 265                      270

Ile  Pro  Ile  Ile  Ala  Leu  Met  Val  Tyr  Arg  Cys  Ala  Pro  Pro  Pro  Ser
          275                      280                 285

Gln  Phe
     290
```

( 2 ) INFORMATION FOR SEQ ID NO:28:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:28:

```
Val  Asn  Thr  Ile  Ile  Tyr  Asn  Val  Gly  Ser  Thr  Thr  Ile  Ser  Asn  Tyr
1              5                        10                           15

Ala  Thr  Phe  Met  Asp  Asn  Leu  Arg  Asn  Glu  Ala  Lys  Asp
               20                       25
```

( 2 ) INFORMATION FOR SEQ ID NO:29:

( i ) SEQUENCE CHARACTERISTICS:
    ( A ) LENGTH: 27 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:29:

```
Asn  Ile  Val  Phe  Asp  Tyr  Glu  Asn  Ala  Thr  Pro  Glu  Thr  Tyr  Ser  Asn
1              5                        10                           15

Phe  Leu  Thr  Ser  Leu  Arg  Glu  Ala  Val  Lys  Asp
               20                       25
```

( 2 ) INFORMATION FOR SEQ ID NO:30:

( i ) SEQUENCE CHARACTERISTICS:
    ( A ) LENGTH: 25 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:30:

```
Lys  Glu  Phe  Thr  Leu  Asp  Phe  Ser  Thr  Ala  Lys  Thr  Tyr  Asp  Ser  Leu
1              5                        10                           15

Asn  Val  Ile  Arg  Ser  Ala  Ile  Gly  Thr
               20                  25
```

( 2 ) INFORMATION FOR SEQ ID NO:31:

( i ) SEQUENCE CHARACTERISTICS:
    ( A ) LENGTH: 27 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:31:

Asp Val Ser Phe Arg Leu Ser Gly Ala Thr Ser Ser Ser Tyr Gly Val
1               5                   10                  15

Phe Ile Ser Asn Leu Arg Lys Ala Leu Pro Asn
                20                  25

( 2 ) INFORMATION FOR SEQ ID NO:32:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:32:

Asp Val Ser Phe Arg Leu Ser Gly Ala Asp Pro Arg Ser Tyr Gly Met
1               5                   10                  15

Phe Ile Lys Asp Leu Arg Asn Ala Leu Pro Phe
                20                  25

( 2 ) INFORMATION FOR SEQ ID NO:33:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:33:

Asp Val Ser Phe Arg Leu Ser Gly Ala Thr Thr Thr Ser Tyr Gly Val
1               5                   10                  15

Phe Ile Lys Asn Leu Arg Glu Ala Leu Pro Tyr
                20                  25

( 2 ) INFORMATION FOR SEQ ID NO:34:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:34:

Gly Leu Asp Thr Val Ser Phe Ser Thr Lys Gly Ala Thr Tyr Ile Thr
1               5                   10                  15

Tyr Val Asn Phe Leu Asn Glu Leu Arg Val Lys Leu Lys Pro
                20                  25                  30

( 2 ) INFORMATION FOR SEQ ID NO:35:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:35:

```
        Val Thr Ser Ile Thr Leu Asp Leu Val Asn Pro Thr Ala Gly Gln Tyr
        1               5                   10                  15

Ser Ser Phe Val Asp Lys Ile Arg Asn Asn Val Lys Asp
                    20                  25
```

( 2 ) INFORMATION FOR SEQ ID NO:36:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:36:

```
        Val Ile Ile Tyr Glu Leu Asn Leu Gln Gly Thr Thr Lys Ala Gln Tyr
        1               5                   10                  15

Ser Thr Ile Leu Lys Gln Leu Arg Asp Asp Ile Lys Asp
                    20                  25
```

( 2 ) INFORMATION FOR SEQ ID NO:37:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:37:

```
        Val Ser Leu Gly Leu Lys Arg Asp Asn Leu Tyr Val Val Ala Tyr
        1               5                   10                  15
```

( 2 ) INFORMATION FOR SEQ ID NO:38:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:38:

```
        Ala Ile Gln Met Thr Ala Glu Ala Ala Arg Phe Arg Tyr Ile Gln
        1               5                   10                  15
```

( 2 ) INFORMATION FOR SEQ ID NO:39:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

```
ACCGTCACCA TGGGCCGCGC CGAAATGACC AGGGCCGTCA ACGACCTGGC GAAGAAGAAG      60

AAGGCGGCTG ACCCACAGGC CGACACGAAG AGC                                  93
```

( 2 ) INFORMATION FOR SEQ ID NO:40:

( i ) SEQUENCE CHARACTERISTICS:
        ( A ) LENGTH: 30 base pairs
        ( B ) TYPE: nucleic acid
        ( C ) STRANDEDNESS: single ( D ) TOPOLOGY: linear ( x i ) SEQUENCE DESCRIPTION: SEQ ID NO:40:

CGGATCCAGC AGTAGCGGCA GCGGCAGTAG 30

( 2 ) INFORMATION FOR SEQ ID NO:41:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

ACCGTCACCA TGGGCCGCGC CGAAATGACC AGGGCCGTCA ACGACCTGGC GAAGAAGAAG 60

AAGGCGGCCG CCGCTGCAGA CCCACAGGCC GACACGAAG 99

( 2 ) INFORMATION FOR SEQ ID NO:42:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

CATGCCGGCC AGTGAATTCG G 21

( 2 ) INFORMATION FOR SEQ ID NO:43:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

GATCCGTTAA CGTCGACG 18

( 2 ) INFORMATION FOR SEQ ID NO:44:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

ATATTAGTCG ACAAACCAGA AGTGATCGAT GCG 33

( 2 ) INFORMATION FOR SEQ ID NO:45:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

GCAATTGCAG CTGCTTAA 18

( 2 ) INFORMATION FOR SEQ ID NO:46:

( i ) SEQUENCE CHARACTERISTICS:
        ( A ) LENGTH: 10 amino acids
        ( B ) TYPE: amino acid
        ( C ) STRANDEDNESS: single ( D ) TOPOLOGY: linear ( i i ) MOLECULE TYPE: protein ( x i ) SEQUENCE DESCRIPTION: SEQ ID NO:46:

Glu  Val  Asn  Trp  Lys  Lys  Ile  Ser  Thr  Ala
1                  5                        10

( 2 ) INFORMATION FOR SEQ ID NO:47:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:47:

Ile  Glu  Val  Gly  Ile  Asp  Val  Thr  Asn  Ala  Tyr  Val  Val  Ala  Tyr
1                  5                        10                       15

( 2 ) INFORMATION FOR SEQ ID NO:48:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:48:

Ile  Ile  Gln  Val  Ala  Ser  Glu  Ala  Ala  Arg  Phe  Arg  Tyr  Ile  Ser
1                  5                        10                       15

( 2 ) INFORMATION FOR SEQ ID NO:49:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:49:

Leu  Glu  Asn  Asn  Trp  Asp  Asn  Leu  Arg  Gly  Val
1                  5                        10

( 2 ) INFORMATION FOR SEQ ID NO:50:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:50:

Met  Ile  Asp  Ser  Gly  Ser  Gly  Asp  Asn  Leu  Phe  Ala  Val  Asp  Val
1                  5                        10                       15

( 2 ) INFORMATION FOR SEQ ID NO:51:

( i ) SEQUENCE CHARACTERISTICS:
        ( A ) LENGTH: 15 amino acids
        ( B ) TYPE: amino acid
        ( C ) STRANDEDNESS: single ( D ) TOPOLOGY: linear ( i i ) MOLECULE TYPE: protein ( x i ) SEQUENCE DESCRIPTION: SEQ ID NO:51:

Phe Val Thr Val Thr Ala Glu Ala Leu Arg Phe Gln Ile Gln Arg
1               5                   10                  15

( 2 ) INFORMATION FOR SEQ ID NO:52:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:52:

Thr Leu Asn Trp Gly Arg Leu Ser Ser Val
1               5                   10

( 2 ) INFORMATION FOR SEQ ID NO:53:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:53:

Asp Glu Val Ala Leu Asp Val Thr Asn Val
1               5                   10

( 2 ) INFORMATION FOR SEQ ID NO:54:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:54:

Tyr Leu Met Gly Tyr
1               5

( 2 ) INFORMATION FOR SEQ ID NO:55:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:55:

Leu Ile Gln Ser Thr Ser Glu Ala Ala Arg Tyr Lys Phe Ile Glu
1               5                   10                  15

( 2 ) INFORMATION FOR SEQ ID NO:56:

( i ) SEQUENCE CHARACTERISTICS:
        ( A ) LENGTH: 12 amino acids
        ( B ) TYPE: amino acid
        ( C ) STRANDEDNESS: single (D) TOPOLOGY: linear (ii) MOLECULE TYPE: protein (xi) SEQUENCE DESCRIPTION: SEQ ID NO:56:

```
Leu Glu Asn Ser Leu Trp Leu Ala Leu Ser Lys Gln
1               5                   10
```

(2) INFORMATION FOR SEQ ID NO:57:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:57:

GATCCTCTTG CGCTCGTGTC CGTCGTTCGA GCTGCGGTG        39

(2) INFORMATION FOR SEQ ID NO:58:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:58:

GAGAACGCGA GCACAGGCAG CAAGCTCGAC GCCACAGCTG        40

(2) INFORMATION FOR SEQ ID NO:59:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

```
Gly Ser Ser Cys Ala Arg Val Arg Arg Ser Ser Cys Gly Val Asp
1               5                   10                  15
```

(2) INFORMATION FOR SEQ ID NO:60:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:60:

```
Tyr Tyr Ser Thr Cys Gly Thr Gln Ile Pro Thr
1               5                   10
```

(2) INFORMATION FOR SEQ ID NO:61:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:61:

```
    Ile  Ser  Phe  Phe  Arg  Ser  Gly  Gly  Asn  Asp  Asn
    1                   5                        10
```

( 2 ) INFORMATION FOR SEQ ID NO:62:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:62:

```
    Ile  Phe  His  Tyr  Asp  Ser  Thr  Ala  Ala  Ala  Ala
    1                   5                        10
```

( 2 ) INFORMATION FOR SEQ ID NO:63:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:63:

```
    Ile  Phe  His  Tyr  Asp  Ser  Thr  Ala  Ala  Ala  Ala
    1                   5                        10
```

( 2 ) INFORMATION FOR SEQ ID NO:64:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:64:

```
    Leu  Leu  His  Tyr  Asp  Ser  Thr  Ala  Ala  Ala  Gly
    1                   5                        10
```

( 2 ) INFORMATION FOR SEQ ID NO:65:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:65:

```
    Thr  Leu  Phe  Tyr  Tyr  Asn  Ala  Asn  Ser  Ala  Ala
    1                   5                        10
```

( 2 ) INFORMATION FOR SEQ ID NO:66:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:66:

```
Ile  Ser  Gly  Gln  Gly  Ser  Phe  Thr  Glu  Lys  Ile
1              5                        10
```

( 2 ) INFORMATION FOR SEQ ID NO:67:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:67:

```
Ile  Tyr  Gly  Lys  Ala  Gly  Asp  Val  Lys  Lys  Gln
1              5                        10
```

( 2 ) INFORMATION FOR SEQ ID NO:68:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:68:

```
Val  Asn  Lys  Lys  Ala  Arg  Val  Val  Lys  Asp  Glu
1              5                        10
```

( 2 ) INFORMATION FOR SEQ ID NO:69:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:69:

```
Thr  Lys  Ala  Asp  Lys  Ala  Ser  Gly  Pro  Lys  Gln
1              5                        10
```

( 2 ) INFORMATION FOR SEQ ID NO:70:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:70:

```
Asp  Gly  Val  Asn  Lys  Lys  Val  Arg  Val  Val  Lys
1              5                        10
```

( 2 ) INFORMATION FOR SEQ ID NO:71:

( i ) SEQUENCE CHARACTERISTICS:
        ( A ) LENGTH: 250 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:71:

| | | | | | | | | | | | | | | | |
|---|---|---|---|---|---|---|---|---|---|---|---|---|---|---|---|
| Glu<br>1 | Asp | Arg | Pro | Ile<br>5 | Lys | Phe | Ser | Thr | Glu<br>10 | Gly | Ala | Thr | Ser | Gln<br>15 | Ser |
| Tyr | Lys | Gln | Phe<br>20 | Ile | Glu | Ala | Leu | Arg<br>25 | Glu | Arg | Leu | Arg | Gly<br>30 | Gly | Leu |
| Ile | His | Asp<br>35 | Ile | Pro | Val | Leu | Pro<br>40 | Asp | Pro | Thr | Thr | Leu<br>45 | Gln | Glu | Arg |
| Asn | Arg<br>50 | Tyr | Ile | Thr | Val | Glu<br>55 | Leu | Ser | Asn | Ser | Asp<br>60 | Thr | Glu | Ser | Ile |
| Glu<br>65 | Val | Gly | Ile | Asp | Val<br>70 | Thr | Asn | Ala | Tyr | Val<br>75 | Val | Ala | Tyr | Arg | Ala<br>80 |
| Gly | Thr | Gln | Ser | Tyr<br>85 | Phe | Leu | Arg | Asp | Ala<br>90 | Pro | Ser | Ser | Ala | Ser<br>95 | Asp |
| Tyr | Leu | Phe | Thr<br>100 | Gly | Thr | Asp | Gln | His<br>105 | Ser | Leu | Pro | Phe | Tyr<br>110 | Gly | Thr |
| Tyr | Gly | Asp<br>115 | Leu | Glu | Arg | Trp<br>120 | Ala | His | Gln | Ser | Arg<br>125 | Gln | Gln | Ile | Pro |
| Leu | Gly<br>130 | Leu | Gln | Ala | Leu | Thr<br>135 | His | Gly | Ile | Ser | Phe<br>140 | Phe | Arg | Ser | Gly |
| Gly<br>145 | Asn | Asp | Asn | Glu | Glu<br>150 | Lys | Ala | Arg | Thr | Leu<br>155 | Ile | Val | Ile | Ile | Gln<br>160 |
| Met | Val | Ala | Glu | Ala<br>165 | Ala | Arg | Phe | Arg | Tyr<br>170 | Ile | Ser | Asn | Arg | Val<br>175 | Arg |
| Val | Ser | Ile | Gln<br>180 | Thr | Gly | Thr | Ala | Phe<br>185 | Gln | Pro | Asp | Ala | Ala<br>190 | Met | Ile |
| Ser | Leu | Glu<br>195 | Asn | Asn | Trp | Asp | Asn<br>200 | Leu | Arg | Gly | Val | Gln<br>205 | Glu | Ser | Val |
| Gln | Asp<br>210 | Thr | Phe | Pro | Asn | Gln<br>215 | Val | Thr | Leu | Thr | Asn<br>220 | Ile | Arg | Asn | Glu |
| Pro<br>225 | Val | Ile | Val | Asp | Ser<br>230 | Leu | Ser | His | Pro | Thr<br>235 | Val | Ala | Val | Leu | Ala<br>240 |
| Leu | Met | Leu | Phe | Val<br>245 | Cys | Asn | Pro | Pro | Asn<br>250 | | | | | | |

(2) INFORMATION FOR SEQ ID NO:72:

(i) SEQUENCE CHARACTERISTICS:
    (A) LENGTH: 260 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:72:

| | | | | | | | | | | | | | | | |
|---|---|---|---|---|---|---|---|---|---|---|---|---|---|---|---|
| Val<br>1 | Thr | Ser | Ile | Thr<br>5 | Leu | Asp | Leu | Val | Asn<br>10 | Pro | Thr | Ala | Gly | Gln<br>15 | Tyr |
| Ser | Ser | Phe | Val<br>20 | Asp | Lys | Ile | Arg | Asn<br>25 | Asn | Val | Lys | Asp | Pro<br>30 | Asn | Leu |
| Lys | Tyr | Gly<br>35 | Gly | Thr | Asp | Ile<br>40 | Ala | Val | Ile | Gly | Pro<br>45 | Pro | Ser | Lys | Glu |
| Lys | Phe<br>50 | Leu | Arg | Ile | Asn | Phe<br>55 | Gln | Ser | Ser | Arg | Gly<br>60 | Thr | Val | Ser | Leu |
| Gly<br>65 | Leu | Lys | Arg | Asp | Asn<br>70 | Leu | Tyr | Val | Val | Ala<br>75 | Tyr | Leu | Ala | Met | Asp<br>80 |
| Asn | Thr | Asn | Val | Asn<br>85 | Arg | Ala | Tyr | Tyr | Phe<br>90 | Arg | Ser | Glu | Ile | Thr<br>95 | Ser |
| Ala | Glu | Ser | Thr | Ala | Leu | Phe | Pro | Glu | Ala | Thr | Thr | Ala | Asn | Gln | Lys |

|     |     |     |     |     | 100 |     |     |     |     | 105 |     |     |     |     | 110 |     |     |
| --- | --- | --- | --- | --- | --- | --- | --- | --- | --- | --- | --- | --- | --- | --- | --- | --- | --- |
| Ala | Leu | Glu | Tyr | Thr | Glu | Asp | Tyr | Gln | Ser | Ile | Glu | Lys | Asn | Ala | Gln |
|     |     |     | 115 |     |     |     | 120 |     |     |     | 125 |     |     |     |     |
| Ile | Thr | Gln | Gly | Asp | Gln | Ser | Arg | Lys | Glu | Leu | Gly | Leu | Gly | Ile | Asp |
|     | 130 |     |     |     | 135 |     |     |     |     | 140 |     |     |     |     |     |
| Leu | Leu | Ser | Thr | Ser | Met | Glu | Ala | Val | Asn | Lys | Lys | Ala | Arg | Val | Val |
| 145 |     |     |     |     | 150 |     |     |     |     | 155 |     |     |     |     | 160 |
| Lys | Asp | Glu | Ala | Arg | Phe | Leu | Leu | Ile | Ala | Ile | Gln | Met | Thr | Ala | Glu |
|     |     |     |     | 165 |     |     |     |     | 170 |     |     |     |     | 175 |     |
| Ala | Ala | Arg | Phe | Arg | Tyr | Ile | Gln | Asn | Leu | Val | Ile | Lys | Asn | Phe | Pro |
|     |     |     | 180 |     |     |     |     | 185 |     |     |     |     | 190 |     |     |
| Asn | Lys | Phe | Asn | Ser | Glu | Asn | Lys | Val | Ile | Gln | Phe | Glu | Val | Asn | Trp |
|     |     | 195 |     |     |     |     | 200 |     |     |     |     | 205 |     |     |     |
| Lys | Lys | Ile | Ser | Thr | Ala | Ile | Tyr | Gly | Asp | Ala | Lys | Asn | Gly | Val | Phe |
|     |     | 210 |     |     |     |     | 215 |     |     |     |     | 220 |     |     |     |
| Asn | Lys | Asp | Tyr | Asp | Phe | Gly | Phe | Gly | Lys | Val | Arg | Gln | Val | Lys | Asp |
| 225 |     |     |     |     | 230 |     |     |     |     | 235 |     |     |     |     | 240 |
| Leu | Gln | Met | Gly | Leu | Leu | Met | Tyr | Leu | Gly | Lys | Pro | Lys | Ser | Ser | Asn |
|     |     |     |     | 245 |     |     |     |     | 250 |     |     |     | 255 |     |     |
| Glu | Ala | Asn | Ser |     |     |     |     |     |     |     |     |     |     |     |     |
|     |     |     | 260 |     |     |     |     |     |     |     |     |     |     |     |     |

( 2 ) INFORMATION FOR SEQ ID NO:73:

( i ) SEQUENCE CHARACTERISTICS:
        ( A ) LENGTH: 315 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:73:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Lys | Ile | Ile | Ile | Phe | Arg | Val | Leu | Thr | Phe | Phe | Phe | Val | Ile | Phe |
| 1   |     |     |     | 5   |     |     |     |     | 10  |     |     |     |     | 15  |     |
| Ser | Val | Asn | Val | Val | Ala | Lys | Glu | Phe | Thr | Leu | Asp | Phe | Ser | Thr | Ala |
|     |     |     | 20  |     |     |     |     | 25  |     |     |     |     | 30  |     |     |
| Lys | Thr | Tyr | Val | Asp | Ser | Leu | Asn | Val | Ile | Arg | Ser | Ala | Ile | Gly | Thr |
|     |     | 35  |     |     |     |     | 40  |     |     |     |     | 45  |     |     |     |
| Pro | Leu | Gln | Thr | Ile | Ser | Ser | Gly | Gly | Thr | Ser | Leu | Leu | Met | Ile | Asp |
|     | 50  |     |     |     |     | 55  |     |     |     |     | 60  |     |     |     |     |
| Ser | Gly | Ser | Gly | Asp | Asn | Leu | Phe | Ala | Val | Asp | Val | Arg | Gly | Ile | Asp |
| 65  |     |     |     |     | 70  |     |     |     |     | 75  |     |     |     |     | 80  |
| Pro | Glu | Glu | Gly | Arg | Phe | Asn | Asn | Leu | Arg | Leu | Ile | Val | Glu | Arg | Asn |
|     |     |     |     | 85  |     |     |     |     | 90  |     |     |     |     | 95  |     |
| Asn | Leu | Tyr | Val | Thr | Gly | Phe | Val | Asn | Arg | Thr | Asn | Asn | Val | Phe | Tyr |
|     |     |     | 100 |     |     |     |     | 105 |     |     |     |     | 110 |     |     |
| Arg | Phe | Ala | Asp | Phe | Ser | His | Val | Thr | Phe | Pro | Gly | Thr | Thr | Ala | Val |
|     |     | 115 |     |     |     |     | 120 |     |     |     |     | 125 |     |     |     |
| Thr | Leu | Ser | Gly | Asp | Ser | Ser | Tyr | Thr | Thr | Leu | Gln | Arg | Val | Ala | Gly |
|     | 130 |     |     |     |     | 135 |     |     |     |     | 140 |     |     |     |     |
| Ile | Ser | Arg | Thr | Gly | Met | Gln | Ile | Asn | Arg | His | Ser | Leu | Thr | Thr | Ser |
| 145 |     |     |     |     | 150 |     |     |     |     | 155 |     |     |     |     | 160 |
| Tyr | Leu | Asp | Leu | Met | Ser | His | Ser | Gly | Thr | Ser | Leu | Thr | Gln | Ser | Val |
|     |     |     |     | 165 |     |     |     |     | 170 |     |     |     |     | 175 |     |
| Ala | Arg | Ala | Met | Leu | Arg | Phe | Val | Thr | Val | Thr | Ala | Glu | Ala | Leu | Arg |
|     |     |     | 180 |     |     |     |     | 185 |     |     |     |     | 190 |     |     |

```
Phe Arg Gln Ile Gln Arg Gly Phe Arg Thr Thr Leu Asp Asp Leu Ser
    195             200                 205
Gly Arg Ser Tyr Val Met Thr Ala Glu Asp Val Asp Leu Thr Leu Asn
    210             215                 220
Trp Gly Arg Leu Ser Ser Val Leu Pro Asp Tyr His Gly Gln Asp Ser
225             230              235                         240
Val Arg Val Gly Arg Ile Ser Phe Gly Ser Ile Asn Ala Ile Leu Gly
            245             250                         255
Ser Val Ala Leu Ile Leu Asn Cys His His Ala Ser Arg Val Ala
            260             265                 270
Arg Met Ala Ser Asp Glu Phe Pro Ser Met Cys Pro Ala Asp Gly Arg
        275             280                 285
Val Arg Gly Ile Thr His Asn Lys Ile Leu Trp Asp Ser Ser Thr Leu
    290             295                 300
Gly Ala Ile Leu Met Arg Arg Thr Ile Ser Ser
305             310             315
```

( 2 ) INFORMATION FOR SEQ ID NO:74:

( i ) SEQUENCE CHARACTERISTICS:
        ( A ) LENGTH: 267 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:74:

```
Gly Asp Val Ser Phe Arg Leu Ser Gly Ala Thr Ser Ser Ser Tyr Gly
1               5                   10                      15
Val Phe Ile Ser Asn Leu Arg Lys Ala Leu Pro Asn Glu Arg Lys Leu
            20              25                  30
Tyr Asp Ile Pro Leu Leu Arg Ser Ser Leu Pro Gly Ser Gln Arg Tyr
        35                  40                  45
Ala Leu Ile His Leu Thr Asn Tyr Ala Asp Glu Thr Ile Ser Val Ala
    50                  55                  60
Ile Asp Val Thr Asn Val Tyr Ile Met Gly Tyr Arg Ala Gly Asp Thr
65              70                  75                      80
Ser Tyr Phe Phe Asn Glu Ala Ser Ala Thr Glu Ala Ala Lys Tyr Val
            85                  90                  95
Phe Lys Asp Ala Met Arg Lys Val Thr Leu Pro Tyr Ser Gly Asn Tyr
            100             105                 110
Glu Arg Leu Gln Thr Ala Ala Gly Lys Ile Arg Glu Asn Ile Pro Leu
        115                 120                 125
Gly Leu Pro Ala Leu Asp Ser Ala Ile Thr Thr Leu Phe Tyr Tyr Asn
    130                 135                 140
Ala Asn Ser Ala Ala Ser Ala Leu Met Val Leu Ile Gln Ser Thr Ser
145             150                 155                     160
Glu Ala Ala Arg Tyr Lys Phe Ile Glu Gln Gln Ile Gly Lys Arg Val
            165                 170                 175
Asp Lys Thr Phe Leu Pro Ser Leu Ala Ile Ile Ser Leu Glu Asn Ser
        180                 185                 190
Trp Ser Ala Leu Ser Lys Gln Ile Gln Ile Ala Ser Thr Asn Asn Gly
    195                 200                 205
Gln Phe Glu Ser Pro Val Val Leu Ile Asn Ala Gln Asn Gln Arg Val
    210                 215                 220
```

```
Thr  Ile  Thr  Asn  Val  Asp  Ala  Gly  Val  Val  Thr  Ser  Asn  Ile  Ala  Leu
225                      230                      235                      240

Leu  Leu  Asn  Arg  Asn  Asn  Met  Ala  Ala  Met  Asp  Asp  Asp  Val  Pro  Met
                    245                      250                      255

Thr  Gln  Ser  Phe  Gly  Cys  Gly  Ser  Tyr  Ala  Ile
               260                 265
```

( 2 ) INFORMATION FOR SEQ ID NO:75:

( i ) SEQUENCE CHARACTERISTICS:
        ( A ) LENGTH: 248 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:75:

```
Asp  Val  Arg  Phe  Ser  Leu  Ser  Gly  Ser  Ser  Thr  Ser  Tyr  Ser  Lys
1                   5                   10                      15

Phe  Ile  Gly  Asp  Leu  Arg  Lys  Ala  Leu  Pro  Ser  Asn  Gly  Thr  Val  Tyr
               20                      25                      30

Asn  Leu  Thr  Ile  Leu  Leu  Ser  Ser  Ala  Ser  Gly  Ala  Ser  Arg  Tyr  Thr
          35                      40                           45

Leu  Met  Thr  Leu  Ser  Asn  Tyr  Asp  Gly  Lys  Ala  Ile  Thr  Val  Ala  Val
     50                      55                      60

Asp  Val  Ser  Gln  Leu  Tyr  Ile  Met  Gly  Tyr  Leu  Val  Asn  Ser  Thr  Ser
65                       70                      75                       80

Tyr  Phe  Phe  Asn  Glu  Ser  Asp  Ala  Lys  Leu  Ala  Ser  Gln  Tyr  Val  Phe
                    85                      90                           95

Lys  Gly  Ser  Thr  Ile  Val  Thr  Leu  Pro  Tyr  Ser  Gly  Asn  Tyr  Glu  Lys
               100                      105                     110

Leu  Gln  Thr  Ala  Ala  Gly  Lys  Ile  Arg  Glu  Lys  Ile  Pro  Leu  Gly  Phe
               115                      120                     125

Pro  Ala  Leu  Asp  Ser  Ala  Leu  Thr  Thr  Ile  Phe  His  Tyr  Asp  Ser  Thr
     130                      135                      140

Ala  Ala  Ala  Ala  Ala  Phe  Leu  Val  Ile  Leu  Gln  Thr  Thr  Ala  Glu  Ala
145                      150                      155                      160

Ser  Arg  Phe  Lys  Tyr  Ile  Glu  Gly  Gln  Ile  Ile  Glu  Arg  Ile  Ser  Lys
                    165                      170                     175

Asn  Gln  Val  Pro  Ser  Leu  Ala  Thr  Ile  Ser  Leu  Glu  Asn  Ser  Leu  Trp
               180                      185                     190

Ser  Ala  Leu  Ser  Lys  Gln  Ile  Gln  Leu  Ala  Gln  Thr  Asn  Asn  Gly  Thr
          195                      200                     205

Phe  Lys  Thr  Pro  Val  Val  Ile  Thr  Asp  Asp  Lys  Gly  Gln  Arg  Val  Glu
     210                      215                     220

Ile  Thr  Asn  Val  Thr  Ser  Lys  Val  Val  Thr  Lys  Asn  Ile  Gln  Leu  Leu
225                      230                      235                      240

Leu  Asn  Tyr  Lys  Gln  Asn  Val  Ala
                    245
```

( 2 ) INFORMATION FOR SEQ ID NO:76:

( i ) SEQUENCE CHARACTERISTICS:
        ( A ) LENGTH: 250 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:76:

| Ala | Pro | Thr | Leu | Glu | Thr | Leu | Ala | Ser | Leu | Asp | Leu | Asn | Asn | Pro | Thr |
|---|---|---|---|---|---|---|---|---|---|---|---|---|---|---|---|
| 1 | | | | 5 | | | | | 10 | | | | | 15 | |
| Thr | Tyr | Leu | Ser | Phe | Ile | Thr | Asn | Ile | Arg | Thr | Lys | Val | Val | Asp | Lys |
| | | | 20 | | | | | 25 | | | | | 30 | | |
| Thr | Glu | Gln | Cys | Thr | Ile | Gln | Lys | Ile | Ser | Lys | Thr | Phe | Thr | Gln | Arg |
| | | 35 | | | | | 40 | | | | | 45 | | | |
| Tyr | Ser | Tyr | Ile | Asp | Leu | Ile | Val | Ser | Ser | Thr | Gln | Lys | Ile | Thr | Leu |
| | 50 | | | | | 55 | | | | | 60 | | | | |
| Ala | Ile | Asp | Met | Ala | Asp | Leu | Tyr | Val | Leu | Gly | Tyr | Ser | Asp | Ile | Ala |
| 65 | | | | | 70 | | | | | 75 | | | | | 80 |
| Asn | Asn | Lys | Gly | Arg | Ala | Phe | Phe | Phe | Lys | Asp | Val | Thr | Glu | Ala | Val |
| | | | | 85 | | | | | 90 | | | | | 95 | |
| Ala | Asn | Asn | Phe | Phe | Pro | Gly | Ala | Thr | Gly | Thr | Asn | Arg | Ile | Lys | Leu |
| | | | 100 | | | | | 105 | | | | | 110 | | |
| Thr | Phe | Thr | Gly | Ser | Tyr | Gly | Asp | Leu | Glu | Lys | Asn | Gly | Gly | Leu | Arg |
| | | 115 | | | | | 120 | | | | | 125 | | | |
| Lys | Asp | Asn | Pro | Leu | Gly | Ile | Phe | Arg | Leu | Glu | Asn | Ser | Ile | Val | Asn |
| | 130 | | | | | 135 | | | | | 140 | | | | |
| Ile | Tyr | Gly | Lys | Ala | Gly | Asp | Val | Lys | Lys | Gln | Ala | Lys | Phe | Phe | Leu |
| 145 | | | | | 150 | | | | | 155 | | | | | 160 |
| Leu | Ala | Ile | Gln | Met | Val | Ser | Glu | Ala | Ala | Arg | Phe | Lys | Tyr | Ile | Ser |
| | | | | 165 | | | | | 170 | | | | | 175 | |
| Asp | Lys | Ile | Pro | Ser | Glu | Lys | Tyr | Glu | Glu | Val | Thr | Val | Gly | Glu | Tyr |
| | | | 180 | | | | | 185 | | | | | 190 | | |
| Met | Thr | Ala | Leu | Glu | Asn | Asn | Trp | Ala | Lys | Leu | Ser | Thr | Ala | Val | Tyr |
| | | 195 | | | | | 200 | | | | | 205 | | | |
| Asn | Ser | Lys | Pro | Ser | Thr | Thr | Thr | Ala | Thr | Lys | Cys | Gln | Leu | Ala | Thr |
| | 210 | | | | | 215 | | | | | 220 | | | | |
| Ser | Pro | Val | Thr | Ile | Ser | Pro | Trp | Ile | Phe | Lys | Thr | Val | Glu | Glu | Ile |
| 225 | | | | | 230 | | | | | 235 | | | | | 240 |
| Lys | Leu | Val | Met | Gly | Leu | Leu | Lys | Ser | Ser | | | | | | |
| | | | | 245 | | | | | 250 | | | | | | |

( 2 ) INFORMATION FOR SEQ ID NO:77:

( i ) SEQUENCE CHARACTERISTICS:
        ( A ) LENGTH: 540 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:77:

| Ile | Phe | Pro | Lys | Gln | Tyr | Pro | Ile | Ile | Asn | Phe | Thr | Thr | Ala | Asp | Ala |
|---|---|---|---|---|---|---|---|---|---|---|---|---|---|---|---|
| 1 | | | | 5 | | | | | 10 | | | | | 15 | |
| Thr | Val | Glu | Ser | Tyr | Thr | Asn | Phe | Ile | Arg | Ala | Val | Arg | Ser | His | Leu |
| | | | 20 | | | | | 25 | | | | | 30 | | |
| Thr | Thr | Gly | Ala | Asp | Val | Arg | His | Glu | Ile | Pro | Val | Leu | Pro | Asn | Arg |
| | | 35 | | | | | 40 | | | | | 45 | | | |
| Val | Gly | Leu | Pro | Ile | Ser | Gln | Arg | Phe | Ile | Leu | Val | Glu | Leu | Ser | Asn |
| | 50 | | | | | 55 | | | | | 60 | | | | |
| His | Ala | Glu | Leu | Ser | Val | Thr | Leu | Ala | Leu | Asp | Val | Thr | Asn | Ala | Tyr |
| 65 | | | | | 70 | | | | | 75 | | | | | 80 |
| Val | Val | Gly | Cys | Arg | Ala | Gly | Asn | Ser | Ala | Tyr | Phe | Phe | His | Pro | Asp |

-continued

|   |   |   |   | 85 |   |   |   |   | 90 |   |   |   |   | 95 |   |
|---|---|---|---|---|---|---|---|---|---|---|---|---|---|---|---|
| Asn | Gln | Glu | Asp 100 | Ala | Glu | Ala | Ile | Thr 105 | His | Leu | Phe | Thr | Asp 110 | Val | Gln |
| Asn | Ser | Phe 115 | Thr | Phe | Ala | Phe | Gly 120 | Gly | Asn | Tyr | Asp | Arg 125 | Leu | Glu | Gln |
| Leu | Gly 130 | Gly | Leu | Arg | Glu | Asn 135 | Ile | Glu | Leu | Gly | Thr 140 | Gly | Pro | Leu | Glu |
| Asp 145 | Ala | Ile | Ser | Ala | Leu 150 | Tyr | Tyr | Tyr | Ser | Thr 155 | Cys | Gly | Thr | Gln | Ile 160 |
| Pro | Thr | Leu | Ala | Arg 165 | Ser | Phe | Met | Val | Cys 170 | Ile | Gln | Met | Ile | Ser 175 | Glu |
| Ala | Ala | Arg | Phe 180 | Gln | Tyr | Ile | Glu | Gly 185 | Glu | Met | Arg | Thr | Arg 190 | Ile | Arg |
| Tyr | Asn | Arg 195 | Arg | Ser | Ala | Pro | Asp 200 | Pro | Ser | Val | Ile | Thr 205 | Leu | Glu | Asn |
| Ser | Trp 210 | Gly | Arg | Leu | Ser | Thr 215 | Ala | Ile | Gln | Glu | Ser 220 | Asn | Gln | Gly | Ala |
| Phe 225 | Ala | Ser | Pro | Ile | Gln 230 | Leu | Gln | Arg | Arg | Asn 235 | Gly | Ser | Lys | Phe | Asn 240 |
| Val | Tyr | Asp | Val | Ser 245 | Ile | Leu | Ile | Pro | Ile 250 | Ile | Ala | Leu | Met | Val 255 | Tyr |
| Arg | Cys | Ala | Pro 260 | Pro | Pro | Ser | Ser | Gln 265 | Phe | Ser | Leu | Leu | Ile 270 | Arg | Pro |
| Val | Val | Pro 275 | Asn | Phe | Asn | Ala | Asp 280 | Val | Cys | Met | Asp | Pro 285 | Glu | Pro | Ile |
| Val | Arg 290 | Ile | Val | Gly | Arg | Asn 295 | Gly | Leu | Cys | Val | Asp 300 | Val | Thr | Gly | Glu |
| Glu 305 | Phe | Phe | Asp | Gly | Asn 310 | Pro | Ile | Gln | Leu | Trp 315 | Pro | Cys | Lys | Ser | Asn 320 |
| Thr | Asp | Trp | Asn | Gln 325 | Leu | Trp | Thr | Leu | Arg 330 | Lys | Asp | Ser | Thr | Ile 335 | Arg |
| Ser | Asn | Gly | Lys 340 | Cys | Leu | Thr | Ile | Ser 345 | Lys | Ser | Ser | Pro | Arg 350 | Gln | Gln |
| Val | Val | Ile 355 | Tyr | Asn | Cys | Ser | Thr 360 | Ala | Thr | Val | Gly | Ala 365 | Thr | Arg | Trp |
| Gln | Ile 370 | Trp | Asp | Asn | Arg | Thr 375 | Ile | Ile | Asn | Pro | Arg 380 | Ser | Gly | Leu | Val |
| Leu 385 | Ala | Ala | Thr | Ser | Gly 390 | Asn | Ser | Gly | Thr | Lys 395 | Leu | Thr | Val | Gln | Thr 400 |
| Asn | Ile | Tyr | Ala | Val 405 | Ser | Gln | Gly | Trp | Leu 410 | Pro | Thr | Asn | Asn | Thr 415 | Gln |
| Pro | Phe | Val | Thr 420 | Thr | Ile | Val | Gly | Leu 425 | Tyr | Gly | Met | Cys | Leu 430 | Gln | Ala |
| Asn | Ser | Gly 435 | Lys | Val | Trp | Leu | Glu 440 | Asp | Cys | Thr | Ser | Glu 445 | Lys | Ala | Glu |
| Gln | Gln 450 | Trp | Ala | Leu | Tyr | Ala 455 | Asp | Gly | Ser | Ile | Arg 460 | Pro | Gln | Gln | Asn |
| Arg 465 | Asp | Asn | Cys | Leu | Thr 470 | Thr | Asp | Ala | Asn | Ile 475 | Lys | Gly | Thr | Val | Val 480 |
| Lys | Ile | Leu | Ser | Cys 485 | Gly | Pro | Ala | Ser | Ser 490 | Gly | Gln | Arg | Trp | Met 495 | Phe |
| Lys | Asn | Asp | Gly 500 | Thr | Ile | Leu | Asn | Leu 505 | Tyr | Asn | Gly | Leu | Val 510 | Leu | Asp |

```
Val  Arg  Arg  Ser  Asp  Pro  Ser  Leu  Lys  Gln  Ile  Ile  Val  His  Pro  Phe
          515                      520                     525

His  Gly  Asn  Leu  Asn  Gln  Ile  Trp  Leu  Pro  Leu  Phe
     530                      535                     540
```

( 2 ) INFORMATION FOR SEQ ID NO:78:

( i ) SEQUENCE CHARACTERISTICS:
        ( A ) LENGTH: 250 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:78:

```
Asp  Val  Ser  Phe  Arg  Leu  Ser  Gly  Ala  Asp  Pro  Arg  Ser  Tyr  Gly  Met
 1              5                         10                     15

Phe  Ile  Lys  Asp  Leu  Arg  Asn  Ala  Leu  Pro  Phe  Arg  Glu  Lys  Val  Tyr
               20                       25                     30

Asn  Ile  Pro  Leu  Leu  Leu  Pro  Ser  Val  Ser  Gly  Ala  Gly  Arg  Tyr  Leu
               35                       40                     45

Leu  Met  His  Leu  Phe  Asn  Tyr  Asp  Gly  Lys  Thr  Ile  Thr  Val  Ala  Val
     50                       55                      60

Asp  Val  Thr  Asn  Val  Tyr  Ile  Met  Gly  Tyr  Leu  Ala  Asp  Thr  Thr  Ser
65                       70                      75                          80

Tyr  Phe  Phe  Asn  Gln  Pro  Ala  Ala  Glu  Leu  Ala  Ser  Gln  Tyr  Val  Phe
                    85                       90                          95

Arg  Asp  Ala  Arg  Lys  Ile  Thr  Leu  Pro  Tyr  Ser  Gly  Asn  Tyr  Glu  Arg
                    100                      105                     110

Leu  Gln  Ile  Ala  Ala  Gly  Lys  Pro  Arg  Glu  Lys  Leu  Pro  Ile  Gly  Leu
               115                      120                     125

Pro  Ala  Ile  Asp  Ser  Ala  Ile  Ser  Thr  Leu  Leu  His  Tyr  Asp  Ser  Thr
     130                      135                     140

Ala  Ala  Ala  Gly  Ala  Leu  Val  Leu  Ile  Gln  Thr  Thr  Ala  Glu  Ala
145                           150                     155                     160

Ala  Arg  Phe  Lys  Tyr  Ile  Glu  Gln  Gln  Ile  Gln  Glu  Arg  Ala  Tyr  Arg
                    165                      170                     175

Asp  Glu  Val  Pro  Ser  Ile  Ala  Thr  Leu  Ser  Leu  Glu  Asn  Ser  Leu  Trp
               180                      185                     190

Ser  Gly  Leu  Ser  Lys  Gln  Ile  Gln  Leu  Ala  Gln  Gly  Asn  Asn  Gly  Ile
          195                      200                     205

Phe  Arg  Thr  Pro  Ile  Val  Leu  Val  Asp  Asn  Lys  Gly  Asn  Arg  Val  Gln
     210                      215                     220

Ile  Thr  Asn  Val  Thr  Ser  Lys  Val  Val  Thr  Ser  Asn  Ile  Gln  Leu  Leu
225                      230                      235                         240

Leu  Val  Thr  Arg  Asn  Ile  Ala  Glu  Gly  Asp
                    245                      250
```

( 2 ) INFORMATION FOR SEQ ID NO:79:

( i ) SEQUENCE CHARACTERISTICS:
        ( A ) LENGTH: 261 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:79:

```
Ile  Asn  Thr  Ile  Thr  Phe  Asp  Ala  Gly  Asn  Ala  Thr  Ile  Asn  Lys  Tyr
1                  5                        10                       15

Ala  Thr  Phe  Met  Glu  Ser  Leu  Arg  Asn  Glu  Ala  Lys  Asp  Pro  Ser  Leu
               20                       25                  30

Lys  Cys  Tyr  Gly  Ile  Pro  Met  Leu  Pro  Asn  Thr  Asn  Ser  Thr  Ile  Lys
          35                       40                       45

Tyr  Leu  Leu  Val  Lys  Leu  Gln  Gly  Ala  Ser  Leu  Lys  Thr  Ile  Thr  Leu
     50                            55                  60

Met  Leu  Arg  Arg  Asn  Asn  Leu  Tyr  Val  Met  Gly  Tyr  Ser  Asp  Pro  Tyr
65                       70                       75                       80

Asp  Asn  Lys  Cys  Arg  Tyr  His  Ile  Phe  Asn  Asp  Ile  Lys  Gly  Thr  Glu
                    85                       90                            95

Tyr  Ser  Asp  Val  Glu  Asn  Thr  Leu  Cys  Pro  Ser  Ser  Asn  Pro  Arg  Val
                    100                      105                      110

Ala  Lys  Pro  Ile  Asn  Tyr  Asn  Gly  Leu  Tyr  Pro  Thr  Leu  Glu  Lys  Lys
               115                      120                      125

Ala  Gly  Val  Thr  Ser  Arg  Asn  Glu  Val  Gln  Leu  Gly  Ile  Gln  Ile  Leu
     130                      135                      140

Ser  Ser  Asp  Ile  Gly  Lys  Ile  Ser  Gly  Gln  Gly  Ser  Phe  Thr  Glu  Lys
145                      150                      155                      160

Ile  Glu  Ala  Lys  Phe  Leu  Leu  Val  Ala  Ile  Gln  Met  Val  Ser  Glu  Ala
               165                      170                      175

Ala  Arg  Phe  Lys  Tyr  Ile  Glu  Asn  Gln  Val  Lys  Thr  Asn  Phe  Asn  Arg
               180                      185                 190

Asp  Phe  Ser  Pro  Asn  Asp  Lys  Val  Leu  Asp  Leu  Glu  Glu  Asn  Trp  Gly
          195                      200                      205

Lys  Ile  Ser  Thr  Ala  Ile  His  Asn  Ser  Lys  Asn  Gly  Ala  Leu  Pro  Lys
     210                      215                      220

Pro  Leu  Glu  Leu  Lys  Asn  Ala  Asp  Gly  Thr  Lys  Trp  Ile  Val  Leu  Arg
225                      230                      235                      240

Val  Asp  Glu  Ile  Lys  Pro  Asp  Val  Gly  Leu  Leu  Asn  Tyr  Val  Asn  Gly
                    245                      250                      255

Thr  Cys  Gln  Ala  Thr
                    260
```

(2) INFORMATION FOR SEQ ID NO:80:

(i) SEQUENCE CHARACTERISTICS:
        (A) LENGTH: 250 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:80:

```
Ala  Asn  Val  Ser  Phe  Ser  Leu  Ser  Gly  Ala  Asp  Ser  Lys  Ser  Tyr  Ser
1                   5                        10                       15

Lys  Phe  Ile  Thr  Ala  Leu  Arg  Lys  Ala  Leu  Pro  Ser  Lys  Glu  Lys  Val
               20                       25                  30

Ser  Asn  Ile  Pro  Leu  Leu  Leu  Pro  Ser  Ala  Ser  Gly  Ala  Ser  Arg  Tyr
          35                       40                       45

Ile  Leu  Met  Gln  Leu  Ser  Asn  Tyr  Asp  Ala  Lys  Ala  Ile  Thr  Met  Ala
     50                            55                  60

Ile  Asp  Val  Thr  Asn  Val  Tyr  Ile  Met  Gly  Tyr  Leu  Val  Asn  Ser  Thr
65                       70                       75                       80

Ser  Tyr  Phe  Ala  Asn  Glu  Ser  Asp  Ala  Lys  Leu  Ala  Ser  Gln  Tyr  Val
```

|     |     |     |     | 85  |     |     |     | 90  |     |     |     | 95  |     |     |
| --- | --- | --- | --- | --- | --- | --- | --- | --- | --- | --- | --- | --- | --- | --- |
| Phe | Lys | Gly | Ser | Thr | Leu | Val | Thr | Ile | Pro | Tyr | Ser | Gly | Asn | Tyr | Glu |
|     |     |     | 100 |     |     |     |     | 105 |     |     |     | 110 |     |     |
| Arg | Leu | Gln | Asn | Ala | Ala | Gly | Lys | Ile | Arg | Glu | Lys | Ile | Pro | Leu | Gly |
|     |     | 115 |     |     |     |     | 120 |     |     |     |     | 125 |     |     |
| Phe | Arg | Ala | Leu | Asp | Ser | Ala | Leu | Thr | Ser | Ile | Phe | His | Tyr | Asp | Ser |
|     | 130 |     |     |     |     | 135 |     |     |     |     | 140 |     |     |     |
| Thr | Ala | Ala | Ala | Ala | Ala | Phe | Leu | Val | Ile | Leu | Gln | Thr | Thr | Ala | Glu |
| 145 |     |     |     |     | 150 |     |     |     |     | 155 |     |     |     |     | 160 |
| Ala | Ser | Arg | Phe | Lys | Tyr | Ile | Glu | Gly | Gln | Ile | Ile | Glu | Arg | Ile | Pro |
|     |     |     |     | 165 |     |     |     |     | 170 |     |     |     |     | 175 |     |
| Lys | Asn | Glu | Val | Pro | Ser | Pro | Ala | Ala | Leu | Ser | Leu | Glu | Asn | Glu | Ala |
|     |     |     | 180 |     |     |     |     | 185 |     |     |     |     | 190 |     |     |
| Trp | Ser | Leu | Leu | Ser | Lys | Gln | Ile | Gln | Leu | Ala | Gln | Thr | Asn | Asn | Gly |
|     |     |     | 195 |     |     |     |     | 200 |     |     |     |     | 205 |     |     |
| Ala | Phe | Arg | Thr | Pro | Val | Val | Ile | Ile | Asp | Asn | Lys | Gly | Gln | Arg | Val |
|     |     | 210 |     |     |     |     | 215 |     |     |     |     | 220 |     |     |     |
| Glu | Ile | Thr | Asn | Leu | Ala | Ser | Lys | Val | Gln | Ile | Lys | Asp | Val | Asn | Ser |
| 225 |     |     |     |     | 230 |     |     |     |     | 235 |     |     |     |     | 240 |
| Lys | Leu | Leu | Leu | Asn | Lys | Gln | Asn | Ile | Ala |     |     |     |     |     |     |
|     |     |     |     | 245 |     |     |     |     | 250 |     |     |     |     |     |     |

( 2 ) INFORMATION FOR SEQ ID NO:81:

( i ) SEQUENCE CHARACTERISTICS:
       ( A ) LENGTH: 292 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:81:

|     |     |     |     |     |     |     |     |     |     |     |     |     |     |     |
| --- | --- | --- | --- | --- | --- | --- | --- | --- | --- | --- | --- | --- | --- | --- |
| Lys | Ile | Tyr | Leu | Val | Ala | Ala | Ile | Ala | Trp | Ile | Leu | Phe | Gln | Ser | Ser |
| 1   |     |     |     | 5   |     |     |     |     | 10  |     |     |     |     | 15  |     |
| Ser | Trp | Thr | Thr | Asp | Ala | Ala | Thr | Ala | Tyr | Thr | Leu | Asn | Leu | Ala | Asn |
|     |     |     | 20  |     |     |     |     | 25  |     |     |     |     | 30  |     |     |
| Pro | Ser | Ala | Ser | Gln | Tyr | Ser | Ser | Phe | Leu | Asp | Gln | Ile | Arg | Asn | Asn |
|     |     | 35  |     |     |     |     | 40  |     |     |     |     | 45  |     |     |     |
| Val | Arg | Asp | Thr | Ser | Leu | Ile | Tyr | Gly | Gly | Thr | Asp | Val | Glu | Val | Ile |
|     | 50  |     |     |     |     | 55  |     |     |     |     | 60  |     |     |     |     |
| Gly | Ala | Pro | Ser | Thr | Thr | Asp | Lys | Phe | Leu | Arg | Leu | Asn | Phe | Gln | Gly |
| 65  |     |     |     |     | 70  |     |     |     |     | 75  |     |     |     |     | 80  |
| Pro | Arg | Gly | Thr | Val | Ser | Leu | Gly | Leu | Arg | Arg | Glu | Asn | Leu | Tyr | Val |
|     |     |     |     | 85  |     |     |     |     | 90  |     |     |     |     | 95  |     |
| Val | Ala | Tyr | Leu | Ala | Met | Asp | Asn | Ala | Asn | Val | Asn | Arg | Ala | Tyr | Tyr |
|     |     |     | 100 |     |     |     |     | 105 |     |     |     |     | 110 |     |     |
| Phe | Lys | Asn | Gln | Ile | Thr | Ser | Ala | Glu | Leu | Thr | Ala | Leu | Phe | Pro | Glu |
|     |     | 115 |     |     |     |     | 120 |     |     |     |     | 125 |     |     |     |
| Val | Val | Val | Ala | Asn | Gln | Lys | Gln | Leu | Glu | Tyr | Gly | Glu | Asp | Tyr | Gln |
|     | 130 |     |     |     |     | 135 |     |     |     |     | 140 |     |     |     |     |
| Ala | Ile | Glu | Lys | Asn | Ala | Lys | Ile | Thr | Thr | Gly | Asp | Gln | Ser | Arg | Lys |
| 145 |     |     |     |     | 150 |     |     |     |     | 155 |     |     |     |     | 160 |
| Glu | Leu | Gly | Leu | Gly | Ile | Asn | Leu | Leu | Ile | Thr | Met | Ile | Asp | Gly | Val |
|     |     |     |     | 165 |     |     |     |     | 170 |     |     |     |     | 175 |     |
| Asn | Lys | Lys | Val | Arg | Val | Val | Lys | Asp | Glu | Ala | Arg | Phe | Leu | Leu | Ile |
|     |     |     | 180 |     |     |     |     | 185 |     |     |     |     | 190 |     |     |

```
Ala  Ile  Gln  Met  Thr  Ala  Glu  Ala  Ala  Arg  Phe  Arg  Tyr  Ile  Gln  Asn
          195                           200                      205

Leu  Val  Thr  Lys  Asn  Phe  Pro  Asn  Lys  Phe  Asp  Ser  Glu  Asn  Lys  Val
          210                 215                      220

Ile  Gln  Phe  Gln  Val  Ser  Trp  Ser  Lys  Ile  Ser  Thr  Ala  Ile  Phe  Gly
225                      230                           235                      240

Asp  Cys  Lys  Asn  Gly  Val  Phe  Asn  Lys  Asp  Tyr  Asp  Phe  Gly  Phe  Gly
                    245                      250                      255

Lys  Val  Arg  Gln  Ala  Lys  Asp  Leu  Gln  Met  Gly  Leu  Leu  Lys  Tyr  Leu
               260                      265                      270

Gly  Arg  Pro  Lys  Ser  Ser  Ser  Ile  Glu  Ala  Asn  Ser  Thr  Asp  Asp  Thr
          275                      280                      285

Ala  Asp  Val  Leu
290
```

We hereby claim:

1. A substantially pure protein having the amino acid sequence of SEQ ID NO:2, termed pro-Ribosome Inactivating Protein (proRIP), wherein the proRip has a selectively removable, internal peptide linker sequence that has from about 9 to about 25 amino acids which correspond to residues 162 through 186 of SEQ ID NO:2 or a 70% homologous sequence that will display biological inhibitor activity and is incapable of substantially inactivating eukaryotic ribosomes, but which can be converted by removal of the linker into a protein having α and β fragments and being capable of substantially inactivating eukaryotic ribosomes, wherein the α fragment has the amino acid sequence of residues 17 to 161 of SEQ ID NO:2 and the β fragment has the amino acid sequence of residues 187 to 287 of FIG. 1, SEQ ID NO:2.

2. A substantially pure protein, termed a pro-Ribosome inactivating Protein (proRIP), comprising a selectively removable, internal peptide linker sequence and is incapable of substantially inactivating eukaryotic ribosomes, but it can be converted by removal of the linker into a protein having α and β fragments, termed a RIP, that is capable of substantially inactivating eukaryotic ribosomes, said proRIP wherein, (1) the RIP is selected from the group consisting of Barley Translation Inhibitor (SEQ ID NO:26), Ricin A-chain RIP (SEQ ID NO:27), Abrin-A A-chain (SEQ ID NO:71), Saporin (SEQ ID NO:72), SLT-1 RIP (SEQ ID NO:73), Trichosanthin (SEQ ID NO:74), Luffin-A (SEQ ID NO:75), MAP (SEQ ID NO:76), Ricinus communis agglutinin (SEQ ID NO:77), Momordin (SEQ ID NO:78), PAP-S (SEQ ID NO:79), Luffin-B (SEQ-ID NO:80), and Dianthin 30 (SEQ ID NO:81, (2) a removable, internal peptide linker sequence that inhibits RIP activity and is 70% homologous to residues 162–186 of SEQ ID NO:2, (3) the proRIP is generated by inserting the linker peptide of (2) into a selected sequence of (1), and is inserted into said selected sequence of (1) in between any two amino acid residues within the following sequences: amino acid residues 148–158 of Barley Translation Inhibit or (SEQ ID NO:26), amino acid residues 152–162 of Ricin A-chain RIP (SEQ. ID NO:27), amino acid residues 138–148 of Abrin-A A-chain (SEQ ID NO:71), amino acid residues 153–163 of Saporin (SEQ ID NO:72), amino acid residues of 145–155 of SLT-1 RIP (SEQ ID NO:73), amino acid residues 139–149 of Trichosanthin (SEQ ID NO:74), amino acid residues 138–148 of Luffin-A (SEQ ID NO:75), amino acid residues 145–155 of MAP (SEQ ID NO:76), amino acid residues 152–162 of Ricinus communis agglutinin (SEQ ID NO:77), amino acid residues 138–148 of Momordin (SEQ ID NO:78), amino acid residues 151–161 of PAP-S (SEQ ID NO:79), amino acid residues 139–149 of Luffin-B (SEQ ID NO:80), or amino acid residues 174–184 of Dianthin 30 (SEQ ID NO:81).

3. A substantially pure protein, termed a Ribosome Inactivating Protein (RIP), having α and β fragments and being capable of substantially inactivating eukaryotic ribosomes, wherein the α fragment has the amino acid sequence of residues 17 to 161 of SEQ ID NO:2 and the β fragment has the amino acid sequence of residues 187 to 287 of SEQ ID NO:2.

4. A fusion protein capable of substantially inactivating eukaryotic ribosomes, said protein comprising an amino acid sequence selected from the group consisting of SEQ ID NOS:7, 9, 11, 13, 15, 17, 19, 21, 23, and 25.

5. A method for converting a pro-Ribosome Inactivating Protein (proRIP) into a RIP, said method comprising the following steps:
   a) providing a homogeneous protein, termed a proRIP, wherein the proRIP has a selectively removable, internal peptide linker sequence and is incapable of substantially inactivating eukaryotic ribosomes, but which can be converted by removal of the linker into a protein having α and β fragments, termed a RIP, that is capable of substantially inactivating eukaryotic ribosomes; and
   b) contacting the proRIP with a cleaving agent capable of deleting the linker to form a protein having α and β fragments, termed a RIP, that is capable of substantially inactivating eukaryotic ribosomes.

6. The methods of claim 5, wherein proRIP is a protein having the amino acid sequence of SEQ ID NO:2.

7. The method of claim 5, comprising the proRIP wherein, (1) the RIP is selected from the group consisting of Barley Translation Inhibitor (SEQ ID NO:26), Ricin A-chain RIP (SEQ ID NO:27), Abrin-A A-Chain (SEQ ID NO:71), Saporin (SEQ ID NO:72), SLT-1 RIP (SEQ ID NO:73), Trichosanthin (SEQ ID NO:74), Luffin-A (SEQ ID NO:75), MAP (SEQ ID NO:76), Ricinus communis agglutinin (SEQ ID NO:77), Momordin (SEQ ID NO:78), PAP-S (SEQ ID NO:79), Luffin-B (SEQ ID NO:80), and Dianthin 30 (SEQ ID NO:81), (2) a removable, internal peptide linker sequence that inhibits RIP activity and is 70% homologous to residues 162–186 of SEQ ID NO:2, (3) the proRIP is generated by inserting the linker of (2) peptide from a selected sequence of (1) and is inserted into said selected sequence of (1) in-between any two amino acid residues within the following sequences: amino acid residues 148–158 of Barley Translation Inhibitor (SEQ ID NO:26), amino acid residues 152–162 of Ricin A-chain RIP (SEQ ID NO:27), amino acid residues 138–148 of Abrin-A A-chain (SEQ ID NO:71), amino acid residues 153–163 of Saporin (SEQ ID NO:72), amino acid residues 145–155 of SLT-1 RIP (SEQ ID NO:73), amino acid residues 139–149 of Trichosanthin (SEQ ID NO:74), amino acid residues 138–148 of Luffin-A (SEQ ID NO:75), amino acid residues 145–155 of MAP (SEQ ID NO:76), amino acid residues 152–162 of Ricinus communis agglutinin (SEQ ID NO:77), amino acid residues 138–148 of Momordin (SEQ ID NO:78), amino acid residues 151–161 of PAP-S (SEQ ID NO:79), amino acid residues 139–149 of Luffin-B (SEQ ID NO:80), and amino acid residues 174–184 of Dianthin 30 (SEQ ID NO:81).

* * * * *

UNITED STATES PATENT AND TRADEMARK OFFICE
CERTIFICATE OF CORRECTION

PATENT NO.   : 5,635,384
DATED        : June 3, 1997
INVENTOR(S)  : Terence A. Walsh; Timothy D. Hey; Alice E. R. Morgan It is certified that error appears in the above-indentified patent and that said Letters Patent is hereby corrected as shown below:

Col. 129, line 60, "Inhibit or" should read -- Inhibitor --.

Col. 129, line 61, "SEQ. ID" should read -- SEQ ID --.

Signed and Sealed this

Twenty-seventh Day of January, 1998

Attest:

BRUCE LEHMAN

*Attesting Officer*    *Commissioner of Patents and Trademarks*